US012558027B2

(12) United States Patent
Etkin et al.

(10) Patent No.: US 12,558,027 B2
(45) **Date of Patent: \*Feb. 24, 2026**

(54) TREATMENT OF DEPRESSION USING MACHINE LEARNING

(71) Applicants: The Board of Trustees of the Leland Stanford Junior University, Stanford, CA (US); Board of Regents, The University of Texas System, Austin, TX (US); The United States Government as represented by the Department of Veterans Affairs, Washington, DC (US)

(72) Inventors: Amit Etkin, Palo Alto, CA (US); Madhukar Trivedi, Dallas, TX (US); Wei Wu, Palo Alto, CA (US)

(73) Assignees: The Board of Trustees of the Leland Stanford Junior University, Stanford, CA (US); Board of Regents, The University of Texas System, Austin, TX (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/072,452

(22) Filed: Mar. 6, 2025

(65) Prior Publication Data

US 2025/0268527 A1     Aug. 28, 2025

Related U.S. Application Data

(63) Continuation of application No. 17/282,624, filed as application No. PCT/US2019/056395 on Oct. 15, 2019, now Pat. No. 12,383,196.

(Continued)

(51) Int. Cl.
*G01N 33/48* (2006.01)
*A61B 5/00* (2006.01)
(Continued)

(52) U.S. Cl.
CPC .......... *A61B 5/4848* (2013.01); *A61B 5/0075* (2013.01); *A61B 5/165* (2013.01);
(Continued)

(58) Field of Classification Search
CPC ..... A61B 5/4848; A61B 5/0075; A61B 5/165; A61B 5/168; A61B 5/245; A61B 5/374;
(Continued)

(56) References Cited

U.S. PATENT DOCUMENTS

2014/0279746 A1     9/2014   De Bruin et al.
2017/0001016 A1     1/2017   De Ridder
(Continued)

FOREIGN PATENT DOCUMENTS

WO          2020081609 A1      4/2020

OTHER PUBLICATIONS

Extended European Search Report for Application No. EP 19874568.9, mailed on Oct. 18, 2022, 10 pages.
(Continued)

*Primary Examiner* — Russell S Negin
(74) *Attorney, Agent, or Firm* — Mintz Levin Cohn Ferris Glovsky and Popeo, P.C.

(57) ABSTRACT

Provided herein are, inter alia, methods for identifying subjects suffering from depression that will respond to treatment with an antidepressant.

14 Claims, 23 Drawing Sheets

Related U.S. Application Data

(60) Provisional application No. 62/838,080, filed on Apr. 24, 2019, provisional application No. 62/745,890, filed on Oct. 15, 2018.

(51) Int. Cl.

| | |
|---|---|
| *A61B 5/16* | (2006.01) |
| *A61B 5/245* | (2021.01) |
| *A61B 5/374* | (2021.01) |
| *A61B 5/377* | (2021.01) |
| *G01N 33/50* | (2006.01) |
| *G01R 33/48* | (2006.01) |
| *G06N 20/00* | (2019.01) |
| *G16H 30/20* | (2018.01) |
| *G16H 30/40* | (2018.01) |
| *G16H 40/67* | (2018.01) |
| *G16H 50/20* | (2018.01) |
| *G16H 50/70* | (2018.01) |
| *A61N 1/36* | (2006.01) |
| *A61N 1/38* | (2006.01) |
| *A61N 2/00* | (2006.01) |
| *G16H 20/10* | (2018.01) |
| *G16H 20/30* | (2018.01) |
| *G16H 20/40* | (2018.01) |
| *G16H 20/70* | (2018.01) |

(52) U.S. Cl.
CPC .............. *A61B 5/168* (2013.01); *A61B 5/245* (2021.01); *A61B 5/374* (2021.01); *A61B 5/377* (2021.01); *A61B 5/4082* (2013.01); *A61B 5/4088* (2013.01); *A61B 5/7267* (2013.01); *G01R 33/4806* (2013.01); *G01R 33/4808* (2013.01); *G06N 20/00* (2019.01); *G16H 30/20* (2018.01); *G16H 30/40* (2018.01); *G16H 40/67* (2018.01); *G16H 50/20* (2018.01); *G16H 50/70* (2018.01); *A61B 2562/0223* (2013.01); *A61N 1/36053* (2013.01); *A61N 1/38* (2013.01); *A61N 2/006* (2013.01); *G16H 20/10* (2018.01); *G16H 20/30* (2018.01); *G16H 20/40* (2018.01); *G16H 20/70* (2018.01)

(58) Field of Classification Search
CPC ..... A61B 5/377; A61B 5/4082; A61B 5/4088; A61B 5/7267; A61B 2562/0223; G01R 33/4806; G01R 33/4808; G06N 20/00; G16H 30/20; G16H 30/40; G16H 40/67; G16H 50/20; G16H 50/70; G16H 20/10; G16H 20/30; G16H 20/40; G16H 20/70; A61N 1/36053; A61N 1/38; A61N 2/006
See application file for complete search history.

(56) References Cited

U.S. PATENT DOCUMENTS

| | | |
|---|---|---|
| 2017/0309022 A1 | 10/2017 | Silbersweig et al. |
| 2021/0353224 A1 | 11/2021 | Etkin et al. |

OTHER PUBLICATIONS

International Search Report and Written Opinion for International Application No. PCT/US2019/056395, mailed on Jan. 10, 2020, 9 pages.

Arns, et al. (Jun. 2015) "EEG Alpha Asymmetry as a Gender-specific Predictor of Outcome to Acute Treatment with Different Antidepressant Medications in the Randomized iSPOT-D Study", Clinical neurophysiology: official journal of the International Federation of Clinical Neurophysiology, 127(1):509-519.

Arns, et al. (Oct. 2012) "Neurophysiological Predictors of Non-response to rTMS in Depression", Brain Stimulation, 5(4):569-576.

Beck, Aaron T., et al. (Sep. 2005) "The Current State of Cognitive Therapy: A 40-year Retrospective", JAMA Psychiatry, 62(9):953-959.

Behrens, et al. (Jun. 15, 2003) "Non-invasive Mapping of Connections Between Human Thalamus and Cortex using Diffusion Imaging", Nature Neuroscience, 6(7):750-757.

Bell, et al. (Nov. 1995) "An Information-Maximization Approach to Blind Separation and Blind Deconvolution", Neural Computation, 7(6):1129-1159.

Boyd, et al. (2004) "Convex Optimization", Cambridge University Press, 729 pages.

Bruder, et al. (Jun. 15, 2008) "Electroencephalographic Alpha Measures Predict Therapeutic Response to a Selective Serotonin Reuptake Inhibitor Antidepressant: Pre-and Post-treatment Findings", Biological Psychiatry, 63(12):1171-1177 (15 pages).

Buckner, et al. (Nov. 2011) "The Organization of the Human Cerebellum Estimated by Intrinsic Functional Connectivity", Journal of Neurophysiology, 106(5):2322-2345.

Cai, et al. (2010) "A Singular Value Thresholding Algorithm for Matrix Completion", SIAM Journal on optimization, 20:26 pages.

Candes, et al. (May 2011) "Robust Principal Component Analysis?", Journal of the ACM, Article No. 11, 58(3):37 pages.

Cawley, et al. (Oct. 1, 2006) "Gene Selection in Cancer Classification using Sparse Logistic Regression with Bayesian Regularization", Bioinformatic, 22(19):2348-2355.

Chekroud, et al. (2016) "Cross-trial Prediction of Treatment Outcome in Depression: A Machine Learning Approach", The Lancet Psychiatry, 3(3):243-250.

Chekroud, et al. (2017) "Reevaluating the Efficacy and Predictability of Antidepressant Treatments: A Symptom Clustering Approach", JAMA psychiatry, 74(4):370-378.

Chen, et al. (Dec. 3, 2013) "Causal Interactions Between Fronto-Parietal Central Executive and Default-Mode Networks in Humans", Proceedings of the National Academy of Sciences of the United States of America, 110(49):19944-19949.

Chen, et al. (Sep. 2013.) "Hippocampal Network Connectivity And Activation Differentiates Post-Traumatic Stress Disorder From Generalized Anxiety Disorder", Neuropsychopharmacology, 38(10):1889-1898.

Choi, et al. (Oct. 2012) "The Organization of the Human Striatum Estimated by Intrinsic Functional Connectivity", Journal of Neurophysiology, 108(8):2242-2263.

Churchland, et al. (Jul. 5, 2012) "Neural Population Dynamics During Reaching", Nature, 487(7405):51-56.

Cichocki, et al. (Jun. 2002) "Adaptive Blind Signal and Image Processing: Learning Algorithms and Applications", John Wiley & Sons.

Cipriani, et al. (Apr. 7, 2018) "Comparative Efficacy and Acceptability of 21 Antidepressant Drugs for the Acute Treatment of Adults with Major Depressive Disorder: A Systematic Review and Network Meta-analysis", Lancet, 391(10128):1357-1366.

Comon, Pierre (Apr. 1994) "Independent Component Analysis, A New Concept?", Signal Processing, 36(3):287-314.

Cunningham, et al. (Nov. 2014) "Dimensionality Reduction for Large-scale Neural Recordings", Nature Neuroscience, 17(11):1500-1509.

Donse, et al. (Nov. 2017) "Simultaneous rTMS and Psychotherapy in Major Depressive Disorder: Clinical Outcomes and Predictors from a Large Naturalistic Study", Brain Stimulation, 11(12):337-345.

Drysdale, et al. (Jan. 2017) "Resting-state Connectivity Biomarkers Define Neurophysiological Subtypes of Depression", Nature Medicine, 23(1):28-38.

Egner, et al. (Nov. 6, 2005) "Cognitive Control Mechanisms Resolve Conflict through Cortical Amplification of Task-relevant Information", Nature Neuroscience, 8(12):1784-1790.

Egner, et al. (Jun. 1, 2008) "Dissociable Neural Systems Resolve Conflict from Emotional versus Nonemotional Distracters", Cerebral Cortex, 18(6):1475-1484.

(56) References Cited

OTHER PUBLICATIONS

Ekman, et al. (1976) "Pictures of Facial Affect", Consulting Psychologists.

Etkin, et al. (Sep. 21, 2006) "Resolving Emotional Conflict: A Role for the Rostral Anterior Cingulate Cortex in Modulating Activity in the Amygdala", Neuron, 51(6):871-882.

Etkin, et al. (Nov. 2015) "The Neural Bases of Emotion Regulation", Nature Reviews Neuroscience, 6(11):693-700.

First, et al. (Jan. 2002) "Structured Clinical Interview for DSM-IV-TR Axis I Disorders, Research Version, Non-patient Edition", New York State Psychiatric Institute.

Fischl, Bruce (Aug. 12, 2012) "FreeSurfer", Neuroimage, 62(2):774-781.

Fonzo, et al. (Dec. 3, 2019) "Brain Regulation of Emotional Conflict Predicts Antidepressant Treatment Response for Depression", Nature Human Behaviour, 3(12):1319-1331 (32 pages).

Fournier, et al. (Jan. 6, 2010) "Antidepressant Drug Effects and Depression Severity: A Patient-level Meta-analysis", JAMA, 303(1):47-53.

Friston, et al. (1995) "Statistical Parametric Maps in Functional Imaging: A General Linear Approach", Human Brain Mapping, 2:189-210.

George, et al. (May 2010) "Daily Left Prefrontal Transcranial Magnetic Stimulation Therapy for Major Depressive Disorder: a sham-controlled randomized trial", Archives of General Psychiatry, 67(5):507-516.

Ghosh-Dastidar, et al. (Jan. 16, 2008) "Principal Component Analysis-enhanced Cosine Radial Basis Function Neural Network for Robust Epilepsy and Seizure Detection", IEEE Transactions on Biomedical Engineering, 55(2):512-518.

Gramfort, et al. (Sep. 6, 2010) "OpenMEEG: Opensource Software for Quasistatic Bioelectromagnetics", BioMedical Engineering OnLine, Article No. 45, 9:20 pages.

Gratton, et al. (Dec. 1992) "Optimizing the Use of Information: Strategic Control of Activation of Responses", Journal of Experimental Psychology: General, 121(4):480-506.

Grin-Yatsenko, et al. (Mar. 2010) "Independent Component Approach to the Analysis of EEG Recordings at Early Stages of Depressive Disorders", Clinical Neurophysiology, 121(3):281-289.

Gyurak, et al. (Apr. 2011) "Explicit and Implicit Emotion Regulation: A Dualprocess Framework", Cognition and Emotion, 25(3):400-412.

Hari, et al. (Jan. 1997) "Human Cortical Oscillations: A Neuromagnetic View through the Skull", Trends in Neurosciences (1), 20(1):44-49.

Haufe, et al. (Feb. 2014) "On the Interpretation of Weight Vectors of Linear Models in Multivariate Neuroimaging", NeuroImage, 87:96-110.

Hill, et al. (May 2016) "Tms-Eeg: A Window into the Neurophysiological Effects of Transcranial Electrical Stimulation in Non-Motor Brain Regions", Neuroscience & Biobehavioral Reviews, 64:175-184.

Hunter, et al. (Aug. 2006) "Changes in Brain Function (Quantitative EEG Cordance) during Placebo Lead-in and Treatment Outcomes in Clinical Trials for Major Depression", The American Journal of Psychiatry, 163(8):1426-1432.

Iosifescu, et al. (Nov. 2009) "Frontal EEG Predictors of Treatment Outcome in Major Depressive Disorder", European Neuropsychopharmacology, 19(11):772-777.

Jaworska, et al. (Jan. 14, 2019) "Leveraging Machine Learning Approaches for Predicting Antidepressant Treatment Response using Electroencephalography (EEG) and Clinical Data", Frontiers in Psychiatry, Article 768, 9:16 pages.

Jenkinson, et al. (Aug. 15, 2012) "FSL", NeuroImage, 62(2):782-790.

Jensen, et al. (Nov. 4, 2010) "Shaping Functional Architecture by Oscillatory Alpha Activity: Gating by Inhibition", Frontiers in Human Neuroscience, 4:8 pages.

Jolliffe, et al. (2011) "Principal Component Analysis", International Encyclopedia of Statistical Science, pp. 1094-1096.

Kerns, et al. (Mar. 2004) "Anterior Cingulate Conflict Monitoring and Adjustments in Control", Science, 303(5660):1023-1026.

Khan, et al. (Oct. 2015) "Antidepressants Versus Placebo in Major Depression: An Overview", World Psychiatry., 14(3):294-300.

Kirsch, et al. (Feb. 26, 2008) "Initial Severity and Antidepressant Benefits: A Meta-Analysis of Data Submitted to the Food and Drug Administration", PLoS Medicine, e5, 5(2):9 pages.

Kirsch, I. (2009) "The Emperor's New Drugs: Exploding the Antidepressant Myth", Random House.

Klimesch, et al. (Jan. 2007) "EEG Alpha Oscillations: The Inhibition-timing Hypothesis", Brain Research Reviews, 53(1):63-88.

Kohavi, et al. (Aug. 1995) "A Study of Cross-validation and Bootstrap for Accuracy Estimation and Model Selection", IJCAI'95: Proceedings of the 14th international joint conference on Artificial intelligence, 2:1137-1143.

Korb, et al. (Jul. 2009) "Rostral Anterior Cingulate Cortex Theta Current Density and Response to Antidepressants and Placebo in Major Depression", Clinical Neurophysiology, 120(7):1313-1319.

Kraemer, Helena Chmura (Jul. 1, 2016) "Messages for Clinicians: Moderators and Mediators of Treatment Outcome in Randomized Clinical Trials", The American Journal of Psychiatry, 173(7):672-679.

Krepel, et al. (May-Jun. 2018) "Non-Replication of Neurophysiological Predictors of Non- Response to rTMS in Depression and Neurophysiological Data-Sharing Proposal", Brain Stimulation, 11(3):639-641.

Lehtonen, et al. (Feb. 1972) "Alpha Rhythm and Uniform Visual Field in Man", Electroencephalography and Clinical Neurophysiology, 32(2):139-147.

Leuchter, et al. (Feb. 2002) "Changes in Brain Function of Depressed Subjects During Treatment With Placebo", American Journal of Psychiatry, 159(1):122-129.

Leuchter, et al. (Sep. 30, 2009) "Comparative Effectiveness of Biomarkers and Clinical Indicators for Predicting Outcomes of SSRI Treatment in Major Depressive Disorder: Results of the Brite-MD Study", Psychiatry Research, 169(2):124-131.

Li, et al. (Oct. 2002) "Bayesian Automatic Relevance Determination Algorithms for Classifying Gene Expression Data", Bioinformatics, 18(10):1332-1339.

Liston, et al. (Oct. 1, 2014) "Default Mode Network Mechanisms of Transcranial Magnetic Stimulation in Depression", Biological Psychiatry, 76(7):517-526.

Liu, et al. (2009) "Multi-Task Feature Learning Via Efficient 12,1-Norm Minimization", Proceedings of the Twenty-Fifth Conference on Uncertainty in Artificial Intelligence, 339-348.

Lovibond, et al. (Mar. 1995) "The Structure of Negative Emotional States: Comparison of the Depression Anxiety Stress Scales (DASS) with the Beck Depression and Anxiety Inventories", Behaviour Research and Therapy, 33(3):335-343.

Makeig, et al. (1996) "Independent Component Analysis of Electroencephalographic Data", Advances in Neural Information Processing Systems, 145-151.

Mir-Moghtadaei, et al. (Sep.-Oct. 2015) "Concordance Between BeamF3 and MRI-neuronavigated Target Sites for Repetitive Transcranial Magnetic Stimulation of the Left Dorsolateral Prefrontal Cortex", Brain Stimulation, 8(5):965-973.

MULLEN (2012) "NITRC: CleanLine: Tool/Resource Info", NeuroImaging Tools and Resources Collaboratory.

Müller (Jan. 15, 2008) "Machine Learning for Real-time Single-trial EEG-analysis: From Brain-computer Interfacing to Mental State Monitoring", Journal of Neuroscience Methods, 167(1):82-90 (18 pages).

Nesterov, Y. E. (1983) "A Method for Solving the Convex Programming Problem with Convergence Rate $O(1/k^2)$", Proceedings of the USSR Academy of Sciences, vol. 269, pp. 543-547.

Nguyen, et al. (Jul. 2015) "Cost-Effectiveness of Repetitive Transcranial Magnetic Stimulation versus Antidepressant Therapy for Treatment-Resistant Depression", Value Health, 18(5):597-604.

Nunez, et al. (2009) "Electric Fields of the Brain: The Neurophysics of EEG", Oxford University Press, 626 pages.

Olbrich, et al. (Oct. 2013) "ECG Biomarkers in Major Depressive Disorder: Discriminative Power and Prediction of Treatment Response", International Review of Psychiatry, 25(5):604-618.

(56)          References Cited

OTHER PUBLICATIONS

O'Reardon, et al. (Dec. 2007) "Efficacy and Safety of Transcranial Magnetic Stimulation in the Acute Treatment of Major Depression: A Multisite Randomized Controlled Trial", Biological Psychiatry, 62(11):1208-1216.

Parikh, Neal (2014) "Proximal algorithms", Foundations and Trends® in Optimization 1, 127-239.

Pascual-Marqui, Roberto D. (2002) "Standardized Low-resolution Brain Electromagnetic Tomography (sLORETA): Technical Details", Methods and Findings in Experimental and Clinical, 24(Suppl D):5-12.

Patenaude, et al. (Jun. 1, 2011) "A Bayesian Model of Shape and Appearance for Subcortical Brain Segmentation", Neuroimage, 56(3):907-922.

Perrin, et al. (Feb. 1989) "Spherical Splines for Scalp Potential and Current Density Mapping", Electroencephalography and Clinical Neurophysiology, 72(2):184-187.

Pizzagalli, et al. (Jun. 1, 2018) "Pretreatment Rostral Anterior Cingulate Cortex Theta Activity in Relation to Symptom Improvement in Depression: A Randomized Clinical Tria", JAMA Psychiatry, 75(6):547-554.

Pozzi, et al. (Nov. 15, 1995) "Quantified Electroencephalographic Changes in Depressed Patients with and without Dementia", Biological Psychiatry, 38(10):677-683.

Ramoser, et al. (Jan. 2001) "Optimal Spatial Filtering of Single Trial EEG during Imagined Hand Movement", IEEE Transactions on Rehabilitation Engineering, 8(4):441-446.

Sani, et al. (Nov. 2018) "Mood Variations Decoded from Multi-site Intracranial Human Brain Activity", Nature Biotechnology, 36(10):954-961.

Schaefer, et al. (Sep. 2018) "Local-global Parcellation of the Human Cerebral Cortex from Intrinsic Functional Connectivity MRI", Cerebral Cortex, 28(9):3095-3114.

Schirrmeister, et al. (Nov. 2017) "Deep Learning with Convolutional Neural Networks For EEG Decoding and Visualization", Human Brain Mapping, 38(11):5391-5420.

Smith, et al. (2004) "Advances in Functional and Structural MR Image Analysis and Implementation as FSL", Neuroimage, 23(Suppl 1):S208-S219.

Srebro, et al. (2003) "Weighted Low-rank Approximations", Proceedings of the 20th International Conference on Machine Learning (ICML-03), 720-727.

Team (2015) "R: A Language and Environment for Statistical Computing", R Foundation for Statistical Computing, 55 Pages.

Tipping, et al. (1999) "Probabilistic Principal Component Analysis", Journal of the Royal Statistical Society: Series B (Statistical Methodology), 61(3):611-622.

Tipping, Michael E. (2001) "Sparse Bayesian Learning and the Relevance Vector Machine", Journal of Machine Learning Research, 1:211-244.

Tomioka, et al. (Jan. 1, 2010) "A Regularized Discriminative Framework for EEG Analysis with Application to Brain-computer Interface", Neurolmage, 49(1):415-432.

Trivedi, et al. "Comprehensive Phenotyping of Depression Disease Trajectory and Risk: Rationale and Design of DFW 5000".

Trivedi, et al. (Jul. 2016) "Establishing Moderators and Biosignatures of Antidepressant Response in Clinical Care (EMBARC): Rationale and Design", Journal of Psychiatric Research, 78:11-23.

Van Buuren, et al. (Dec. 2011) "MICE: Multivariate Imputation by Chained Equations in R", Journal of Statistical Software, 45(3):1-67.

Voigt, et al. (Oct. 2017) "Cost Effectiveness Analysis Comparing Repetitive Transcranial Magnetic Stimulation to Antidepressant Medications after a First Treatment Failure for Major Depressive Disorder in Newly Diagnosed Patients—A Lifetime Analysis", PLoS ONE, e0186950, 12(10):e0186950.

Wade, et al. (Sep. 2016) Using Electroencephalography for Treatment Guidance in Major Depressive Disorder, Biological Psychiatry: Cognitive Neuroscience and Neuroimaging, 1(5):411-422.

Widge, et al. (Jan. 1, 2019) "Electroencephalographic Biomarkers for Treatment Response Prediction in Major Depressive Illness: A Meta-Analysis", The American Journal of Psychiatry, 176(1):44-56.

Williams, et al. (May 3, 2016) "Childhood Trauma Predicts Antidepressant Response in Adults with Major Depression: Data from the Randomized International Study to Predict Optimized Treatment for Depression", Translational Psychiatry, e799, 6(5):7 pages.

Witten, et al. (2016) "Data Mining: Practical Machine Learning Tools and Techniques", Morgan Kaufmann.

Wright, et al. (2009) "Robust Principal Component Analysis: Exact Recovery of Corrupted Low-Rank Matrices via Convex Optimization", Advances in Neural Information Processing Systems 22 (NIPS 2009), 2080-2088.

Wu, et al. (Apr. 2018) "A Fully Automated Artifact Rejection Algorithm for Single-pulse TMS-EEG Data", Human Brain Mapping, 39(4):1607-1625.

Wu, et al. (Dec. 25, 2015) "Bayesian Machine Learning: EEG/MEG Signal Processing Measurements", IEEE Signal Processing Magazine, 33(1):14-36.

Zhang, et al. (Nov. 2016) "Sparse Bayesian Classification of EEG for Brain-computer Interface", IEEE Transactions on Neural Networks and Learning Systems, 27(11):12 pages.

Placebo. In P. Lagasse & Columbia University, The Columbia Encyclopedia (8th edition). Columbia University Press, 2018. Obtained online from credoreference.com on Apr. 19, 2025 (Year: 2018).

latent signal with most
positive regression weight latent signal with most
negative regression weight scalp spatial pattern
weights latent signal with most
positive regression weight latent signal with most
negative regression weight cortical spatial pattern
weights

30 seconds

Block 1

PBO REO latent signal with most
positive regression weight latent signal with most
negative regression weight scalp spatial pattern
weights

− 0 +

PBO REC latent signal with most
positive regression weight latent signal with most
negative regression weight scalp spatial pattern
weights

− 0 + cortical spatial pattern
weights

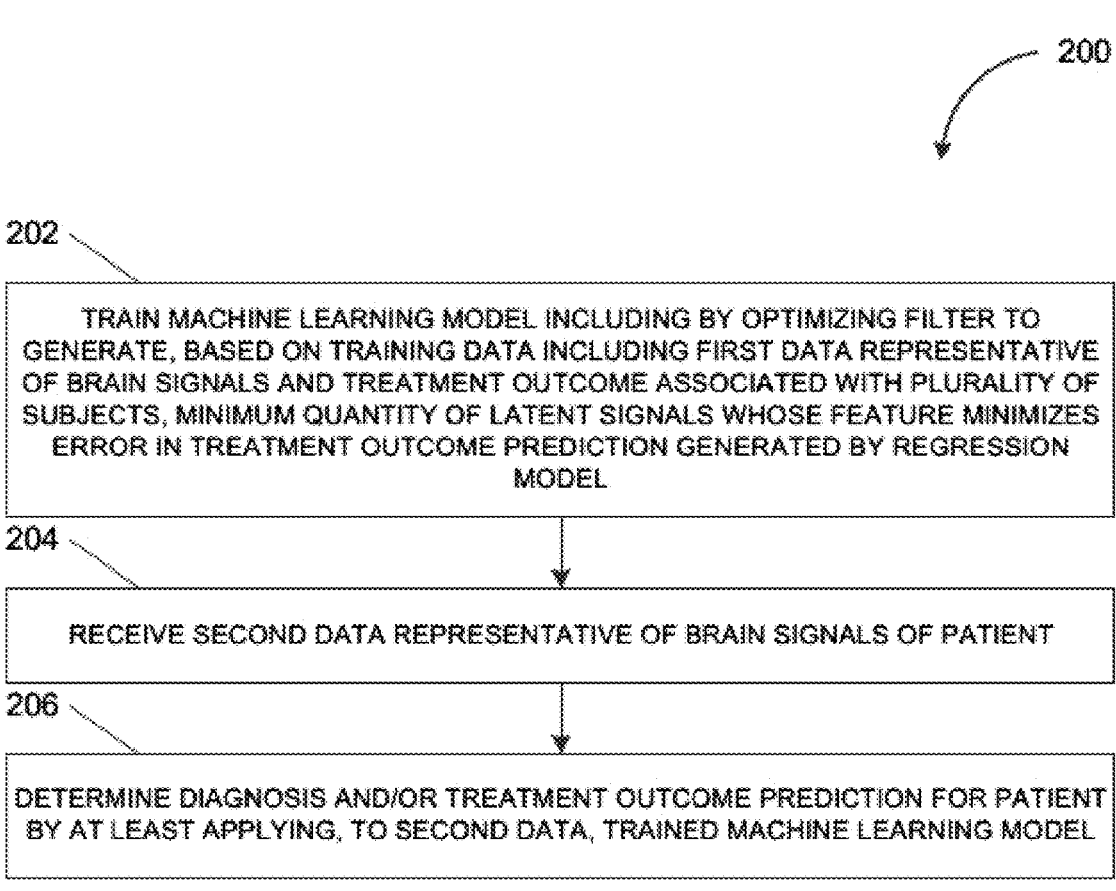

200

202

TRAIN MACHINE LEARNING MODEL INCLUDING BY OPTIMIZING FILTER TO GENERATE, BASED ON TRAINING DATA INCLUDING FIRST DATA REPRESENTATIVE OF BRAIN SIGNALS AND TREATMENT OUTCOME ASSOCIATED WITH PLURALITY OF SUBJECTS, MINIMUM QUANTITY OF LATENT SIGNALS WHOSE FEATURE MINIMIZES ERROR IN TREATMENT OUTCOME PREDICTION GENERATED BY REGRESSION MODEL

204

RECEIVE SECOND DATA REPRESENTATIVE OF BRAIN SIGNALS OF PATIENT

206

DETERMINE DIAGNOSIS AND/OR TREATMENT OUTCOME PREDICTION FOR PATIENT BY AT LEAST APPLYING, TO SECOND DATA, TRAINED MACHINE LEARNING MODEL

FIG. 21

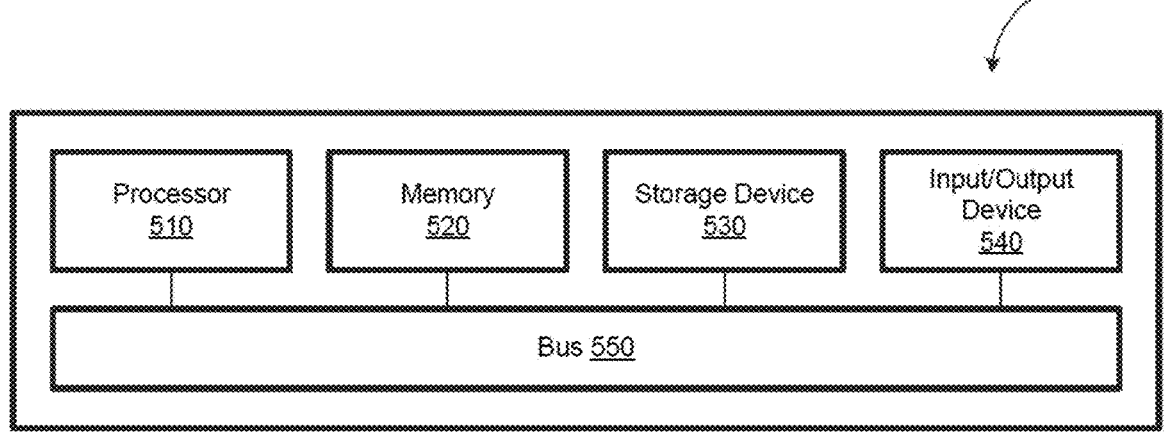

500

| Processor 510 | Memory 520 | Storage Device 530 | Input/Output Device 540 |

Bus 550

TREATMENT OF DEPRESSION USING MACHINE LEARNING

RELATED APPLICATIONS

This application is a continuation application of U.S. application Ser. No. 17/282,624 filed Apr. 2, 2021, which is a national stage entry of Patent Cooperation Treaty Application No. PCT/US2019/056395 filed Oct. 15, 2019, entitled "TREATMENT OF DEPRESSION USING MACHINE LEARNING," which claims priority to U.S. Provisional Application No. 62/745,890, filed Oct. 15, 2018, entitled "TREATMENT OF DEPRESSION USING MACHINE LEARNING," and U.S. Provisional Application No. 62/838,080, filed Apr. 24, 2019, entitled "TREATMENT OF DEPRESSION USING MACHINE LEARNING." The entire contents of these applications are incorporated herein by reference in their entirety.

STATEMENT AS TO RIGHTS TO INVENTIONS MADE UNDER FEDERALLY SPONSORED RESEARCH AND DEVELOPMENT

This invention was made with Government support under MH116506 awarded by the National Institutes of Health. The Government has certain rights in the invention.

BACKGROUND

Major depression is a common, chronic and disabling medical condition, whose treatment mainstay over the past four decades has been monoaminergic antidepressant medications. As a result, roughly one in eight in the US takes antidepressants. Nonetheless, large meta-analyses have found only a small overall advantage of antidepressants over placebo when used in an unselected population of depressed patients, with clinical significance only in the most severe patients—a severity level the vast majority of depressed patients never reach. However, the clinical diagnosis of depression is composed of a heterogeneous mixture of biological phenotypes, which are not quantified in clinical trials or in clinical practice. As such, it may be that the small overall average superiority of antidepressants over placebo belies critical biological differences amongst depressed patients. That is, for some patients, antidepressants are far superior to placebo, while for others there is no benefit. Objective measures that can stratify depressed patients into those with clinically significant superiority of antidepressants over placebo, and those not seeing these benefits, are thus needed. Provided herein are solutions to this and other needs in the art.

BRIEF SUMMARY

In an aspect, a method of identifying antidepressant-responsive depression phenotypes in subjects undergoing treatment of depression with an antidepressant using a machine learning model is provided. In embodiments, the machine learning model is a Sparse Electroncephalography Latent SpacE Regression (SELSER) computational model computational model. In embodiments, the antidepressant is sertraline.

In another interrelated aspect, a system is provided, the system including: at least one data processor; and at least one memory storing instructions which, when executed by the at least one data processor, result in operations including: determining a treatment outcome prediction for a patient by at least applying, to a representation of a first data corresponding to one or more brain signals of the patient, a machine learning model, the machine learning model including a filter configured to generate, based at least on the representation of the first data, a first plurality of latent signals, the machine learning model further including a regression model configured to generate, based at least on a feature of each of the first plurality of latent signals, the treatment outcome prediction, the machine learning model having been trained by at least optimizing the filter to generate a reduced quantity of latent signals whose feature minimizes an error in the treatment outcome prediction generated by the regression model; and providing an indication corresponding to the treatment outcome prediction.

In embodiments, the first data includes an electroencephalogram (EEG) data, a transcranial magnetic stimulation electroencephalogram (TMS-EEG) data, a magnetoencephalography (MEG) data, a functional magnetic resonance imaging (fMRI) data, and/or a functional near-infrared spectroscopy (fNIRS) data. In embodiments, the representation of the first data includes a covariance matrix summarizing a spatial distribution, a frequency distribution, and/or a power distribution of the brain signals. In embodiments, the reduced quantity of latent signals includes a minimum quantity of latent signals. In embodiments, the feature includes a band power, a power-envelope connectivity, a weighted phase-lag index, an imaginary coherence, a cordance, an approximate entropy, a Shannon entropy, and/or a cross-frequency coupling. In embodiments, the filter is configured to reduce a dimensionality of the first data of the patient including by merging, into a single latent signal, two or more signals in the first data, and wherein the two or more signals are merged based at least on a covariance between the two or more signals.

In embodiments, the machine learning model further includes a feature extractor configured to extract the feature of each of the first plurality of latent signals. In embodiments, the system further includes: training, based at least on training data, the machine learning model, the training data including a second data corresponding to one or more brain signals of a plurality of subjects, and the training data further including a treatment outcome associated with each of the plurality of subjects. In embodiments, the system further includes: clustering the second data, the second data being clustered based at least on the feature of each of a second plurality of latent signals generated by the filter based on the second data, and the clustering generating one or more clusters that each correspond to a type of a psychiatric disease. In embodiments, the system further includes: determining, based at least on the feature of each of the first plurality of latent signals associated with the patient, a diagnosis for the patient indicating the patient as having one or more types of the psychiatric disease, the diagnosis being determined by at least determining a distance between the feature of each of the first plurality of latent signals associated with the patient and the one or more clusters.

In embodiments, the psychiatric disease includes depression, mania, bipolar disorder, anxiety, obsessive-compulsive disorder, schizophrenia, an eating disorder, stroke, dementia, Alzheimer's disease, Parkinson's disease, or attention deficit disorder.

In embodiments, the regression model includes a linear regression model. In embodiments, the one or more brain signals include resting state brain signals. In embodiments, the one or more brain signals include brain signals during and/or after performance of a task. In embodiments, the one or more brain signals include brain signals responsive to a direct brain stimulation. In embodiments, the treatment outcome prediction includes a first response to a first treatment and a second response to a second treatment. In embodiments, the first treatment includes a first treatment modality and the second treatment includes a second treatment modality, and wherein the first treatment modality and the second treatment modality each include a different one of medication, psychotherapy, and somatic therapy. In embodiments, the first treatment and the second treatment each include a different variety of a same treatment modality. In embodiments, the first treatment and the second treatment each include a different one of a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, and an over-the-counter antidepressant. In embodiments, the first treatment and the second treatment each include a different one of electroconvulsive therapy (ECT), vagal nerve stimulation (VNS), and transcranial magnetic stimulation (TMS).

In embodiments, the treatment outcome prediction further includes, based at least on a difference between the first response and the second response, a selection of the first treatment and/or the second treatment. In embodiments, the treatment outcome prediction includes a third response to a treatment and a fourth response to a placebo, and wherein the treatment outcome prediction further identifies, based at least on a difference between the third response and the fourth response, the patient as being responsive or non-responsive to the treatment. In embodiments, the third response and the fourth response include one or more symptoms, behavioral tests, and psychological tests. In embodiments, the first data includes a first change in the one or more brain signals between at a first time prior to a treatment and a second time subsequent to the treatment, wherein the machine learning model is trained to correlate the first change in the one or more brain signals and a second change in one or more symptoms exhibited by the patient in response to the treatment, and wherein the treatment outcome prediction includes the second change in the one or more symptoms exhibited by the patient.

In another, interrelated aspect, a system is provided, the system including: at least one data processor; and at least one memory storing instructions which, when executed by the at least one data processor, result in operations including: training, based at least on training data, a machine learning model, the training data including a first data corresponding to one or more brain signals of a subject, the training data further including a treatment outcome associated with the subject, the machine learning model including a filter configured to generate, based at least on the first data, a first plurality of latent signals, the machine learning model further including a regression model configured to generate, based at least on a feature of each of the first plurality of latent signals, a first treatment outcome prediction for the subject, the training of the machine learning model including optimizing the filter to generate a reduced quantity of latent signals whose feature minimizes an error in the first treatment outcome prediction generated by the regression model, the error including a difference between the treatment outcome of the subject and the first treatment outcome prediction generated by the regression model; and deploying the trained machine learning model.

In embodiments, the first data includes an electroencephalogram (EEG) data, a transcranial magnetic stimulation electroencephalogram (TMS-EEG) data, a magnetoencephalography (MEG) data, a functional magnetic resonance imaging (fMRI) data, and/or a functional near-infrared spectroscopy (fNIRS) data. In embodiments, the training data includes a representation of the first data, and wherein the representation of the first data includes a covariance matrix summarizing a spatial distribution, a frequency distribution, and/or a power distribution of the brain signals. In embodiments, the trained machine learning model is deployed to at least determine, based at least on a representation of a second data corresponding to one or more brain signals of a subject, a second treatment outcome prediction for the patient. In embodiments, the second treatment outcome prediction includes a first response to a first treatment and a second response to a second treatment, and wherein the second treatment outcome prediction further includes, based at least on a difference between the first response and the second response, a selection of the first treatment and/or the second treatment. In embodiments, the first treatment includes a first treatment modality and the second treatment includes a second treatment modality, and wherein the first treatment modality and the second treatment modality each include a different one of medication, psychotherapy, and somatic therapy. In embodiments, the first treatment and the second treatment each include a different variety of a same treatment modality. In embodiments, the second treatment outcome prediction includes a third response to a treatment and a fourth response to a placebo, and wherein the second treatment outcome prediction further identifies, based at least on a difference between the third response and the fourth response, the patient as being responsive or non-responsive to the treatment.

In embodiments, the one or more brain signals include resting state brain signals. In embodiments, the one or more brain signals include brain signals during and/or after performance of a task. In embodiments, the one or more brain signals include brain signals responsive to a direct brain stimulation.

BRIEF DESCRIPTION OF THE DRAWINGS

(FIG. 2A) 10×10 stratified cross-validation prediction of $HAMD_{17}$ change in the sertraline group using SELSER. (FIG. 2B) Application of the sertraline-trained model to the placebo group failed to predict outcome, demonstrating specificity of the model for sertraline prediction. (FIG. 2C) Scalp spatial patterns of the SELSER latent signals, with the most positive ($\beta$=759.31; left) and negative ($\beta$=−853.13; right) regression weights, respectively. (FIG. 2D) Cortical spatial patterns of the SELSER latent signals, with the most positive ($\beta$=759.31; left) and negative ($\beta$=−853.13; right) regression weights, respectively. (FIG. 2E) Purely for the purpose of visualizing the utility of the rsEEG predictive signature, patients in each arm were partitioned into the low and high groups by applying a median split on the cross-validated predicted HAMD$_{17}$ score changes for sertraline response. The response rate was then calculated for each group (defined as a 50% or greater decrease in symptoms from baseline). SER=sertraline, PBO=placebo. (FIG. 2F) Treatment prediction across study sites in a leave-study-site-out cross-validation on the alpha REO sertraline model. Study sites were Columbia University (CU), University of Texas Southwestern Medical Center (TX), University of Michigan (UM) and Massachusetts General Hospital (MG). Site effect was corrected for by removing mean of the covariance matrix from each study site prior to the SELSER analysis.

(FIGS. 3A and 3C) 10×10 stratified cross-validation prediction of HAMD$_{17}$ change in the placebo group using SELSER on resting eyes open (FIG. 3A) and resting eyes closed (FIG. 3C) alpha-frequency range data, respectively. (FIGS. 3B and 3D) Application of the resting eyes open (FIG. 3B) and resting eyes closed (FIG. 3D) placebo-trained models to the sertraline group failed to predict outcome, demonstrating specificity of the model for placebo prediction.

(FIG. 6A) The EMBARC-trained rsEEG and task fMRI models were applied to an independent MDD data set that had both data types, and the ensuing predicted HAMD$_{17}$ changes from both models were correlated with each other. spTMS/EEG correlates of the rsEEG phenotype in the independent depressed data set. (FIG. 6B) TMS was delivered to bilateral posterior dorsolateral prefrontal cortices (pDLPFC, part of the fronto-parietal control network), anterior DLPFC (aDLPFC, part of the ventral attention network), primary motor cortex (M1), and primary visual cortex (V1). These sites were identified based on independent components analyses on resting-state fMRI data from a separate cohort. (FIG. 6C) A significance plot of the correlation between the spTMS/EEG responses and rsEEG phenotype, as indexed by the leave-one-out cross-validated Pearson's correlation coefficients between the SELSER-predicted rsEEG phenotype and true rsEEG phenotype, for each of the stimulation sites. The SELSER analysis was performed separately for the same set of frequency bands as used in the rsEEG prediction analysis ($\theta$: theta, $\alpha$: alpha, $\beta$: beta, $\gamma$: gamma), and for three time windows relative to the TMS pulse (0-200 ms, 200-400 ms, 400-600 ms), followed by a false discovery rate correction (FDR) across all of these tests. Only right aDLPFC stimulation (alpha band, 200-400 ms: r=0.60, p=$5.5\times10^{-4}$), left pDLPFC stimulation (gamma band, 200-400 ms: r=0.58, p=$8\times10^{-4}$) and right pDLPFC stimulation (beta band, 0-200 ms: r=0.60, p=$4.6\times10^{-4}$) survived FDR correction (denoted by asterisks). The plot shows −log 10(p) of the correlation of the SELSER-predicted rsEEG phenotype with true rsEEG phenotype.

(FIG. 11A) 1.5 minutes/block. (FIG. 11B) 1 minute/block. (FIG. 11C) 30 seconds/block.

(FIG. 12A) Block 1. (FIG. 12B) Block 2. (FIG. 12C) Block 1 vs. 2.

(FIG. 13A, FIG. 13C) Spatial patterns of the SELSER latent signals for the resting eyes open (REO) condition, with the most positive ($\beta$=556.50.31; left) and negative ($\beta$=−773.49; right) regression weights, respectively. (FIG. 13B, FIG. 13D) Spatial patterns of the SELSER latent signals for the resting eyes closed (REC) condition, with the most positive ($\beta$=840.85; left) and negative ($\beta$=−801.23; right) regression weights, respectively.

(FIG. 15A) Treatment prediction when site effect was not accounted for. (FIG. 15B) Comparison of root mean square error (RMSE) without and with site correction.

(FIG. 16A) End-to-end prediction with SELSER. All the unknown parameters (spatial filters and linear regression weight coefficients) are optimized in conjunction under a unified objective function via convex optimization. (FIG. 16B) Prediction with ICA/PCA. Spatial filters are optimized via ICA/PCA, and linear regression weight coefficients are optimized via RVM with a linear kernel. (FIG. 16C) Prediction with channel-level band power. EEG band power of each channel is fed directly into the linear regression model, which is optimized via RVM with a linear kernel. S1, S2, and SN refer to Subject 1, Subject 2, and the Nth Subject, respectively. C1, C2, F1, F2 and Pz refer to electrode locations according to the 10/10 international system. $(\cdot)^2$ denotes the square operator, and $ft$ denotes the average of a time series over time. (FIG. 16D) Identification of clinically relevant clusters including clusters representative of different diseases and/or disease subtypes. Clustering (e.g., k-means, Gaussian mixture, and/or the like) is performed on low-dimensional latent signals generated by applying optimal spatial filters to a subject's EEG. Application of the optimized spatial filters generates latent signals whose band powers are most predictive of treatment outcome. These latent signals provide a better representation of the EEG in relation to the treatment outcome.

(FIG. 17A) Sertraline arm. (FIG. 17B) Placebo arm FIG. 18. Prediction of outcome specific to sertraline using SELSER trained on resting eyes open alpha-frequency range data of posterior channels. A total of 16 posterior electrodes were included: P1, P2, P3, P4, P5, P6, P7, P8, PO3, PO4, PO7, PO8, POz, O1, O2, and Oz. Prediction performance was assessed with 10×10 stratified cross-validation prediction. The most positive regression weight is 759.31 and the most negative regression weight is −853.13.

FIG. 20 depicts a flowchart illustrating an example of a process for machine learning based EEG data processing, in accordance with some example embodiments; and FIG. 21 depicts a block diagram illustrating a computing system, in accordance with some example embodiments.

DETAILED DESCRIPTION

Definitions

Figure 1:
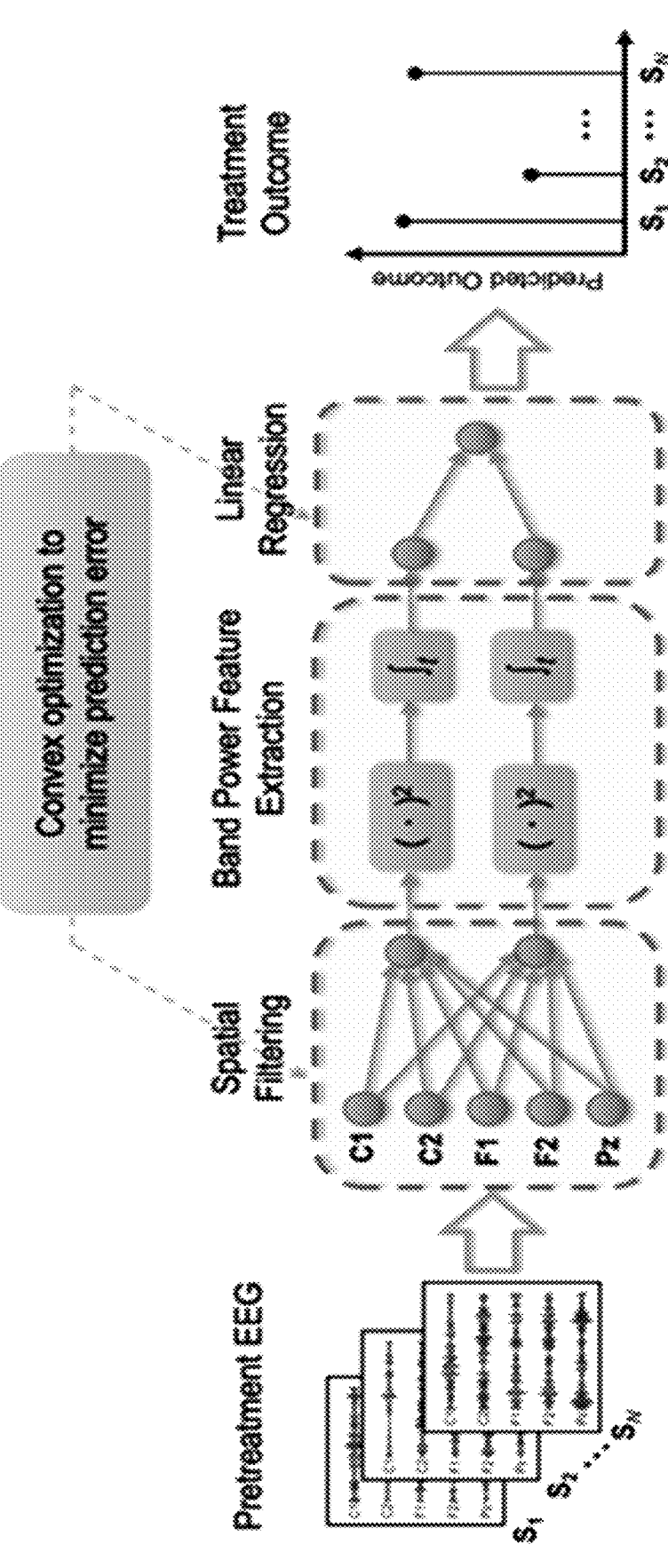
FIG. 1. End-to-end prediction of the treatment outcome with a latent space model. The model consists of three stages: 1) Spatial filtering that linearly transforms the EEG signals to the latent signals; 2) Band power feature extraction that computes the band power of each latent signal; 3) Linear regression that uses the band powers to predict the treatment outcome. By solving a convex optimization problem, all the unknown parameters (spatial filters and linear regression weight coefficients) are optimized in conjunction under a unified objective function that trades off between the prediction error and dimensionality of the latent signals. S1, S2, and SN refer to Subject 1, Subject 2, and the Nth Subject, respectively. C1, C2, F1, F2 and Pz refer to electrode locations according to the 10/10 international system. $(\cdot)^2$ denotes the square operator, and $\int t$ denotes the average of a time series over time.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "brain region(s)" is used according to its plain and ordinary meaning and refers to a brain anatomical region following standard neuroanatomy hierarchies (e.g. a functional, connective or developmental region). Exemplary brain regions include, but are not limited to, brainstem, medulla oblongata, medullary pyramids, olivary body, inferior olivary nucleus, Rostral ventrolateral medulla, Respiratory center, Dorsal respiratory group, Ventral respiratory group, Pre-Botzinger complex, Botzinger complex, Paramedian reticular nucleus, Cuneate nucleus, Gracile nucleus, Intercalated nucleus, Area postrema, Medullary cranial nerve nuclei, Inferior salivatory nucleus, Nucleus ambiguus, Dorsal nucleus of vagus nerve, Hypoglossal nucleus, Solitary nucleus, Pons, Pontine nuclei, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, Tectum, Corpora quadrigemina, inferior colliculi, superior colliculi, Pretectum, Tegmentum, Periaqueductal gray, Parabrachial area, Medial parabrachial nucleus, Lateral parabrachial nucleus, Subparabrachial nucleus (Kölliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), Pineal body, Habenular nucleim Stria medullares, Taenia thalami, Subcommissural organ, Thalamus, Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, Hypothalamus, limbic system, HPA axis, preoptic area, Medial preoptic nucleus, Suprachiasmatic nucleus, Paraventricular nucleus, Supraoptic nucleusm Anterior hypothalamic nucleus, Lateral preoptic nucleus, median preoptic nucleus, periventricular preoptic nucleus, Tuberal, Dorsomedial hypothalamic nucleus, Ventromedial nucleus, Arcuate nucleus, Lateral area, Tuberal part of Lateral nucleus, Lateral tuberal nuclei, Mammillary nuclei, Posterior nucleus, Lateral area, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, Subthalamus, Subthalamic nucleus, Zona incerta, Pituitary gland, neurohypophysis, Pars intermedia, adenohypophysis, cerebral hemispheres, Corona radiata, Internal capsule, External capsule, Extreme capsule, Arcuate fasciculus, Uncinate fasciculus, Perforant Path, Hippocampus, Dentate gyrus, Cornu ammonis, Cornu ammonis area 1, Cornu ammonis area 2, Cornu ammonis area 3, Cornu ammonis area 4, Amygdala, Central nucleus, Medial nucleus (accessory olfactory system), Cortical and basomedial nuclei, Lateral and basolateral nuclei, extended amygdala, Stria terminalis, Bed nucleus of the stria terminalis, Claustrum, Basal ganglia, Striatum, Dorsal striatum (aka neostriatum), Putamen, Caudate nucleus, Ventral striatum, Striatum, Nucleus accumbens, Olfactory tubercle, Globus pallidus, Subthalamic nucleus, Basal forebrain, Anterior perforated substance, Substantia innominata, Nucleus basalis, Diagonal band of Broca, Septal nuclei, Medial septal nuclei, Lamina terminalis, Vascular organ of lamina terminalis, Olfactory bulb, Piriform cortex, Anterior olfactory nucleus, Olfactory tract, Anterior commissure, Uncus, Cerebral cortex, Frontal lobe, Frontal cortex, Primary motor cortex, Supplementary motor cortex, Premotor cortex, Prefrontal cortex, frontopolar cortex, Orbitofrontal cortex, Dorsolateral prefrontal cortex, dorsomedial prefrontal cortex, ventrolateral prefrontal cortex, lateral prefrontal cortex, Superior frontal gyrus, Middle frontal gyrus, Inferior frontal gyrus, Brodmann areas: 4, 6, 8, 9, 10, 11, 12, 24, 25, 32, 33, 44, 45, 46, 47, Parietal lobe, Parietal cortex, Primary somatosensory cortex (S1), Secondary somatosensory cortex (S2), Posterior parietal cortex, postcentral gyrus, precuneus, Brodmann areas 1, 2, 3 (Primary somesthetic area); 5, 7, 23, 26, 29, 31, 39, 40, Occipital lobe, Primary visual cortex (V1), V2, V3, V4, V5/MT, Lateral occipital gyrus, Cuneus, Brodmann areas 17 (V1, primary visual cortex); 18, 19, temporal lobe, Primary auditory cortex (A1), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas: 9, 20, 21, 22, 27, 34, 35, 36, 37, 38, 41, 42, Medial superior temporal area (MST), insular cortex, anterior insula, cingulate cortex, Anterior cingulate, dorsal anterior cingulate cortex, Posterior cingulate, dorsal cingulate, Retrosplenial cortex, Indusium griseum, Subgenual area 25, Brodmann areas 23, 24; 26, 29, 30 (retrosplenial areas); 31, 32, cranial nerves (Olfactory (I), Optic (II), Oculomotor (III), Trochlear (IV), Trigeminal (V), Abducens (VI), Facial (VII), Vestibulocochlear (VIII), Glossopharyngeal (IX), Vagus (X), Accessory (XI), Hypoglossal (XII)), and neural pathways Superior longitudinal fasciculus, Arcuate fasciculus, Thalamocortical radiations, Cerebral peduncle, Corpus callosum, Posterior commissure, Pyramidal or corticospinal tract, Medial longitudinal fasciculus, dopamine system, Mesocortical pathway, Mesolimbic pathway, Nigrostriatal pathway, Tuberoinfundibular pathway, serotonin system, Norepinephrine Pathways, Posterior column-medial lemniscus pathway, Spinothalamic tract, Lateral spinothalamic tract, Anterior spinothalamic tract. Brain regions and specific parts of brain regions may be referred to according to their rostral/caudal, dorsal/ventral, medial/lateral, and/or anterior/posterior positions within the brain region with respect to the skull. In certain circumstances, brain regions may be generally referred to as cortical or subcortical brain regions depending on whether they form part of the cerebral cortex (e.g., part of the frontal, parietal, temporal, or occipital lobes) or are regions located below the cerebral cortex (e.g., basal ganglia, thalamus, internal capsule, brainstem, and cerebellum).

The term "brain region connectivity", "functional brain region connectivity", "brain circuit", "brain (or neural) connection", "brain network" or the like refers to a plurality of brain regions having neural activity (e.g., quantifiable brain activity levels) correlated with each other. For example, connectivity may be established where brain regions are active simultaneously, approximately simultaneous, or close in time (e.g. within a minute, an hour or three hours) in response to a stimulus or activity.

As used herein, the term "brain activity level" refers to measurable (e.g., quantifiable) neural activity. Measurable neural activity includes, but is not limited to, a magnitude of activity, a frequency of activity, a delay of activity, or a duration of activity. Brain activity levels may be measured (e.g., quantified) during periods in which no stimulus is presented. In embodiments, the brain activity level measured in the absence of a stimulus is referred to as a baseline brain activity level. Alternatively, brain activity levels may be measured (e.g., quantified) when one or more stimuli are delivered (e.g., an emotional conflict task). In embodiments, the brain activity level measured in the presence of a stimulus is referred to as a brain activity level response. Brain activity levels may be measured simultaneously or sequentially throughout the whole brain, or restricted to specific brain regions (e.g., frontopolar cortex, lateral pre-frontal cortex, dorsal anterior cingulate, anterior insula). In embodiments, the brain activity level is determined relative to a baseline brain activity level taken during a baseline period. The baseline period is typically a period during which a stimulus is not presented or has not been presented for a sufficient amount of time (e.g., great than at least 0.05, 0.1, 0.15, 0.25, 0.5, 1, 2, 3, 4, 5, 10, 15, 30, 60 seconds or more).

A brain activity level may also encompass evaluating functional brain region connectivity. For example, neural activity recorded in a plurality of brain regions may have a specific time course across brain regions that can be correlated to reveal a functional brain connectivity pattern (e.g., at a first time point a first brain regions shows an increase in neural activity and at a second time point a second brain region shows an increase in activity). Methods for relating or correlating brain region activity levels across time to identify functional brain region connectivity may be found, for example, described in Example 3. Thus, in embodiments, a brain activity level is a measurement (e.g., quantification) of a time course of neural activity across a plurality of brain regions. In embodiments, a brain activity level is a sequence of brain region activity levels measured (e.g., quantified) across different brain regions over time. In embodiments, a brain activity level is a functional brain region connectivity pattern.

It is contemplated that any suitable method of measuring brain activity levels (e.g., neural activity) including, but not limited to, EEG, MEG, fMRI, and fNIRS may be used for practicing the methods described herein, including embodiments thereof.

In embodiments, a measured brain activity level is a magnitude of neural activity. In embodiments, a measured brain activity level is a magnitude of neural activity measured at 25-50 msecs, 100-150 msecs, or 180 and 200 msecs following delivery of a stimulus (e.g., emotional conflict task trial). The magnitude can be measured between 25-50 msecs (p30), 30-70 msecs (p60), 70-120 msecs (n100), 150-250 msecs (p200). Alternatively, the frequency of the brain activity level can be measured. In embodiments, the brain activity level may have a frequency of, for example, delta (0.5-4 Hz), theta (5-8 Hz), alpha (8-12 Hz), beta (12-30 Hz), or gamma (30-60 Hz). Similarly, the brain activity level can be measured by detecting the amplitude (e.g., power) of oscillations at delta (0.5-4 Hz), theta (5-8 Hz), alpha (8-12 Hz), beta (12-30 Hz), or gamma (30-60 Hz) frequencies. In embodiments, the brain activity level frequency, amplitude (e.g., power), and phase can be measured. In embodiments, a duration of the brain activity level is measured. In embodiments, a presence or absence of a brain activity level is measured. In embodiments, a brain activity level may be an average brain activity level. In embodiments, a brain activity level may be a median brain activity level.

In embodiments, a brain activity level is an electrical potential or magnetic field recorded from the nervous system, e.g. brain, of a human or other animal, following presentation of a stimulus (e.g., a trial in an emotional conflict task) that is distinct from spontaneous potentials or fields as detected by electroencephalography (EEG), magnetoencephalography (MEG), or other electrophysiological or neurophysiological recording methods. Such potentials and fields are useful for monitoring brain function in health and disease, and, as described herein, may be used for prognostic purposes. The recorded electrical potential or magnetic field is often presented with an amplitude, phase and/or frequency, including the amplitude or power of the response frequency, which generally indicates an intensity and/or pattern of the response.

As used herein, the term "electroencephalography (EEG)" refers to a non-invasive neurophysiological technique that uses an electronic monitoring device to measure and record electrical activity in the brain.

EEG is typically described in terms of rhythmic activity, and the rhythmic activity is divided into bands by frequency. The band designations arose because rhythmic activity within a certain frequency range was noted to have a certain distribution over the scalp or a certain biological significance. Waveforms are subdivided into bandwidths known as alpha, beta, theta, and delta, to signify the majority of EEG used in clinical practice. Delta is the frequency range up to 4 Hz, and it tends to be the highest in amplitude and the slowest waves. Delta is seen normally in adults in slow-wave sleep, and it is also seen normally in babies. Theta is the frequency range from 4 Hz to 7 Hz, and it is seen normally in young children. Theta may be seen in drowsiness or arousal in older children and adults. Alpha is the frequency range from 7 Hz to 13 Hz. Alpha is the "posterior basic rhythm" (also called the "posterior dominant rhythm" or the "posterior alpha rhythm"), seen in the posterior regions of the head on both sides, higher in amplitude on the dominant side. Alpha emerges with closing of the eyes and with relaxation, and attenuates with eye opening or mental exertion. Beta is the frequency range from 14 Hz to about 30 Hz, and it is seen usually on both sides in symmetrical distribution and is most evident frontally. Beta activity is closely linked to motor behavior and is generally attenuated during active movements. Beta is the dominant rhythm in patients who are alert or anxious or who have their eyes open.

The signaling in a biological neural network is based on a highly coordinated system of electric charges, neurotransmitters and action potentials. The ability to reliably and non-invasively incite and monitor neuronal activity changes from outside the head with the purpose of modulating activity in specific neural networks remains a roadblock to enable advances in the detection, monitoring, and treatment of psychiatric, neurological and related conditions. A neural network can be considered as a complex electrical circuit made of many neurons connected through synapses formed between axons and dendrites. Both types of synapses, known as chemical and electrical synapses, respectively, transfer information between adjacent axons and dendrites directly or indirectly through electric field energy. Consequently, the neural network is sensitive to external electric fields. Existing non-invasive brain stimulation methods include transcranial magnetic stimulation (TMS), transcranial direct current stimulation (tDCS) and transcranial alternating current stimulation (tACS).

Non-invasive brain stimulation locally alters brain electrical signaling. These local alterations in signaling can result in broader alterations to neuronal signaling throughout the brain. These circuit-wide effects of non-invasive brain stimulation reflect the brain effects of stimulation as well as the network rebound response to a burst of activity entering the system. This set of events is referred to herein as a non-invasive brain stimulation evoked response (e.g., a TMS evoked response).

In embodiments, a magnitude of a non-invasive brain stimulation evoked response is measured at 25-50 msecs, 100-150 msecs, or 180 and 200 msec following non-invasive brain stimulation. The TMS evoked response can be measured between 25-50 msecs (p30), 30-70 msecs (p60), 70-120 msecs (n100), 150-250 msecs (p200). Alternatively, the TMS evoked response can be measured on the amplitude of oscillations at theta (5-8 Hz), alpha (8-12 Hz), beta (12-30 Hz), or gamma (30-60 Hz) within the first second after a TMS pulse.

In embodiments, an evoked response is an electrical potential recorded from the nervous system, e.g. brain, of a human or other animal following presentation of a stimulus, as distinct from spontaneous potentials as detected by electroencephalography (EEG), electromyography (EMG), or other electrophysiologic recording method. Such potentials are useful for electrodiagnosis and monitoring. The recorded electrical potential is often presented with an amplitude, phase and/or frequency which generally indicates an intensity and/or patent of the response.

As used herein, the term "magnetoencephalography (MEG)" refers to a non-invasive neurophysiological technique that measures the magnetic fields generated by neuronal activity of the brain. The spatial distributions of the magnetic fields are analyzed to localize the sources of the activity within the brain.

As used herein, the terms "functional magnetic resonance imaging (fMRI)" or "functional MRI (fMRI)" refer to a functional neuroimaging procedure using MRI technology that measures neural activity by detecting changes associated with blood flow.

As used herein, the term "functional near-infrared spectroscopy (fNIRS)" refers to a functional spectroscopic method that uses the near-infrared region of the electromagnetic spectrum (from about 700 nm to 2500 nm). For example, fNIRS can be used for non-invasive assessment of neural activity through the intact skull in human subjects by detecting changes in blood hemoglobin concentrations associated with neural activity.

It should be appreciated that brain activity levels measured in a subject may be compared to brain activity levels measured at a different time point (e.g., in response to different stimuli, an intervention (e.g. medication) or passage of time) in the same subject; to brain activity levels measured in a different subject, wherein the different subject suffers from the same psychiatric disorder (e.g., depression, major depression); or to a brain activity levels measured in a control subject (e.g., healthy control).

It is also contemplated that brain activity levels, as measured according to embodiments herein, may be classified (e.g., identified) as, for example, a brain activity level indicative of a subject being amendable to treatment (e.g., a depressed subject being responsive to treatment with an antidepressant). This type of classification (e.g., identification) may be useful, for example, to determine treatment outcome. Classification may be carried out by, for example, visual inspection and quantification performed by a human operator. Alternatively, classification may be accomplished via human operator-independent means. For example, classification may be accomplished through a computer running a machine learning model (e.g., algorithm) capable of classifying (e.g., identifying) a brain activity level indicative of a subject being amendable to treatment (e.g., a depressed subject being responsive to treatment with an antidepressant). The machine learning model may be any suitable machine learning model or algorithm known in the art. In embodiments, the model may be trained, for example using training data, to classify (e.g., identify) a subject being amendable to treatment (e.g., a depressed subject being responsive to treatment with an antidepressant). Training of the algorithm may be accomplished through supervised or unsupervised training methods.

A "subject" as used herein refers to an organism. In certain embodiments, the organism is an animal. In certain embodiments, the subject is a living organism. In certain embodiments, the subject is a cadaver organism. In certain embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient. In embodiments, the subject suffers from a psychiatric disorder. In embodiments, the subject suffers from depression. In embodiments, the subject has not been diagnosed with a psychiatric disorder. In embodiments, the subject is suspected of suffering from a psychiatric disorder. In embodiments, the psychiatric disorder is depression. In embodiments, the psychiatric disorder is major depression. In embodiments, the subject is suspected of suffering from depression. In embodiments, the subject suffers from depression. In embodiments, the subject is suspected of suffering from major depression. In embodiments, the subject suffers from major depression. In embodiments, the subject's primary diagnosis is depression. In embodiments, the subject's primary diagnosis is major depression. In embodiments, the subject does not have a lifetime history of psychosis. In embodiments, the subject does not suffer from posttraumatic stress disorder (PTSD). In embodiments, the subject does not suffer from bipolar disorder. In embodiments, the subject does not suffer from addiction or substance abuse. In embodiments, the subject does not have epilepsy. In embodiments, the subject does not have a comorbidity. In embodiments, the subject has a comorbidity. In embodiments, the comorbidity is anxiety. In embodiments, the comorbidity is social anxiety. In embodiments, the comorbidity is panic disorder. In embodiments, the comorbidity is generalized anxiety disorder (GAD). In embodiments, the comorbidity is not psychosis. In embodiments, the comorbidity is not PTSD. In embodiments, the comorbidity is not bipolar disorder. In embodiments, the comorbidity is not addiction or substance abuse. In embodiments, the comorbidity is not epilepsy.

The term "emotional conflict task" as used herein refers to the well-characterized paradigm that assesses emotional conflict and emotional conflict regulation. The emotional conflict task involves a series of trials (e.g., 5, 10, 15, 20, 30, 40, 50, 75, 100, 150, 200, 250, 300, or more trials) where each trial includes an emotional face overlaid with an emotion word. These trials are presented visually to the subject and the subject must identify the facial emotion. Identification may be performed, for example, via a key press. Trials may be "congruent trials," where the emotional face is overlaid with an emotion word that matches the emotional face or "incongruent trials," where the emotional face is overlaid with an emotion word that does not match the emotional face. For example, a congruent trial may have a face with a happy expression shown with the word "HAPPY" overlaid. An incongruent trial, on the other hand, may have a face with a happy expression shown with the word "FEAR" overlaid. Congruent and incongruent trials may be delivered randomly or pseudo-randomly, such that congruent trials may follow incongruent trials, congruent trials may follow congruent trials, incongruent trials may follow congruent trials, incongruent trials may follow incongruent trials, etc.

"Treating" or "treatment" as used herein (and as well-understood in the art) broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease or disorder (e.g., psychiatric disorder (e.g., depression, major depression)). Treatment may prevent the disease or disorder from occurring; relieve the disease's or disorder's symptoms (e.g., depression), fully or partially remove the disease's or disorder's underlying cause, shorten a disease's or disorder's duration, or do a combination of these things.

The term "transcranial magnetic stimulation" or "TMS" as used herein refers to a non-invasive brain stimulation method which employs a magnetic field generator applied near the head to locally stimulate an electrical current within the brain. In embodiments, TMS includes repetitive transcranial magnetic stimulation or rTMS. Treatment with rTMS is comprised of multiple sessions (either daily across days or multiple times per day and across days) wherein TMS is delivered repetitively in a pattern that is intended to induce plasticity (defined as a change in brain activity). This plasticity could increase or decrease the activity of the brain region that is targeted. In embodiments, the rTMS is a "high frequency" protocol, involving stimulation at >5 Hz. In embodiments the rTMS is a "high frequency" protocol, involving stimulation at ≤1 Hz. In embodiments the rTMS is a "theta burst" protocol, involving stimulation with either a continuous or intermittent theta burst pattern. In embodiments, the rTMS provides a protocol involving stimulations at any value from or at about 1 Hz to about 5 Hz. In embodiments, the rTMS provides a protocol involving stimulations having more than one frequency.

TMS is a non-invasive technique that typically involves placing a coil near the patient's head to depolarize or hyperpolarize neurons of the brain. In particular, TMS uses electromagnetic induction to induce neuronal electrical currents using a rapidly changing magnetic field. A changing magnetic field leads to changing electrical currents by causing transient shifts in ions across neuron cell membranes. The brain region underneath the TMS coil is the primary target for the TMS effect, with further distant areas of the brain being impacted through the initial impulse delivered to the targeted region under the coil. TMS techniques typically act on a volume of brain tissue that is approximately two to three centimeters in diameter. TMS methods can include repetitive TMS (rTMS), single pulse TMS (spTMS), or paired pulse TMS (ppTMS).

The term "frequency" in the context of TMS may refer to a rate at which one pulse of TMS occurs or is repeated over a particular period of time. For example, a frequency of TMS can vary, e.g. from about 1 to about 30 Hz or more. In some examples, a frequency of TMS may vary over a course of time so that a frequency of TMS at an early stage of treatment may be increased or decreased as the treatment continues. In some other examples, a frequency of TMS may substantially remain unchanged throughout a course of treatment.

The term "intensity" or "power" in the context of TMS may refer to an extent of an energy transferred per unit area. For example, a frequency of TMS can vary, e.g. from about 0.25 Hz to 100 Hz or more. In some examples, the intensity or power of TMS may vary over a course of time so that the intensity or power of TMS at an early stage of treatment may be increased or decreased as the treatment continues. In some other examples, the intensity or power of TMS may substantially remain unchanged throughout a course of treatment.

The term "duration" in the context of TMS may refer to a period of time which TMS continues per one protocol or a course of treatment. One or more number of TMS can be administered to a subject in duration from about a few seconds to about a minute, about a few minutes to about an hour, about one or more hours, about one day to several days, about one week to several weeks, about one month to several months or longer.

The term "waveform" in the context of TMS may refer to a curve showing the shape of a wave (or TMS pulse) at a given time. Some examples of TMS waveform include, but not limited to monophasic and biphasic. A waveform of TMS can vary or substantially remain unchanged throughout a course of treatment.

The term "pattern" in the context of TMS may refer to the temporal sequence of stimulation. Some examples of TMS pattern include, but not limited to fixed patterns at 1 Hz, clusters of stimuli at 10 Hz separated by a rest period, or theta burst, A pattern of TMS can vary or substantially remain unchanged throughout a course of treatment.

The terms "site" or "TMS site" in the context of TMS may refer to a location or area, relative to the head of a subject, where a stimulation is administered to the subject. In some examples where TMS is administered by placing a coil on the subject's head and TMS is generated by and administered from the coil, the site may include the location or area where the coil is placed as well as an angle of the coli relative to the head of the subject. In some examples, a site of TMS, e.g. a location and/or angle of a coil individually or in combination may vary over a course of time. In some other examples, the site of TMS, e.g. the location and/or angle of coil individually or in combination may substantially remain unchanged throughout a course of treatment.

In an example treatment protocol, daily rTMS induces long-lasting cortical neuromodulatory effects across broadly distributed regions. These effects are temporally and spatially removed from the onset and location of stimulation, but are highly predictive of clinical outcome. Mechanistically, non-invasive and invasive studies suggest that rTMS induces a reduction in early, local evoked gamma power and an early excitatory electrophysiological response, and an increase in later alpha power and slower inhibitory electrophysiological responses, suggesting a lasting alteration in the excitability of brain networks and altered interaction between brain regions and networks.

Treatment protocols for each type of TMS vary in duration, time course, pulse sequence, magnitude of stimulation and area of stimulation. Course of treatment can vary in duration from about one day, two days, three days, four days, five days, six days, seven days, one week, two weeks, three weeks, four weeks, five weeks, six weeks, seven weeks, eight weeks, or more. Frequency of TMS stimulation can vary (e.g., about 10, 20, or 30 Hz). TMS stimulation can be 1 Hz TMS, 3 Hz TMS, 5 Hz TMS, 7 Hz TMS, 10 Hz TMS, 15 Hz TMS, 20 Hz TMS, 25 Hz TMS, 30 Hz TMS or intermittent theta burst TMS. Paired pulse TMS can be administered at a time offset of about 10 milliseconds (msecs or ms), 20 msecs, 30 msecs, 40 msecs, 50 msecs, 100 msecs, 150 msecs, 200 msecs, 250 msecs, 300 msecs, or more. In embodiments, TMS can be administered to the right or left prefrontal cortices (e.g., left dorsolateral prefrontal cortex (DLPFC), right DLPFC, dorsal cingulate, dorsomedial prefrontal cortex, frontopolar cortex, ventrolateral prefrontal cortex.)

It is contemplated herein that treatment may occur through administration of administration of a medication. In embodiments, the medication is an antidepressant. In embodiments the antidepressant is a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, or an over-the-counter antidepressant.

The terms "selective serotonin reuptake inhibitor" or "SSRI" as used herein refer to a class of drugs that are typically used as antidepressants in the treatment of depression (e.g., depression, major depression) and anxiety disorders. The specific action of SSRIs is unknown but they are believed to increase the extracellular level of serotonin by limiting reuptake of serotonin. Non-limiting examples of SSRIs include citalopram, escitalopram, fluoxetine, fluvoxamine, paroxetine, and sertraline.

The terms "serotonin and norepinephrine reuptake inhibitor" or "SNRI" as used herein refer to a class of antidepressants used to treat depression (e.g., depression, major depression). SNRIs are monoamine reuptake inhibitors; that specifically inhibit reuptake of serotonin and norepinephrine. Non-limiting examples of SNRIs include desvenlafaxine, duloxetine, levomilnacipran, milnacipran, and venlafaxine.

The terms "monoamine oxidase inhibitor" or "MAOI" as used herein refer to a class of drugs used for treating depression (e.g., depression, major depression). Monoamine oxidase inhibitors inhibit the activity of one or both monoamine oxidase enzymes: monoamine oxidase A and monoamine oxidase B. Non-limiting examples of MAOIs include isocarboxazid, nialamide, phenelzine, hydracarbazine, tranylcypromine, bifemelane, moclobemide, pirlindole, toloxatone, rasagiline, selegilin, caroxazone, and safinamide.

The terms "tricyclic antidepressant" or "TCA" as used herein refer to a class of medication used to primarily treat depression (e.g., depression, major depression). TCAs typically act by preventing the reuptake of serotonin and/or norepinephrine. Non-limiting examples of tricyclic antidepressants include amitriptyline, amitriptylinoxide, clomipramine, desipramine, dibenzepin, dimetacrine, dosulepin, doxepin, imipramine, lofepramine, melitracen, nitroxazepine, nortriptyline, noxiptiline, opipramol, pipofezine, protriptyline, and trimipramine.

The terms "serotonin modulator and stimulator" or "SMS" as used herein refer to a type of drug with a multimodal action specific to the serotonin neurotransmitter system, SMSs may simultaneously modulate one or more serotonin receptors and inhibit the reuptake of serotonin. Non-limiting examples of SMSs include vilazodone and vortioxetine.

The terms "norepinephrine reuptake inhibitor" or "NRI" as used herein refer to a type of drug that acts as a reuptake inhibitor for the neurotransmitters norepinephrine (noradrenaline) and epinephrine (adrenaline) by blocking the action of the norepinephrine transporter (NET). Non-limiting examples of NRIs include reboxetine, teniloxazine, viloxazine, and atomoxetine.

The terms "norepinephrine-dopamine reuptake inhibitor" or "NDRI" as used herein refer to a type of drug that acts as a reuptake inhibitor for the neurotransmitters norepinephrine and dopamine by blocking the action of the norepinephrine transporter (NET) and the dopamine transporter (DAT), respectively. Non-limiting examples of NDRIs include bupropion, amineptine, methylphenidate, and lisdexamfetamine.

The terms "serotonin antagonist and reuptake inhibitor" or "SARI" as used herein refer to a type of drug that acts to antagonize serotonin receptors such as $5\text{-HT}_{2A}$ and inhibit the reuptake of serotonin, norepinephrine, and/or dopamine. Some SARIs may additionally antagonize $\alpha_1$-adrenergic receptors. Non-limiting examples of SARIs include nefazodone and trazodone.

The terms "tetracyclic antidepressant" or "TeCA" as used herein refer to a class of antidepressants having a tetracyclic chemical structure. Non-limiting examples of TeCAs include amoxapine, maprotiline, mianserin, mirtazapine, and setiptiline.

The term "atypical antipsychotic" as used herein refers to a group of drugs used to treat psychiatric conditions including, but not limited to, bipolar disorder and depression (e.g., major depressive disorder). Non-limiting examples of atypical antipsychotics include amisulpride, lurasidone, and quetiapine.

The term "alternative antidepressant" as used herein refers to a group of drugs that do not fall under a class as described herein, but are useful for the treatment of depression. Non-limiting examples of alternative antidepressants include agomelatine, ketamine, tandospirone, tianeptine, and minocycline.

The term "over-the-counter antidepressant" as used herein refers to a group of drugs useful for the treatment of depression that can be obtained with a prescription or without. Non-limiting examples of over-the-counter antidepressants include ademetionine, *Hypericum perforatum*, oxitriptan, rubidium chloride, and tryptophan.

It is further contemplated that the types of antidepressants described herein may be used in combination with one another or with an adjunct. Non-limiting examples of combination treatments include amitriptyline/perphenazine, flupentixol/melitracen, olanzapine/fluoxetine, and tranylcypromine/trifluoperazine. Non-limiting examples of adjuncts include aripiprazole, brexpiprazole, lurasidone, olanzapine, quetiapine, risperidone, buspirone, lithium, thyroxine ($T_4$), and triiodothyronine ($T_3$).

A list of antidepressants may be found in Lancet (2018) Feb. 20. pii: S0140-6736(17)32802-7. doi: 10.1016/S0140-6736(17)32802-7, which is incorporated herein by reference in its entirety.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. In embodiments, antidepressants are administered orally.

Administering may also be used in connection with an emotional conflict task. In these circumstances, administering refers to administering an emotional conflict task as described herein, including embodiments thereof, to a subject. In embodiments, the administration of the conflict task includes visual delivery of emotional conflict trials. In embodiments, visual delivery is accomplished via a screen or monitor.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease or disorder, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Pickar, Dosage Cal-*

*culations* (1999); and *Remington: The Science and Practice of Pharmacy,* 20th Edition, 2003, Gennaro, Ed., Lippincott, Williams & Wilkins).

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

To determine efficacy of treatment in psychiatric disorders (e.g., depression, major depression) questionnaires (e.g., self-reporting questionnaires) may be used. Non-limiting examples of questionnaires useful for assessing treatment efficacy in psychiatric disorders (e.g., depression, major depression) include the Hamilton Rating Scale for Depression; the Hamilton Rating Scale for Depression 17 item $(HAMD_{17}$ or HAMD-17); the 21 item HAMD $(HAMD_{21})$; the 24 item HAMD $(HAMD_{24})$; the Quick Inventory of Depressive Symptoms (QIDS); the Mood and Symptom Questionnaire subscale scores for Anxious Arousal, Anhedonic Depression, and General Distress; the Montgomery-Asberg Depression Scale (MADRS); the Beck Depression Inventory; the Clinical Global Impressions (GCI) scale); the Snaith-Hamilton Pleasure Scale (SHAPS). Questionnaires may be completed prior to, during, and following treatment, and changes in the scores may be used to determine treatment efficacy. In embodiments, the $HAMD_{17}$ is used to determine treatment efficacy. In embodiments, the HAMD is used to determine treatment efficacy. In embodiments, the $HAMD_{21}$ is used to determine treatment efficacy. In embodiments, the $HAMD_{24}$ is used to determine treatment efficacy. In embodiments, the QIDS is used to determine treatment efficacy. In embodiments, the Mood and Symptom Questionnaire subscale scores for Anxious Arousal, Anhedonic Depression, and General Distress is used to determine treatment efficacy. In embodiments, the MADRS is used to determine treatment efficacy. In embodiments, the Beck Depression Inventory is used to determine treatment efficacy. In embodiments, the GCI scale is used to determine treatment efficacy. In embodiments, treatment efficacy is determined by measuring (e.g., quantifying) a change in the $HAMD_{17}$ score. In embodiments, treatment efficacy is determined by measuring (e.g., quantifying) a change in the $HAMD_{21}$ score. In embodiments, treatment efficacy is determined by measuring (e.g., quantifying) a change in the HAMD score. In embodiments, treatment efficacy is determined by measuring (e.g., quantifying) a change in the $HAMD_{24}$ score. In embodiments, treatment efficacy is determined by measuring (e.g., quantifying) a change in the QIDS score. In embodiments, treatment efficacy is determined by measuring (e.g., quantifying) a change in the Mood and Symptom Questionnaire subscale scores for Anxious Arousal, Anhedonic Depression, and General Distress.

In embodiments, treatment efficacy is determined by measuring (e.g., quantifying) a change in the MADRS score. In embodiments, treatment efficacy is determined by measuring (e.g., quantifying) a change in the Beck Depression Inventory score. In embodiments, treatment efficacy is determined by measuring (e.g., quantifying) a change in the GCI scale. In embodiments, treatment efficacy is determined by measuring (e.g., quantifying) a score on a questionnaire as described herein during a baseline period prior to treatment to a score on a questionnaire as described herein reported 1, 2, 3, 4, 6, 8 or more weeks after commencing treatment or terminating treatment.

Treatment may result in a reduction of symptoms (e.g., a response) or in remission. In embodiments, a reduction in symptoms is referred to as a response. In embodiments, a response is a 50% or greater decrease in symptoms. A response (e.g., a 50% or greater decrease in symptoms) to treatment may be determined by measuring (e.g., quantifying) a change in a score as described herein, including embodiments thereof, on a questionnaire as described herein, including embodiments thereof. In embodiments, remission is a score of 7 or less at endpoint on the $HAMD_1$. In embodiments, remission is a score of 7 or less at endpoint on the HAMD. In embodiments, remission is a score of 10 or less on the $HAMD_{24}$. In embodiments, remission is a score of 5 or less on the QIDS. In embodiments, remission is a score of 9 or less on the MADRS.

Methods

Provided herein are, inter alia, methods for determining whether a subject suffering from depression will respond to treatment with an antidepressant. Further, the methods provided herein are useful for determining whether a subject will benefit specifically from treatment with an antidepressant over a placebo.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1: Antidepressant-Responsive Brain Signature in Major Depression Defined by Electroencephalography Though antidepressants are some of the most-widely prescribed medications, their efficacy relative to placebo has come into question. One reason may be that the clinically-defined diagnosis of major depression is itself composed of largely unknown, but critical, neurobiological heterogeneity, which contributes to varying treatment outcomes. Here, we sought to identify a specific antidepressant treatment-responsive neurobiological phenotype vis a vis placebo. We designed a latent-space machine learning algorithm tailored for resting-state electroencephalography (rsEEG) and applied it to data from a large placebo-controlled antidepressant (sertraline) treatment prediction study in depression. Symptom change was robustly predicted in a manner both specific for sertraline (versus placebo) and generalizable across different study sites and EEG equipment. Our sertraline-predictive EEG signature furthermore generalized to a second depression sample, wherein we found reduced EEG-predicted symptom improvement using the sertraline-defined model for historically treatment-resistant patients compared to those that had previously shown a partial response to an antidepressant. Using a third independent depression data set, we then tested for two properties of the predictive signature: convergent validation and neurobiological significance. We calculated in the third sample outcome predictions derived from the rsEEG model we trained in our first sample, as well as predictions from a task-based fMRI classifier we also developed from our first sample in a prior analysis. These two predictions were found to correlate in the third sample, providing convergent multimodal evidence for a treatment-response phenotype within the broader clinical diagnosis of depression. We also found that the rsEEG-derived outcome predictions in the third sample indexed prefrontal neural responsivity, as measured by concurrent transcranial magnetic stimulation (TMS) during EEG, thereby elucidating neurobiological significance. Finally, in a fourth depression treatment data set we found that the smaller the rsEEG-predicted symptom improvement with sertraline, the better the response to 1 Hz repetitive TMS treatment over the right dorsolateral prefrontal cortex with concurrent psychotherapy. Our findings thus advance the neurobiological understanding of depression and antidepressant treatment through an EEG-tailored computational model, as well as provide a clinically applicable avenue for personalized treatment approaches in psychiatry with the possibility of differential treatment prediction.

Major depression, as currently defined based on clinical criteria, entails a heterogeneous mix of neurobiological phenotypes[1]. This heterogeneity may account for the oft-reported modest superiority of antidepressant medication over placebo (Cohen's d ~0.3)[2-6]. Work over the past two decades has suggested that resting-state electroencephalography (rsEEG) may be able to identify treatment-predictive heterogeneity in depression[7-10]. Specific attention has been paid to prefrontal and parietal signals carried by the theta (4-7 Hz) and alpha (8-12 Hz) frequency bands[7-13]. However, prior studies have either identified non-specific predictors that do not differentiate between response to drug versus placebo, such as rostral anterior cingulate theta current density[11-13], or failed to yield robust and reproducible neural signatures that are predictive at the individual patient level[8]. As such, we still lack a robust neurobiological signature for an antidepressant-responsive phenotype that could identify which patients will derive large benefit of medication over placebo, and which will not. Delineating such a signature would advance both a neurobiological understanding of treatment response and yield important clinical implications.

In order to identify a robust antidepressant-responsive depression phenotype, machine learning can be used to combine across the complex multivariate relationships existing within rsEEG data. An effective predictive rsEEG computational model, however, must deal with three critical challenges: 1) Smearing of signal and noise resulting from volume conduction due to each electrode picking up neural signals from multiple sources and adjacent electrodes detecting neural signals from the same sources[14]; 2) Risk of overfitting the model given the high spatio-temporal dimensionality and noisiness of EEG data[15,16]; and 3) Challenges in simultaneously optimizing feature identification and fitting of predictive regression models due to the nonlinearity of the objective function within its expansive parameter space[17].

To address each of these challenges, we developed a machine learning algorithm, which we call Sparse EEG Latent SpacE Regression (SELSER, see FIG. 1; Example 2). Signal identification and mitigation of volume conduction are accomplished by amplifying signal-to-noise ratio through use of spatial filters[18]. Each spatial filter transforms the multi-channel EEG data into a single latent signal, the power of which is used as a feature for the machine learning algorithm. Since model fitting is done under a sparse constraint on the number of spatial filters, this serves as well to reduce dimensions of the underlying latent signals and thus the chance of overfitting. Finally, we mathematically formulated the outcome prediction framework as solving a convex problem that related EEG time series to the treatment outcome directly, yielding a globally optimal solution[19]. This approach can be contrasted, for example, with regression models being applied to channel-level rsEEG power measures, which does little to mitigate volume conduction. Likewise, conventional latent space methods such as Independent Component Analysis (ICA)[20] and Principal Component Analysis (PCA) are not optimal in that they are unsupervised approaches not directly related to optimizing for the treatment outcome prediction target. In light of prior rsEEG work[7-9], we predicted that SELSER-established neural signals drawn from theta and alpha frequency bands would most strongly predict treatment outcome. Once a treatment-predictive phenotype is identified, we can further validate and study the neurobiological significance of this phenotype.

Figure 8:
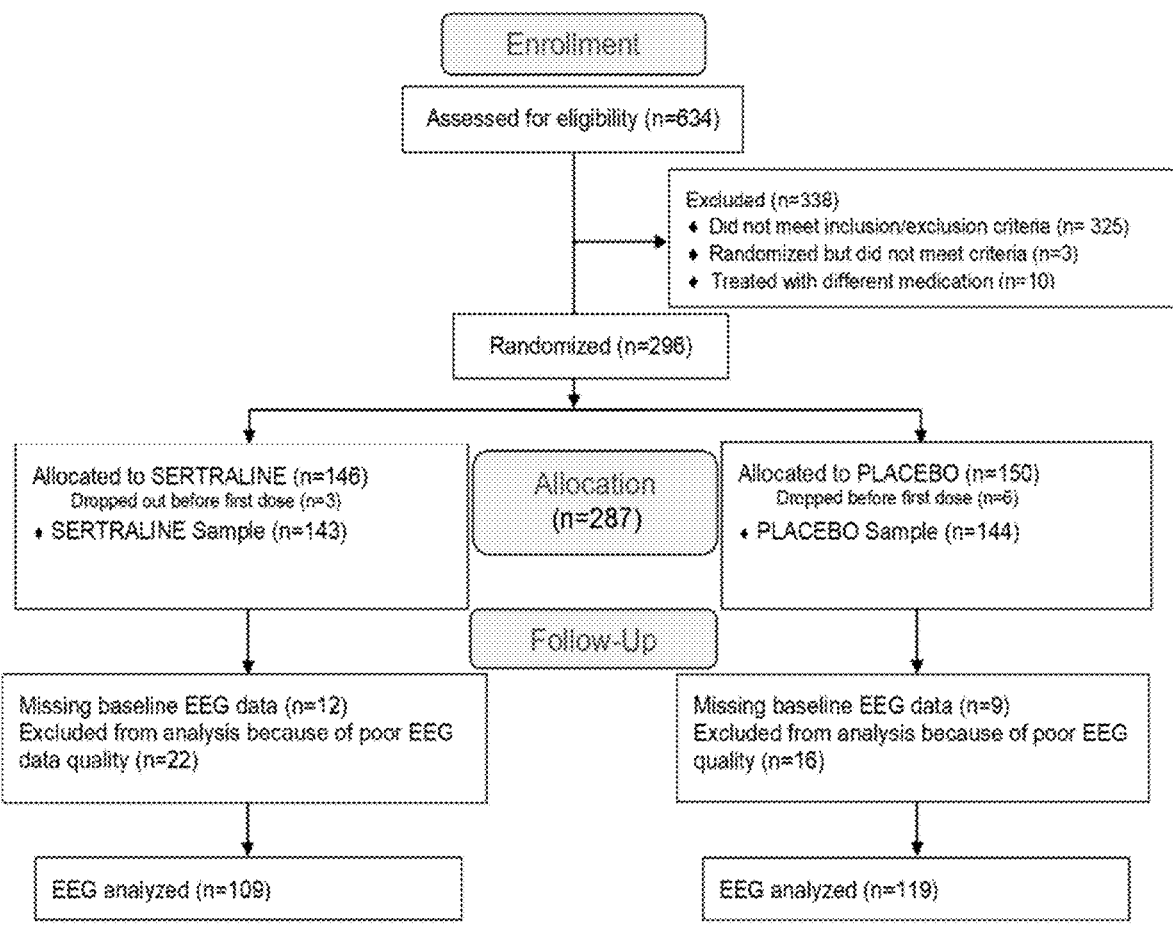
FIG. 8. EMBARC CONSORT Flow Diagram for the patients included in the treatment prediction analyses. For this analysis, patients were included (1) regardless of their HAMD$_{17}$ score, and (2) if they had resting-state EEG data of sufficient quality.

Data were drawn from four studies. Establishment of the treatment-predictive rsEEG signature was accomplished with data from the Establishing Moderators and Biosignatures of Antidepressant Response in Clinic Care (EMBARC) study[21]. EMBARC is the largest neuroimaging-coupled placebo-controlled randomized clinical trial (RCT) in depression to date and involved randomization of 309 medication-free depressed outpatients to receive either the selective serotonin reuptake inhibitor (SSRI) sertraline or placebo for eight weeks (FIG. 8). Of these, 228 had high-quality rsEEG data. We then compared the predictive utility of this algorithm against conventional machine learning approaches on the EEG data as well as a predictive model built on clinical data alone. The generalizability of the antidepressant-predictive signature was then tested in a second independent sample of depressed patients (N=72), for whom we had historical information about treatment response during the current depressive episode. A third independent sample of depressed patients (N=24) was used to assess two features of the treatment-predictive rsEEG signature: convergent validity and neurobiological significance. Specifically, we tested whether expression of our rsEEG signature correlated with another machine learning signature we developed based on task-based fMRI activation in EMBARC[22], as this would provide further convergent validation of the rsEEG signature identified here. We also tested in the third sample whether regions that were prominent in the rsEEG signature reflected individual differences in cortical responsivity, as directly assessed through single pulse transcranial magnetic stimulation (TMS) during concurrent EEG recording. Finally, in a fourth depressed sample (N=152) that was treated with either 10 Hz left dorsolateral prefrontal repetitive TMS (rTMS) or 1 Hz right dorsolateral prefrontal rTMS (both with concurrent psychotherapy), we tested whether the strength of the EMBARC-trained rsEEG signature predicted outcome with an antidepressant treatment that has a putatively different mechanism of action. This allowed us to test the generalizability of our results and open up the potential for treatment selection by defining the neural predictors of antidepressant response. Together, these efforts aimed to reveal a treatment-responsive phenotype in depression, dissociate between medication and placebo response, establish its mechanistic significance, and provide initial evidence for the potential for treatment selection based on a rsEEG signature.

Results

Treatment Prediction from Pretreatment Resting EEG Using SELSER

Figure 9:
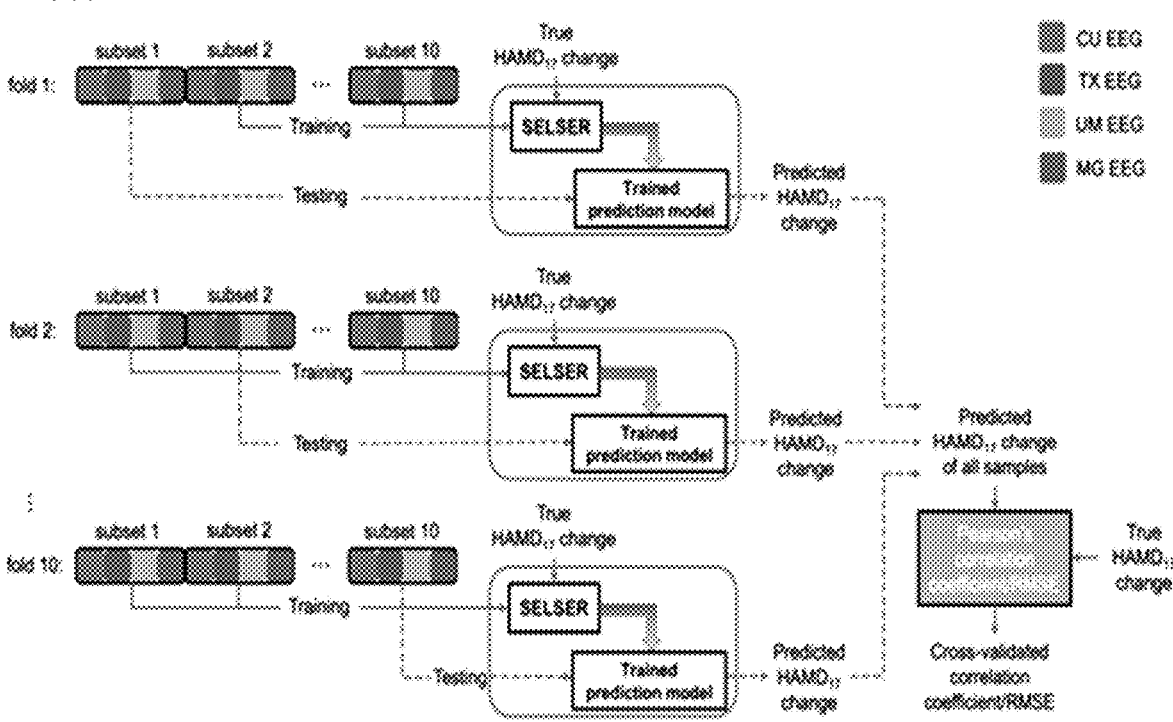
FIG. 9. Illustration of SELSER training and evaluation using 10-fold stratified cross-validation. Study sites were Columbia University (CU), University of Texas Southwestern Medical Center (TX), University of Michigan (UM) and Massachusetts General Hospital (MG). Data were randomly partitioned into 10 subsets, such that each subset containing an approximately equal number of subjects from each of the four study sites. A subset was left out as the test data, and the remaining 9 subsets were used as the training data. The process was then repeated 10 times, where each of the 10 subsets was used exactly once as the test data. As a result, each subject had a predicted HAMD$_{17}$ score change. The prediction performance was then quantified by the Pearson's correlation coefficient and root mean square error (RMSE) between the cross-validated prediction of the HAMD$_{17}$ score change and the true HAMD$_{17}$ score change.

We built prediction models using pretreatment rsEEG by applying SELSER to each of four canonical EEG frequency bands (theta: 4-7 Hz, alpha: 8-12 Hz, beta: 13-30 Hz, gamma: 31-50 Hz) in each resting condition (eyes open or eyes closed, each comprising two 2-minute blocks per patient). Treatment outcome was pre-minus post-treatment difference in Hamilton Depression Rating Scale ($HAMD_{17}$) scores, with missing endpoint values imputed in order to maintain an intent-to-treat framework. All of the unknown parameters were optimized in conjunction via a convex optimization algorithm, and model performance was tested using 10-fold cross-validation (FIG. 1 and FIG. 9; Example 2).

Figure 2A:
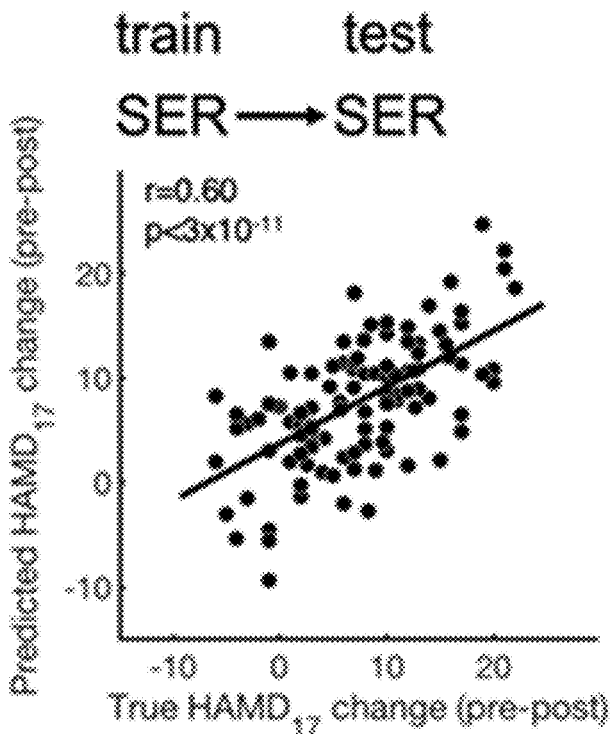
FIGS. 2A-2F. Prediction of outcome specific to sertraline using SELSER (Sparse electroencephalography (EEG) Latent SpacE Regression) on resting eyes open alpha-frequency range data.
Figure 2B:
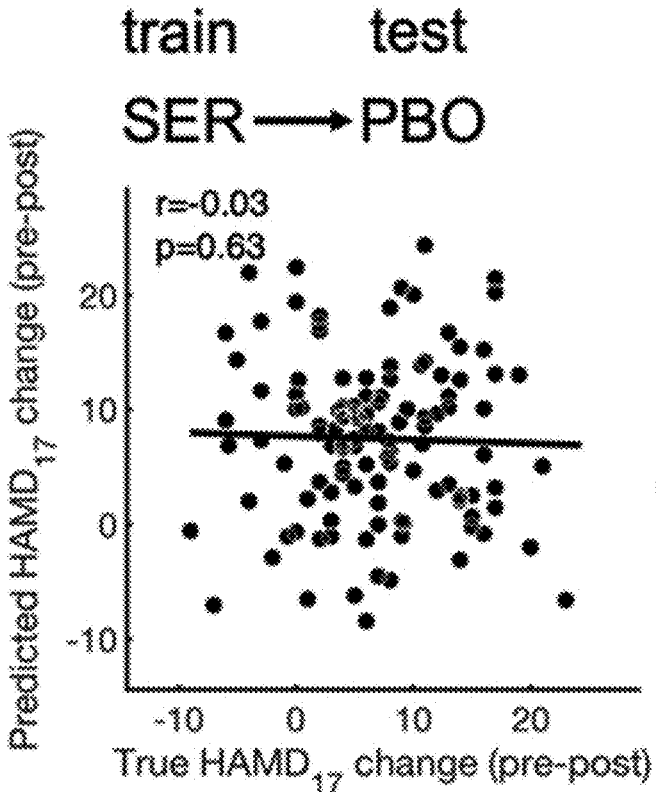

For the sertraline arm, only alpha signals from the resting eyes open (REO) condition were significantly predictive of the observed treatment score changes during cross-validation (FIG. 2A; r=0.60, root mean square error (RMSE)= 5.68, Bonferroni-corrected $p<3\times10^{-11}$; permutation test-verified using 1000 permutations p<0.001). When the sertraline-trained model was applied to the placebo arm, however, outcome could not be predicted (FIG. 2B, r=−0.03, RMSE=9.77, p=0.63), thus demonstrating the specificity of this model for sertraline prediction (Fisher's z test: z=4.94, $p=8\times10^{-7}$). Application of SELSER to alpha-frequency REO EEG signals could not, however, predict baseline $HAMD_{17}$ scores (r=0.06, RMSE=6.10, p=0.27), illustrating that the treatment-predictive model was not related to baseline depression severity.

Figure 2C:
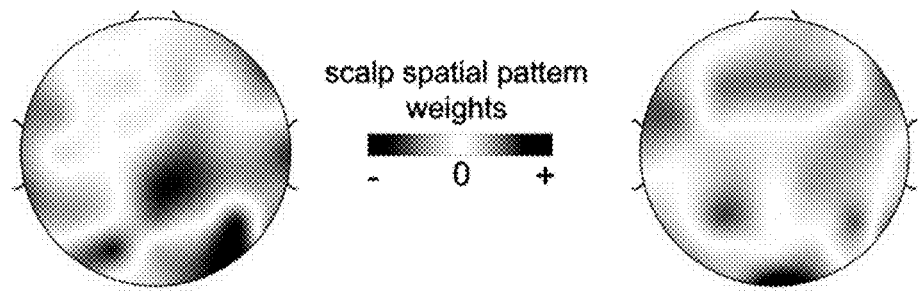
Figure 2D:
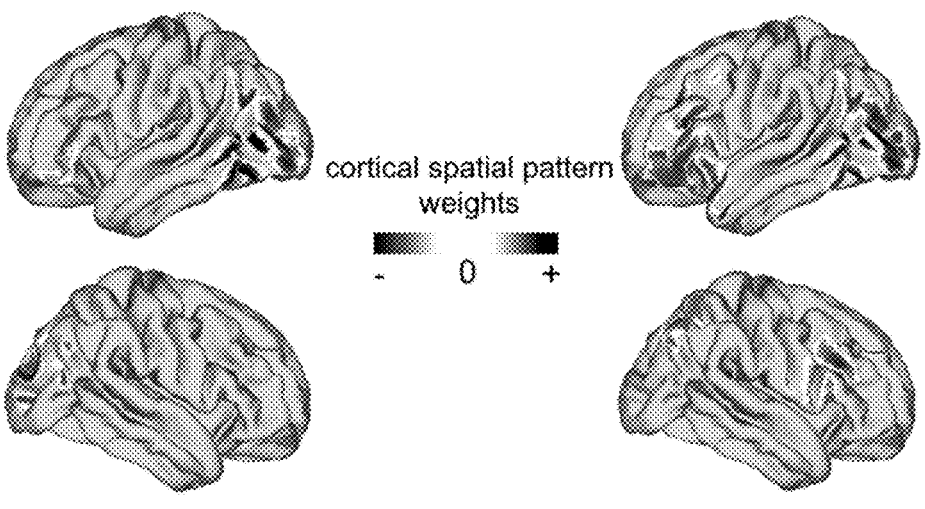
Figure 10:
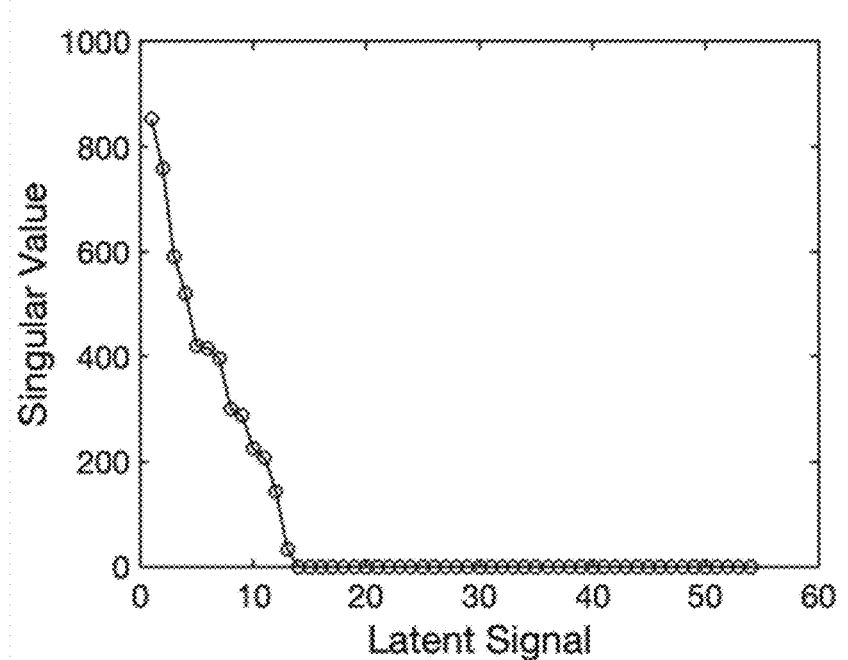
FIG. 10. Singular values associated with alpha SELSER latent signals for the sertraline arm of EMBARC. From left to right, the latent signals are sorted according to decreasing singular values. The alpha rsEEG data from all the participants in the sertraline arm were used to train the SELSER model.

As a result of the algorithm-enforced low-dimensionality constraint on the latent signals in SELSER, only a few latent signals were obtained in each model (FIG. 10). For the sertraline alpha REO model, the scalp and cortical spatial maps of the two latent signals with the most positive and negative regression weights are shown in FIG. 2C and FIG. 2D, respectively. The spatial pattern of the latent signal with the most positive regression weight was mainly centered around the right parietal-occipital regions, which was in line with the findings reported in previous rsEEG-based MDD biomarker studies[23], where greater parietal-occipital alpha power was found to be predictive of better SSRI treatment outcome. By contrast, the spatial pattern of the latent signal with the most negative regression weight was heavily concentrated in both the lateral prefrontal and parieto-occipital regions.

Figure 11A:
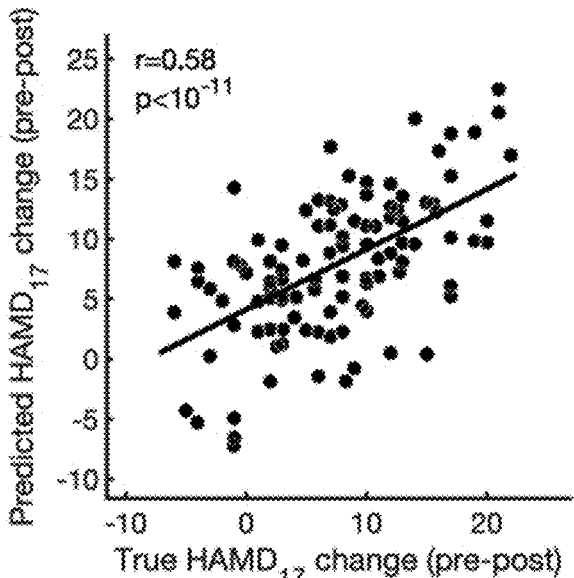
FIGS. 11A-11C. Prediction of outcome specific to sertraline using SELSER trained on resting eyes open alpha-frequency range data of different lengths. Prediction performance was assessed with 10×10 stratified cross-validation prediction.
Figure 11B:
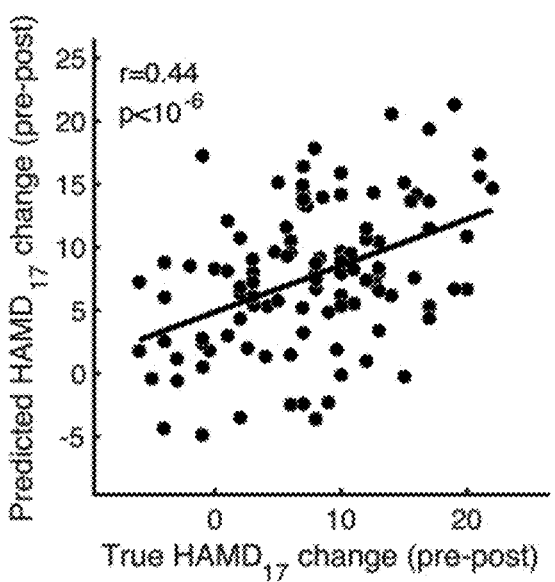
Figure 11C:
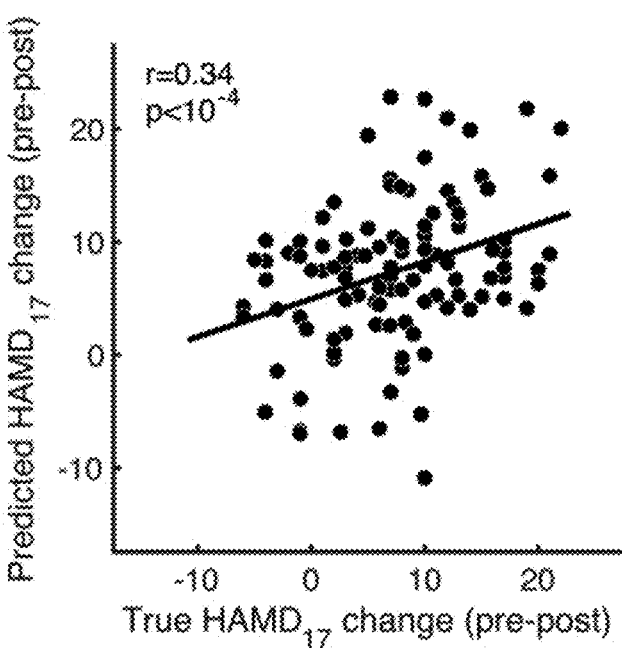
Figure 12A:
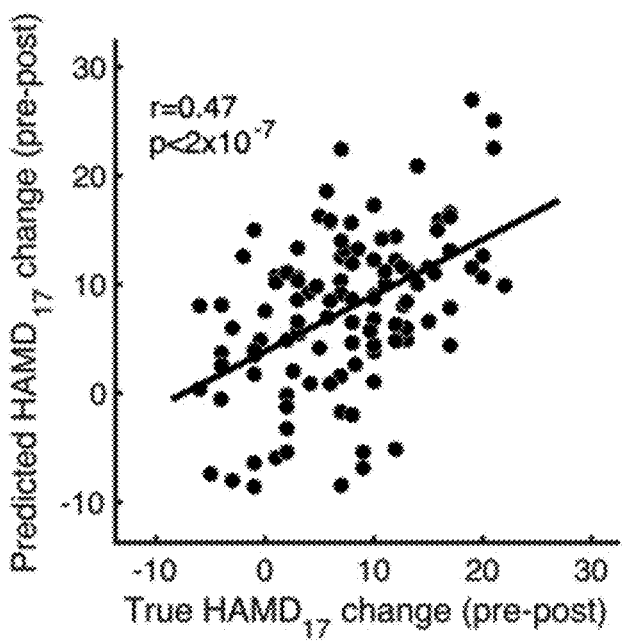
FIGS. 12A-12C. Prediction of outcome specific to sertraline using SELSER trained on resting eyes open alpha-frequency range data of different blocks. Prediction performance was assessed with 10×10 stratified cross-validation prediction.
Figure 12B:
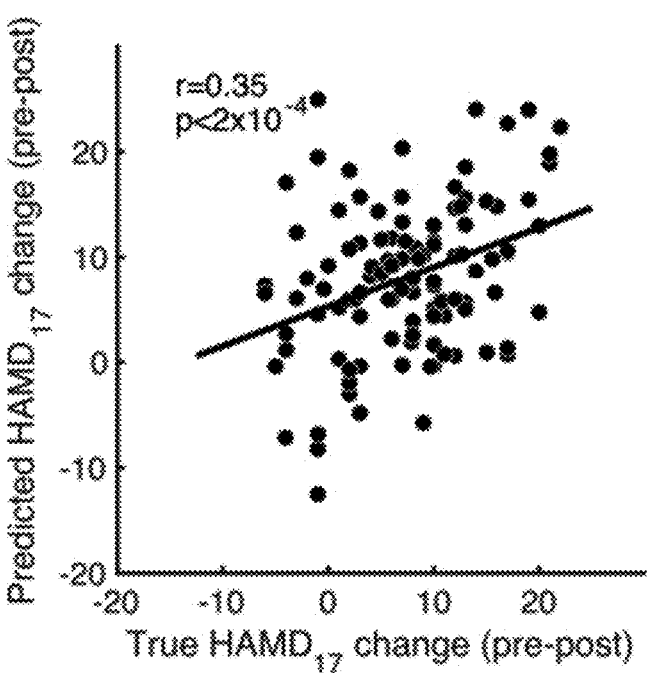
Figure 12C:
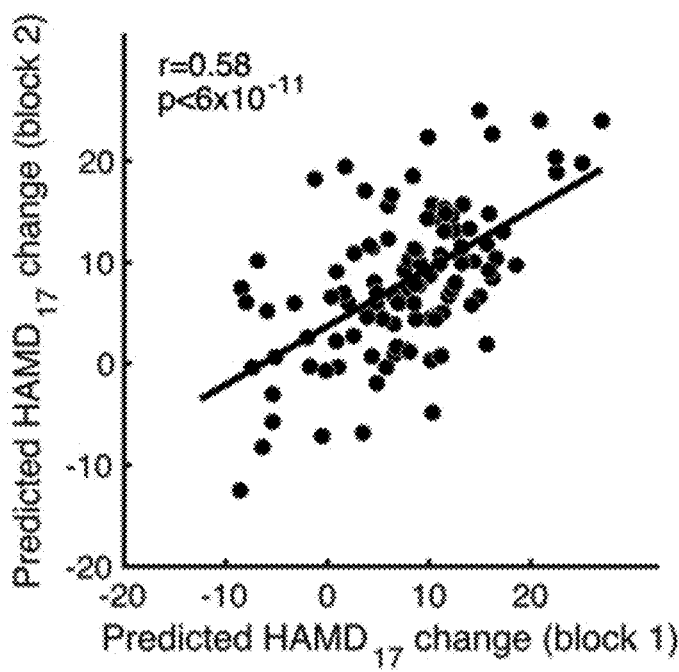

To shed light on how the prediction performance was influenced when the length of the rsEEG data varied, we repeated the SELSER prediction analysis on the alpha-frequency REO EEG signals of 1.5 minutes/block, 1 minute/block, and 30 seconds/block (as opposed to 2 minutes/block in the full data) per patient (FIG. 11). The prediction performance declined as the length of the EEG data decreased. However, there was no clear performance decline when 1.5-minute rsEEG was used compared to using the entire 2-minute rsEEG in each block, suggesting that a rsEEG session as short as 1.5-minutes/block might be sufficient for treatment prediction. When the SELSER prediction analysis was applied to each 2-minute block separately, the prediction performance suffered dramatically (FIG. 12).

Figure 3A:
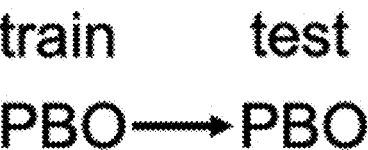
FIGS. 3A-3D. Prediction of outcome specific to placebo using SELSER on alpha-frequency range data.
Figure 3A:
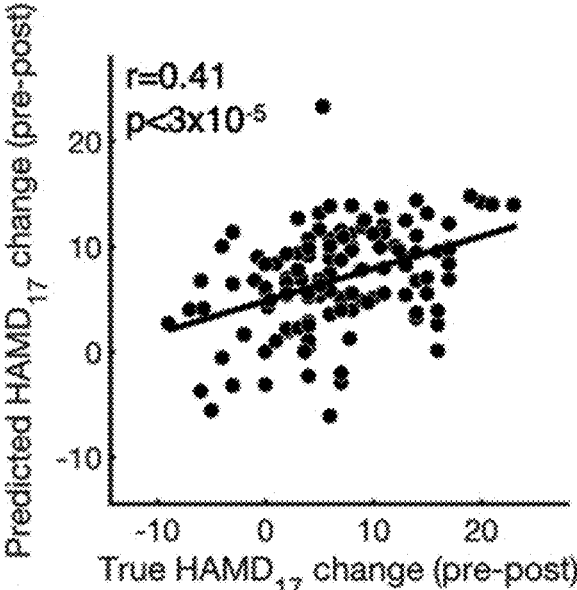
Figure 3B:
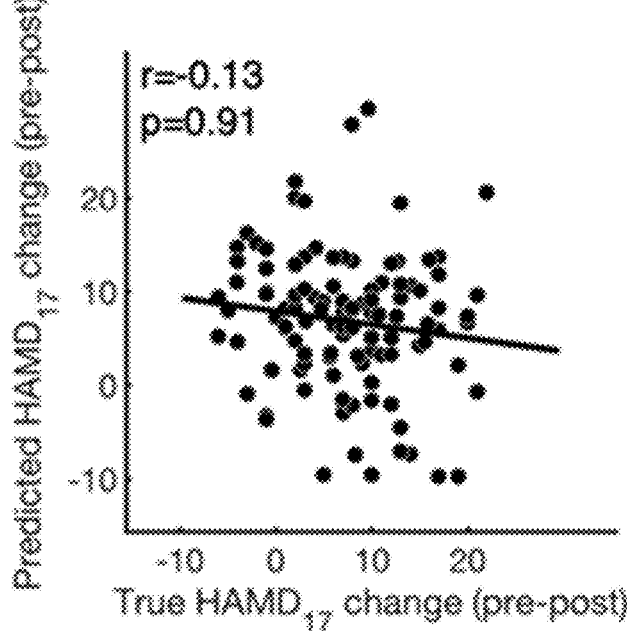
Figure 3C:
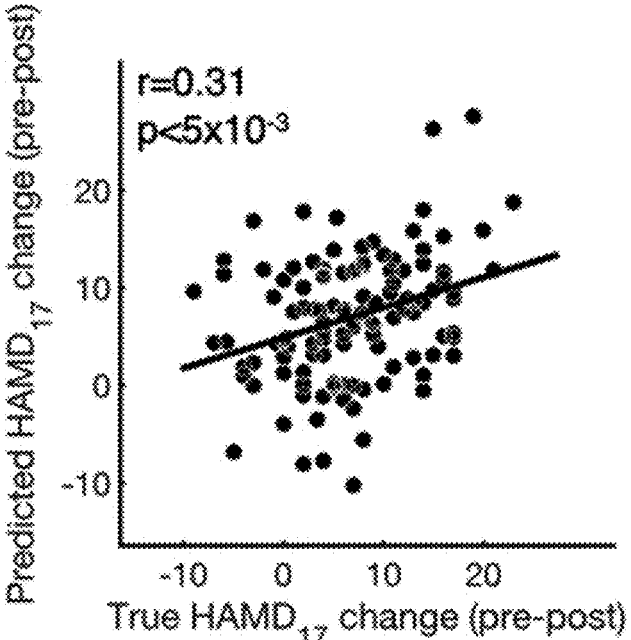
Figure 3D:
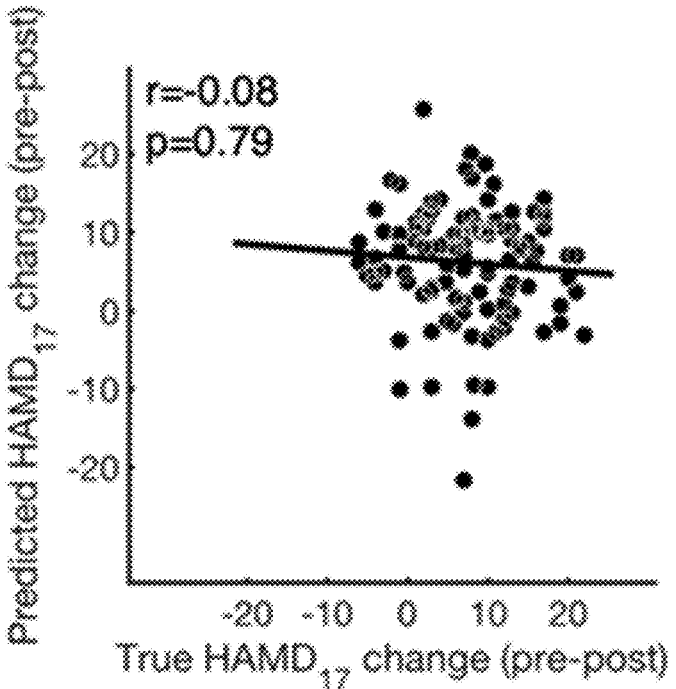
Figures 13A, 13B, 13C:
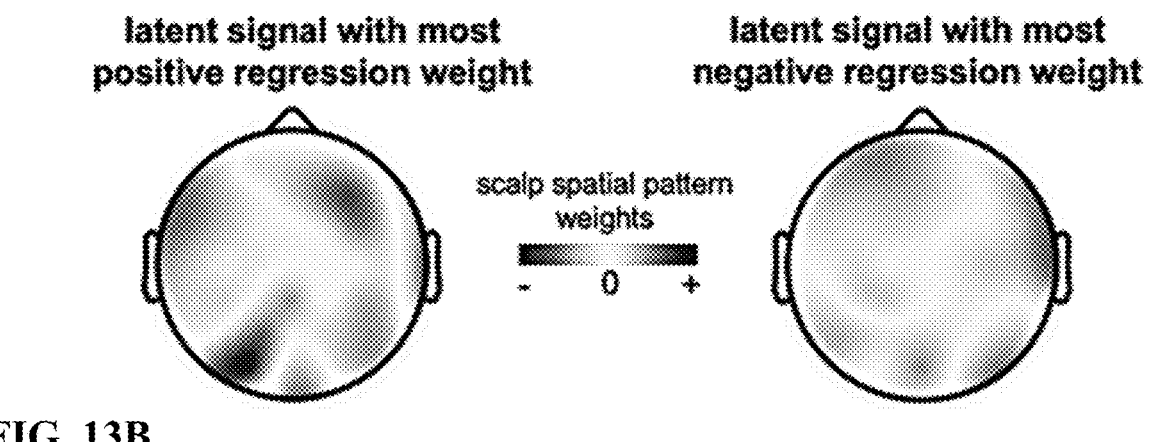
FIGS. 13A-13D. Scalp and cortical spatial patterns of the placebo (PBO) alpha SELSER latent signals.
Figure 13D:
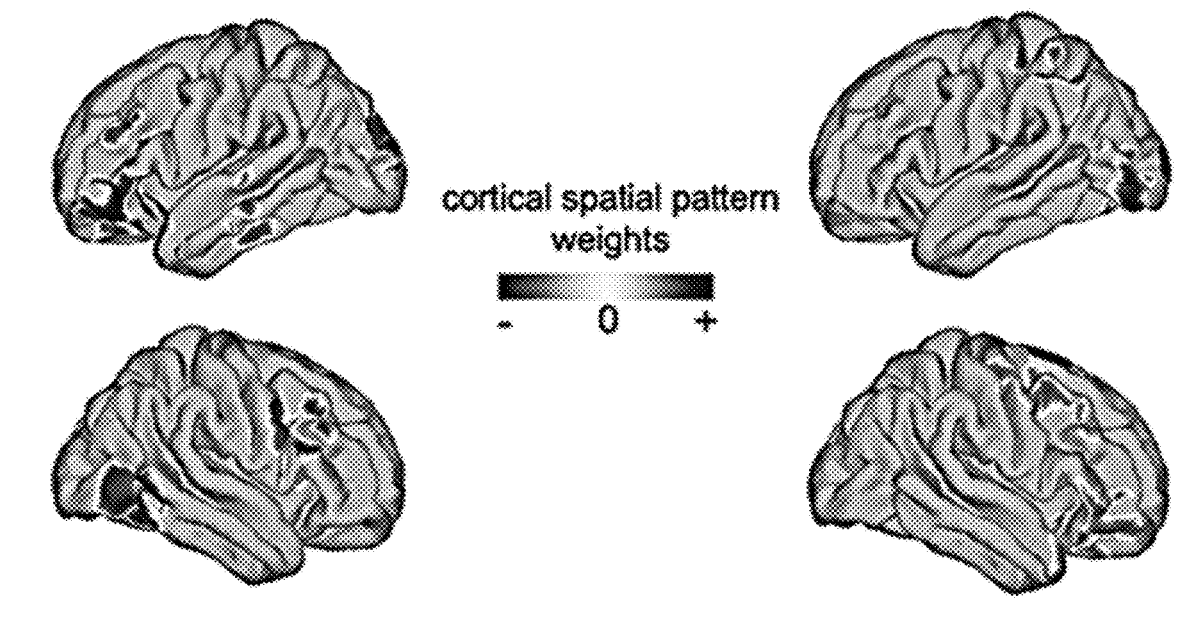
Figure 14:
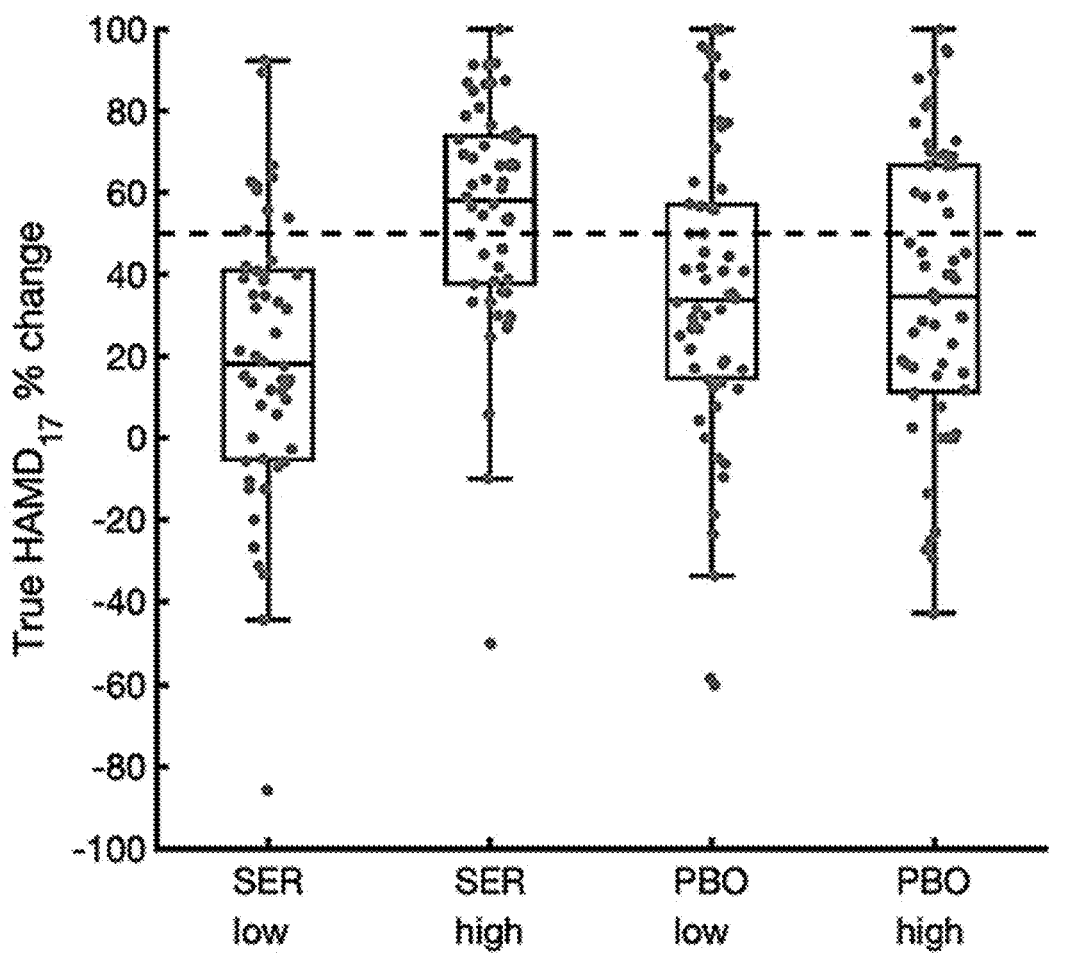
FIG. 14. Treatment stratification using the rsEEG predictive signature. Patients in each arm were partitioned into the low and high groups by applying a median split on the cross-validated predicted $HAMD_{17}$ score changes for sertraline response. Each dot represents one patient. Dashed line indicates 50% change in the true $HAMD_{17}$ score. SER=sertraline, PBO=placebo.

For the placebo group, both alpha signals from the REO and resting eyes closed (REC) conditions significantly predicted the $HAMD_{17}$ score change (REO FIG. 3A, r=0.41, RMSE=6.34, Bonferroni-corrected $p<3\times10^{-5}$; and REC FIG. 3C, r=0.31, RMSE=7.60, Bonferroni-corrected $p<5\times10^{-3}$; permutation test-validated p<0.001). The spatial maps of the two latent signals with the most positive and negative regression weights are shown in FIG. 13 for the REO and REC conditions. For the REO condition, the spatial patterns of the latent signals were predominantly in the temporal and occipital regions, whereas for the REC condition, frontal-parietal and frontal regions were the most prominent. When applied to the sertraline arm, both regression models failed to predict outcome (FIG. 3B and FIG. 3D, Fisher's z test: z>2.98, p<0.003), demonstrating the specificity of these models for placebo outcome prediction and distinction from the sertraline-predictive model above.

Treatment Stratification Based on SELSER Predictions

Figure 2E:
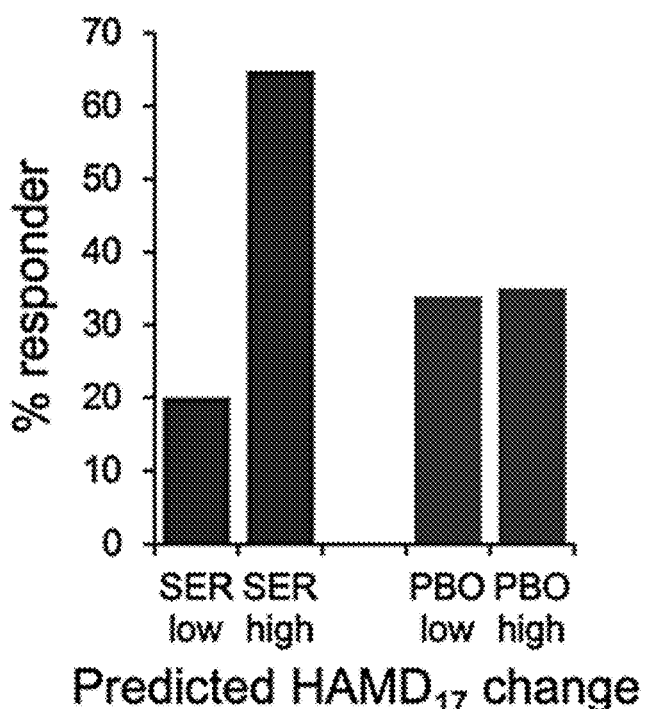

To simply visualize how the SELSER predictions in FIG. 2A could be used for treatment stratification, we partitioned the patients in each arm by applying an arbitrary median split on the cross-validated predicted $HAMD_{17}$ score changes derived from the sertraline alpha REO model. We then calculated the rates of treatment response (≥50% reduction in symptoms) for the portion of patients above the median ("high") and below the median ("low"), respectively, based on the model-predicted $HAMD_{17}$ change scores (FIG. 2E). For the sertraline arm, the high group reached a response rate of 65%, which more than tripled the response rate (20%) in the low group and was considerably higher than the response rates in the placebo arm (35% and 34% for the high and low groups, respectively). Thus, only for patients at the higher range of predicted $HAMD_{17}$ score changes is sertraline superior to placebo.

Treatment Prediction Across Study Sites

Figure 2F:
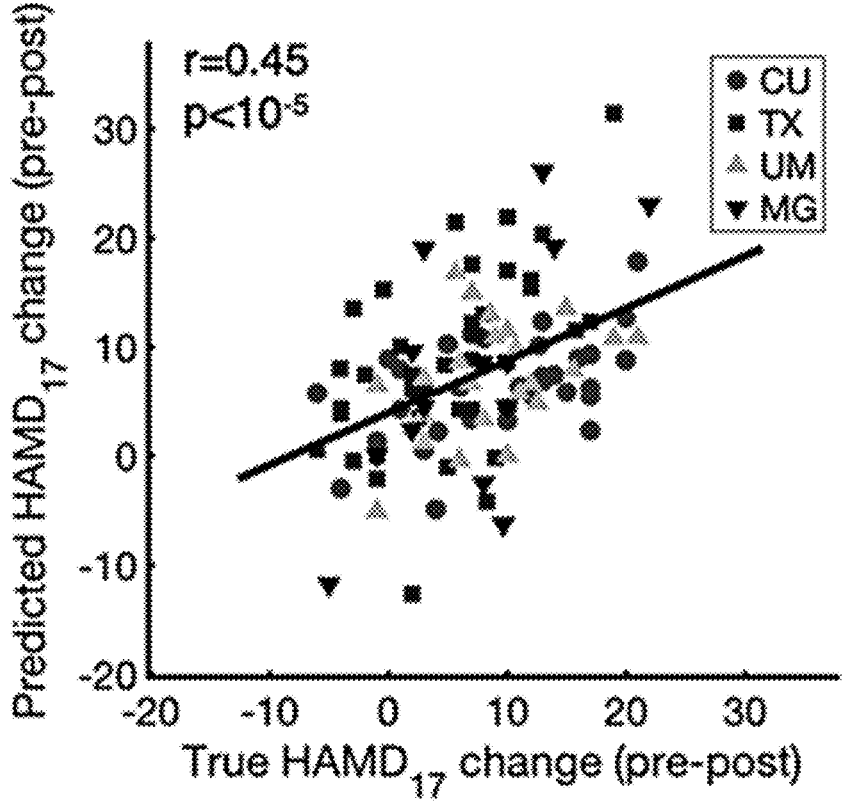
Figure 15A:
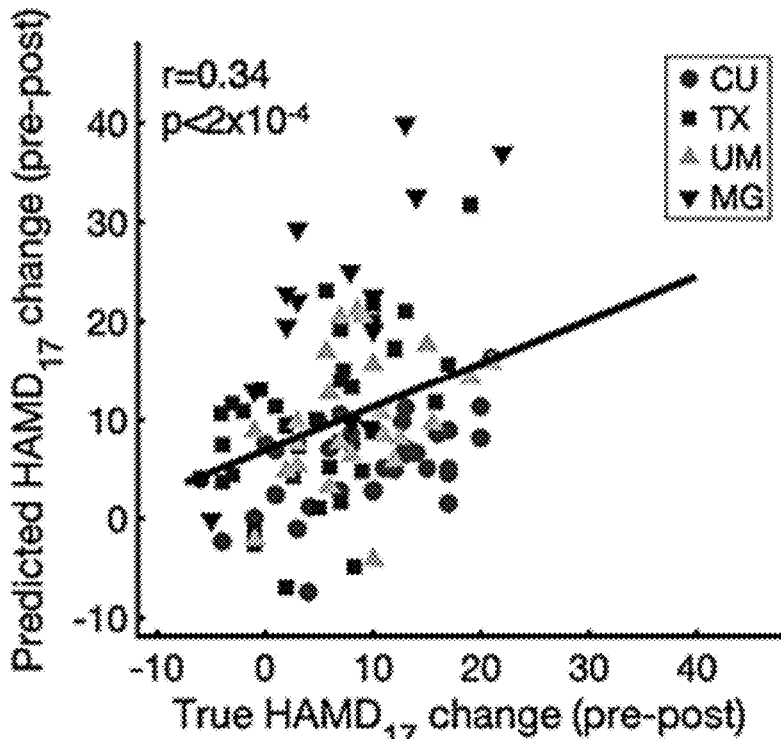
FIGS. 15A-15B. Influence of site correction on leave-study-site-out cross-validation performance. Study sites were Columbia University (CU), University of Texas Southwestern Medical Center (TX), University of Michigan (UM) and Massachusetts General Hospital (MG). Treatment prediction across study sites was assessed by a leave-study-site-out cross-validation on the alpha REO sertraline model.
Figure 15B:
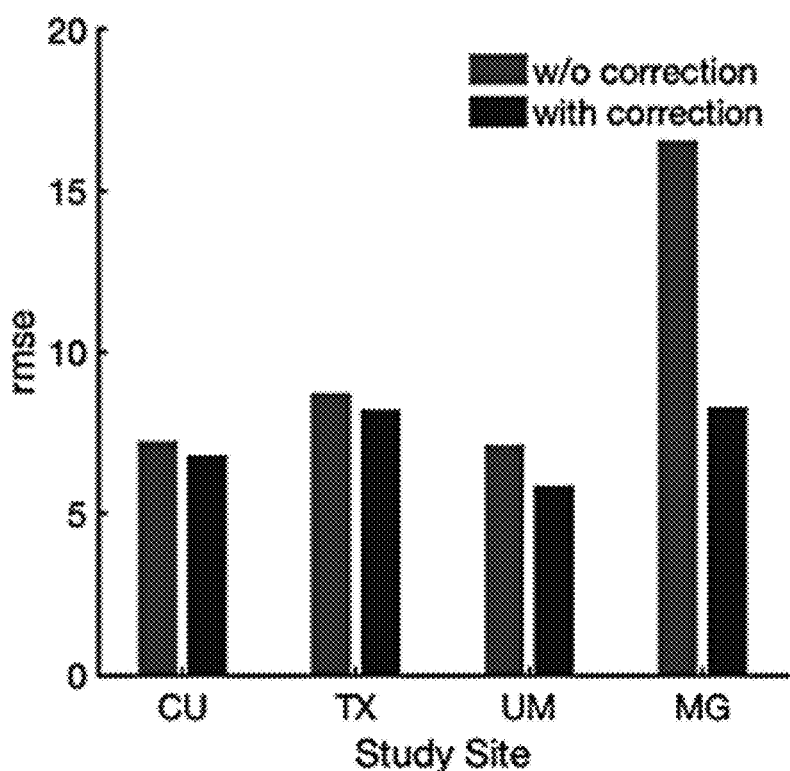

To further assess the generalizability of the prediction models to unseen data collected with different EEG amplifiers, a leave-study-site-out analysis was performed by iteratively using three study sites' data to train the model, and the fourth site's data for testing the model. Since the four study sites' EEG data were acquired with three different EEG amplifiers (Table 1), marked variability of prediction performance was observed across study sites (FIG. 15). To mitigate this site effect, the mean of the covariance matrix was removed from each study site prior to the SELSER analysis. For the sertraline arm, only the alpha REO model was significantly predictive of the treatment outcome when cross-validating between study sites (FIG. 2F; r=0.45, RMSE=7.02, Bonferroni-corrected $p<10^{-5}$; permutation test-validated using 1000 permutations p<0.001), demonstrating the robustness of this model for unseen data from a different EEG amplifier—arguably a worst-case scenario with respect to testing through cross-validation. An equivalent 4-fold cross-validation model sampling across all sites remained strongly predictive (r=0.58, RMSE=5.63, $p<10^{-10}$; permutation test-validated using 1000 permutations p<0.001). Further restricting the sample size via a 2-fold cross-validation across all sites yielded a lower yet still highly significant predictive performance (r=0.38, RMSE=6.32, $p<3\times10^{-5}$). For the placebo arm, none of the REO and REC models was predictive of the treatment outcome when cross-validating between study sites (r's<0.22, RMSE>7.90, Bonferroni-corrected p>0.07). When the leave-study-site-out performance of the sertraline and placebo classifiers was compared, the sertraline alpha REO predictive model still showed significantly greater specificity in predicting sertraline over placebo responding (Fisher's z test: z=3.83, p=104).

TABLE 1

Baseline sociodemographic and clinical variables for the EMBARC study.
Statistics reflect comparisons of the Sertraline and Placebo arms

| Categorical variables | Sertraline | | Placebo | | $\chi^2$ | p value |
|---|---|---|---|---|---|---|
| | n | % | n | % | | |
| Gender | | | | | 4.15 | 0.04 |
| Male | 30 | 27.52 | 48 | 40.34 | | |
| Female | 79 | 72.48 | 71 | 59.66 | | |
| Race | | | | | 1.73 | 0.42 |
| White | 68 | 62.39 | 83 | 69.75 | | |
| African American | 20 | 18.35 | 20 | 16.81 | | |
| Other | 21 | 19.27 | 16 | 13.45 | | |
| Employment status | | | | | 0.12 | 0.94 |
| Employed | 58 | 53.21 | 66 | 55.46 | | |
| Unemployed | 46 | 42.20 | 48 | 40.34 | | |
| N/A or Missing | 5 | 4.59 | 5 | 4.20 | | |

| Continuous variables | Mean | SD | Mean | SD | t value | p value |
|---|---|---|---|---|---|---|
| Age | 37.06 | 13.94 | 38.41 | 12.63 | −0.77 | 0.44 |
| Age of onset | 16.36 | 5.90 | 15.94 | 5.60 | 0.55 | 0.59 |
| Years of education | 15.06 | 2.57 | 15.36 | 2.54 | −0.87 | 0.38 |

TABLE 1-continued

Baseline sociodemographic and clinical variables for the EMBARC study.
Statistics reflect comparisons of the Sertraline and Placebo arms

| | | | | | | |
|---|---|---|---|---|---|---|
| Number of MDE | 30.78 | 121.29 | 45.43 | 160.15 | −0.77 | 0.44 |
| Duration of current episode | 42.70 | 74.64 | 51.90 | 117.91 | −0.70 | 0.49 |
| HAMD$_{17}$ | 18.16 | 4.70 | 18.72 | 4.41 | −0.94 | 0.35 |
| Medication dose | 103.48 | 32.28 | 108.67 | 29.73 | −1.18 | 0.24 |

Notes for Table 1.
MDE = major depression episodes;
*4 MDD participants (1 placebo, and 3 with sertraline) with no employment status.

Comparison of SELSER Predictions to Prior Methods

Figure 4A:
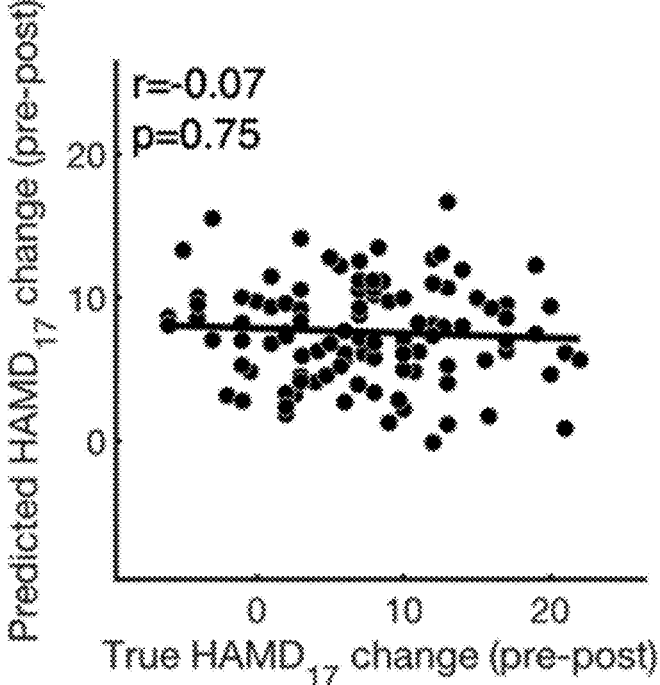
FIGS. 4A-4E. Machine learning prediction of treatment outcome using previously-suggested predictive metrics (alpha power, theta power, and theta cordance) and conventional latent space modeling approaches (PCA and ICA) on eyes open rsEEG data. 10×10 stratified cross-validation prediction using the relevance vector machine (RVM) on channel-level alpha power (FIG. 4A), theta power (FIG. 4B), theta cordance (FIG. 4C), alpha power of the PCA-extracted latent signals (FIG. 4D), or alpha power of the ICA-extracted latent signals (FIG. 4E) do not significantly predict outcome for sertraline.
Figure 4B:
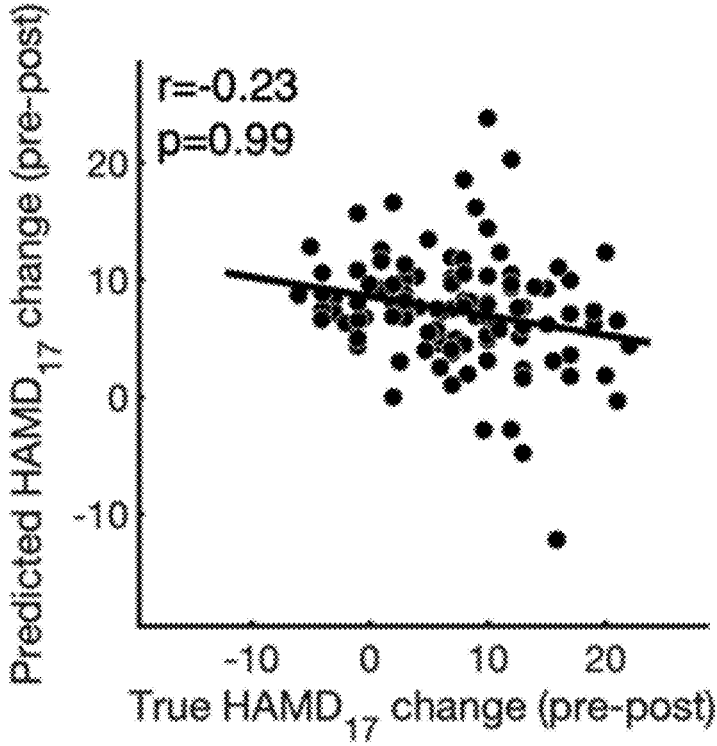
Figure 4C:
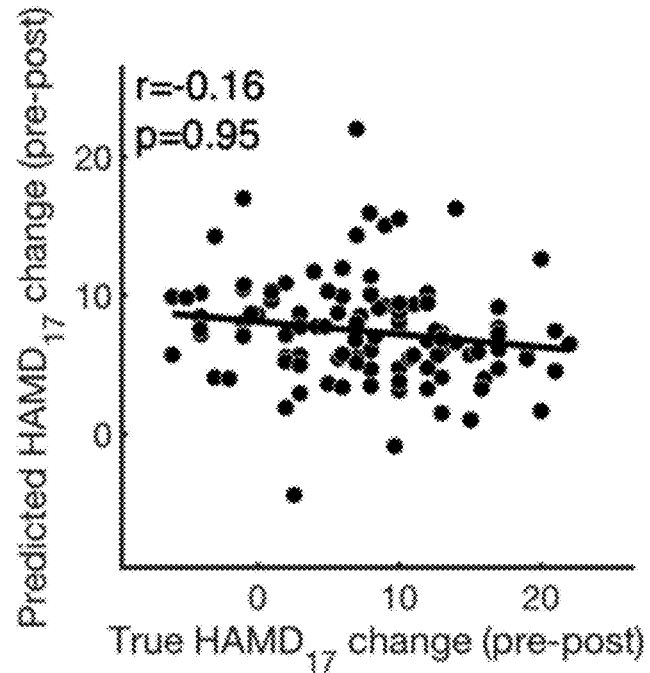
Figure 4D:
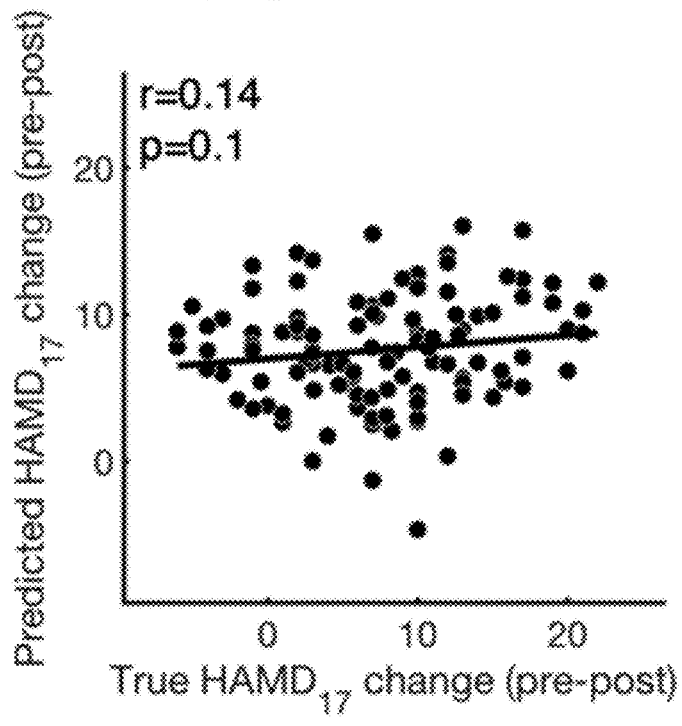
Figure 4E:
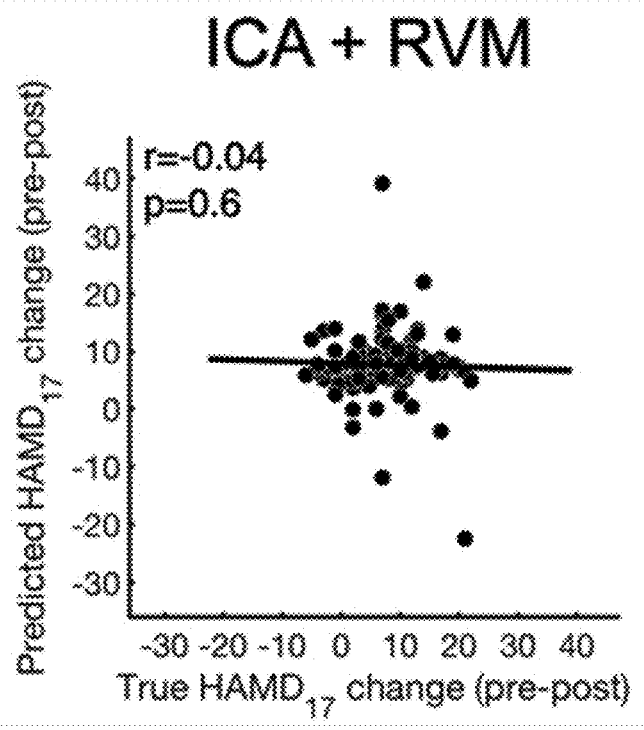

In order to benchmark SELSER against conventional machine learning approaches that do not use latent space modeling, we also trained linear regression models by using the Relevance Vector Machine (RVM)[24] on the channel-level alpha band power[25,26] (FIG. 4A), theta band power 26,27 (FIG. 4B), and theta cordance[13,23], respectively (FIG. 4C; Example 2, and FIG. 16). These three features have been frequently used in previous rsEEG-based MDD treatment prediction studies[13]. However, none of the models were predictive of the treatment outcome (r's<−0.06, RMSE>8.20, p>0.74). Moreover, to demonstrate the improvement of SELSER over conventional latent space modeling approaches, we also trained the RVM on the alpha band powers of the latent signals extracted with PCA[29] (FIG. 4D) or ICA[25] (FIG. 4E), which are among the most popular unsupervised methods to derive spatial filters from EEG (See Example 2 and FIG. 16). Here as well, both the ICA and PCA models failed to predict the treatment outcome (r's<0.15, RMSE>7.17, p>0.09).

Treatment Prediction from Symptoms

Figure 17A:
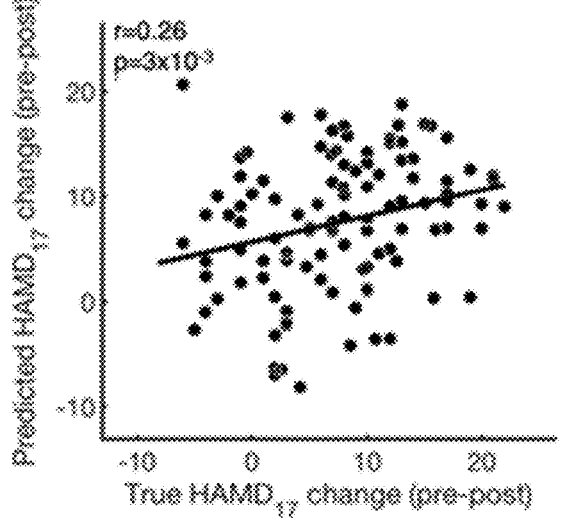
FIGS. 17A-17B. Machine learning prediction of treatment outcome from symptoms. Prediction performance was assessed with 10×10 cross-validation prediction using the relevance vector machine (RVM). Included symptom measures were the Spielberger State-Trait Anxiety Inventory, the Quick Inventory of Depressive Symptoms, the Mood and Anxiety Questionnaire, the Childhood Trauma Questionnaire, age, and education.
Figure 17B:
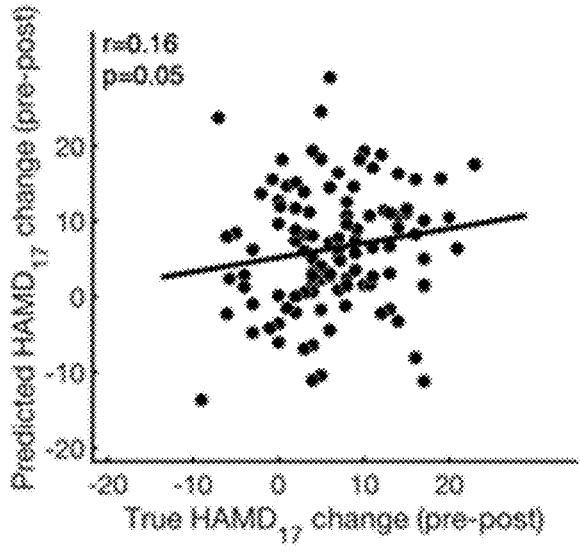

Assessing brain activation for defining an individual's sertraline responsive phenotype may not be relevant in practice if lower-cost measures such as clinical severity scores, demographic variables or historical factors like childhood trauma exposure could usefully predict outcome. This did not prove to be the case, however, as the RVM trained with all of these was only modestly predictive (FIG. 17A: r=0.26, RMSE=7.93, p=3×10$^{-3}$ for sertraline, and FIG. 17B: r=0.16, RMSE=9.56, p=0.05 for placebo). Sertraline outcome prediction with these measures was also significantly weaker than the sertraline alpha REO EEG predictive model above (Fisher's z test; z=3.11, p=0.0019). Prediction performance was even worse if only using the Quick Inventory of Depressive Symptomatology (QIDS) measure of depression severity at baseline (r=0.12, RMSE=6.85, p=0.12 for sertraline, and r=0.06, RMSE=6.72, p=0.26 for placebo).

Testing the Generalization of the rsEEG Sertraline-Predictive Signature in a Second Independent Depression Study We next tested the generalizability of the SELSER rsEEG sertraline-predictive signature from EMBARC in a second independent cohort of patients with depression. This cohort of patients were drawn from a naturalistic, longitudinal depression study in which rsEEG data were recorded at the baseline visit. Patients also completed the Antidepressant Treatment Response Questionnaire (ATRQ), which provided historical information about the number of adequate antidepressant medication trials in the current episode, as well as whether patients responded to them or not. Following conventional groupings, patients were categorized as either treatment-resistant (two or more failed antidepressant trials; N=21), or as partial responders (partial response to at least one medication; N=51). The mean-removal site correction procedure was performed for the rsEEG data, as in the leave-study-site-out analysis of the EMBARC study. We then applied the EMBARC-trained SELSER alpha-band rsEEG model to each patient, yielding a predicted HAMD$_{17}$ change for each individual, which reflects their strength of expression of the sertraline-predictive rsEEG signature. As expected, the predicted HAMD$_{17}$ change was significantly higher for the partial responder group than the treatment resistant group (FIG. 5), demonstrating the generalizability of the EMBARC rsEEG sertraline signature to the broader construct of treatment responsiveness/resistance to antidepressant medication. Moreover, information on the number of within-episode failed antidepressant trials was available for 45 of the 72 patients. Also as expected, we found a negative correlation between the number of failed trials and the magnitude of the rsEEG sertraline signature-predicted HAMD$_{17}$ improvement (r=−0.34, p=0.023).

Figure 6A:
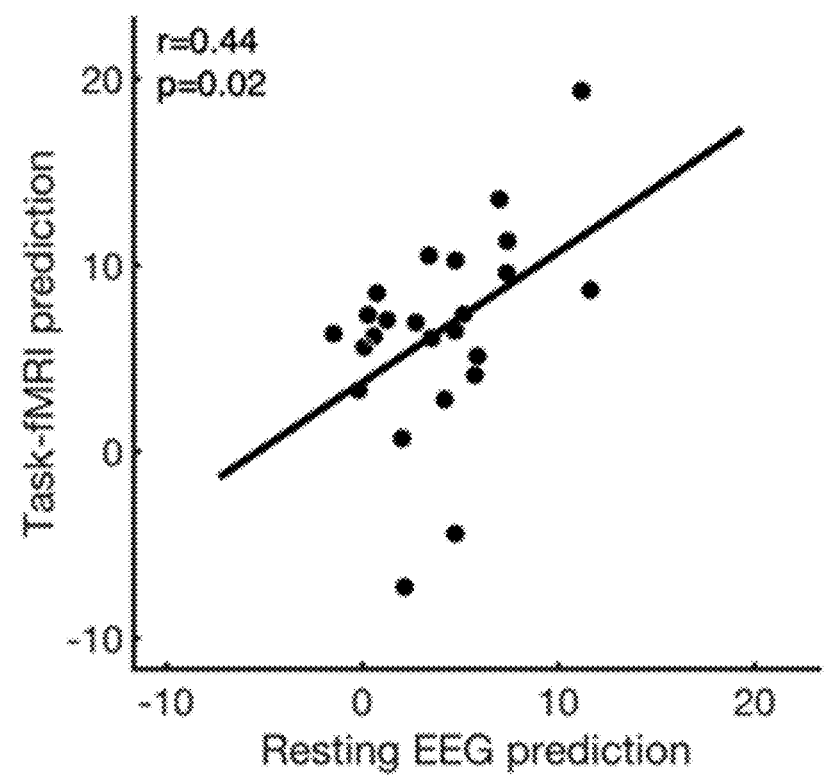
FIGS. 6A-6C. Alignment of predicted HAMD$_{17}$ change calculated by the rsEEG model and predicted HAMD$_{17}$ change calculated by a machine learning model trained on task-based fMRI activation from a separate analysis on EMBARC data, as well as neural responsivity assessed through spTMS/EEG.

Alignment of rsEEG- and Task-fMRI-Derived Machine Learning Predictions in a Third Independent Study To test the convergent validity of the SELSER rsEEG model from EMBARC, we examined a separate dataset of 24 patients with depression who were assessed in a cross-sectional manner (i.e., without treatment) using both rsEEG and task-based fMRI with the emotional conflict task[22]. The reason for doing so is that we could test whether the predicted HAMD$_{17}$ change based on the EMBARC-trained SELSER rsEEG model correlated with the predicted HAMD$_{17}$ change based on an fMRI emotional conflict task-based machine learning model we established in a separate analysis of EMBARC data[22] (See Example 2). A significant positive correlation between the symptom change predicted by both of these machine learning models in an independent set of MDD patients would provide convergent support for the existence of a treatment-responsive neurobiological phenotype in MDD across populations, and across assessment modalities. Since the EEG data were recorded with yet another amplifier distinct from those used in EMBARC, the mean-removal site correction procedure was performed. The rsEEG and task-fMRI predictions were, indeed, significantly correlated with each other in these independent data (FIG. 6A; r=0.44, p=0.02), providing evidence to support the generalizability of our the SELSER model.

TMS/EEG Correlates of rsEEG Phenotype

Figure 6B:
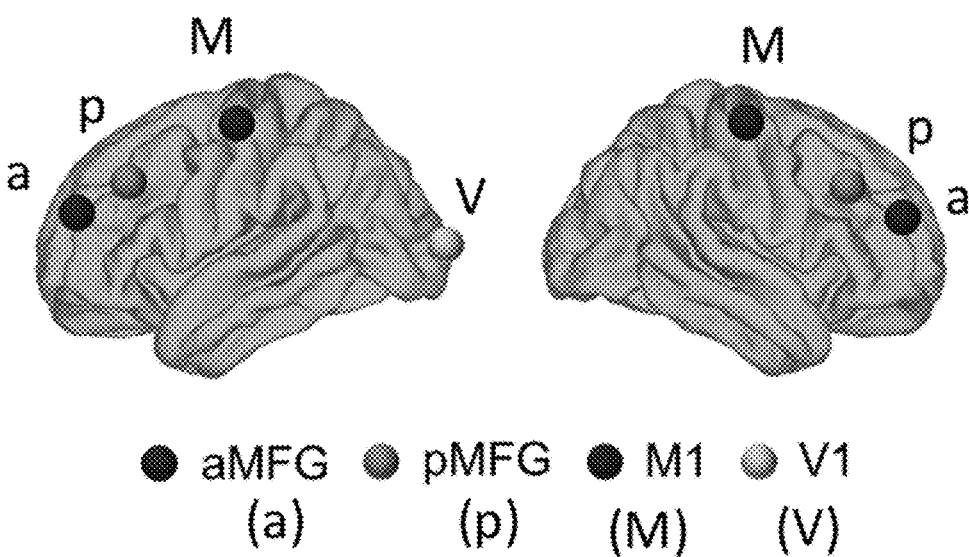
Figure 6C:
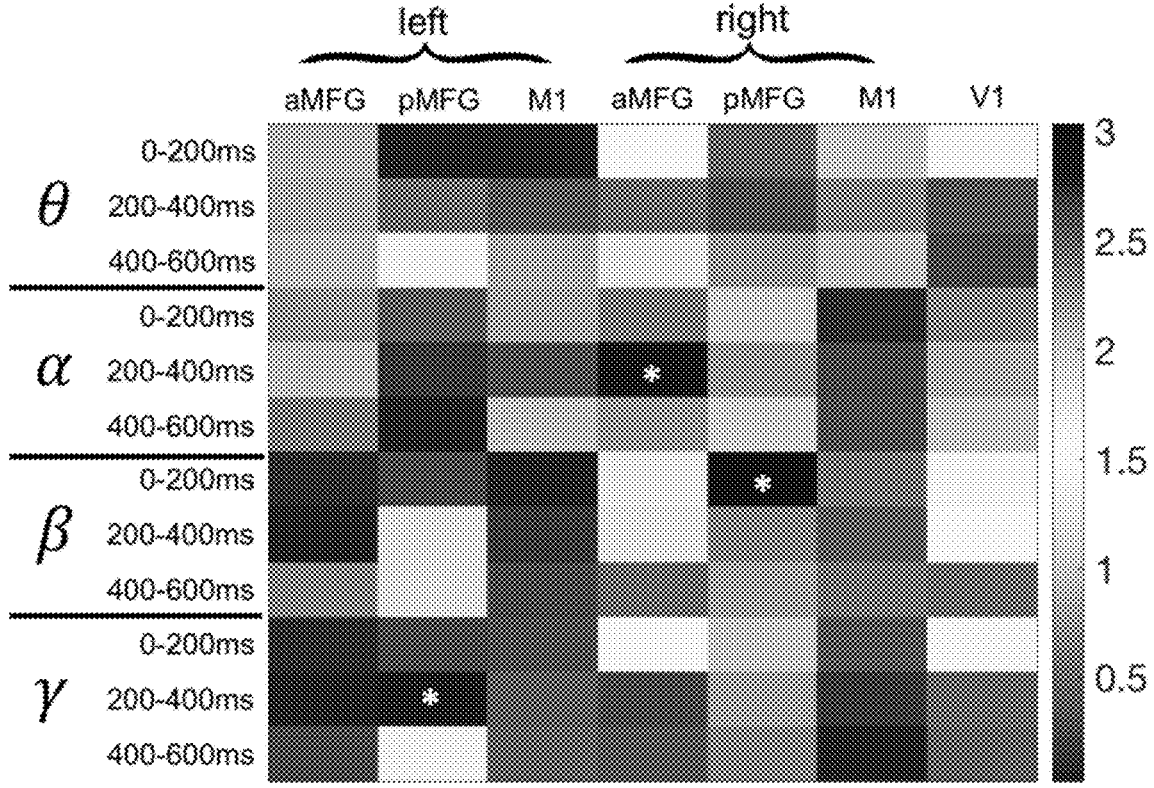

Next, to provide further insight into the neural signals driving our rsEEG-defined phenotype, we analyzed concurrent single-pulse TMS/EEG (spTMS/EEG)[30] data from the third independent depression sample as used above. Specifically, we sought to test whether cortical responsivity, as assessed by direct stimulation using spTMS/EEG to regions either prominent or minimal within the spatial patterns of the rsEEG latent signals, induced neural responses that correlated with the rsEEG-defined treatment-predictive phenotype. The stimulated regions were the bilateral posterior dorsolateral prefrontal cortices (pDLPFC), anterior DLPFC (aDLPFC), along with primary visual cortex (V1) and bilateral primary motor cortices (M1) as the control regions (FIG. 6B). We localized pDLPFC and aDLPFC using neuronavigation based on their being nodes within the frontoparietal and salience resting-state networks, respectively, as we have done in our prior work[31]. To quantify the correlation between the spTMS/EEG responses and rsEEG phenotype, we again employed SELSER to learn predictive models from the spTMS/EEG data to the rsEEG predictions, and calculated the leave-one-out cross-validated Pearson's correlation coefficients between the predicted rsEEG predictions and true rsEEG predictions (FIG. 6C). Correlations between the SELSER rsEEG phenotype and spTMS/EEG responses to stimulation at three of four prefrontal cortical regions survived correction for multiple comparisons. This included right aDLPFC stimulation (alpha band, 200-400 ms: r=0.60, false discovery rate (FDR)-corrected p=5.5× $10^{-4}$), left pDLPFC stimulation (gamma band, 200-400 ms: r=0.58, FDR-corrected p=8×$10^{-4}$) and right pDLPFC stimulation (beta band, 0-200 ms: r=0.60, FDR-corrected p=4.6× $10^{-4}$). Correlation of responses to stimulation of primary motor or visual cortices did not survive correction.

Figure 7:
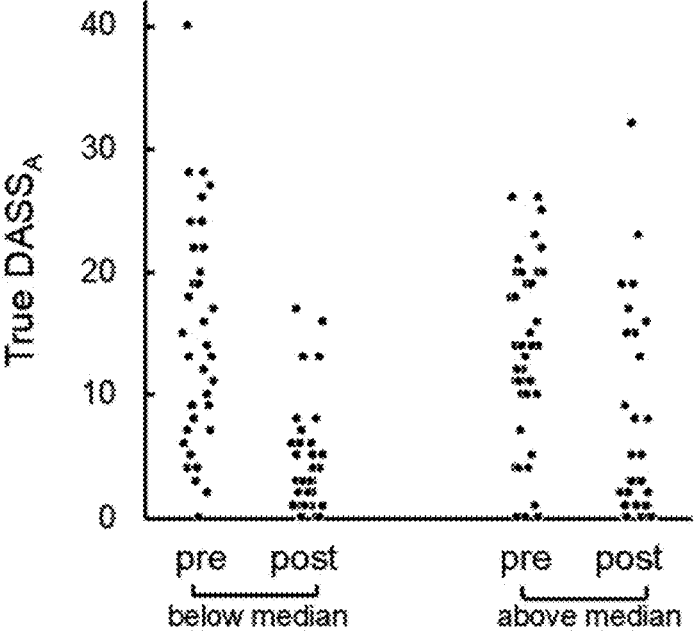
FIG. 7. Prediction of treatment outcome with right DLPFC 1 Hz rTMS treatment by the EMBARC-trained SELSER rsEEG model, applying to pre-rTMS eyes open rsEEG. The scatterplot shows the pre and post-treatment scores for patients on the Anxiety subscale of the Depression, Anxiety and Stress Scale (DASSA). In order to visualize the linear mixed model relating rsEEG-predicted HAMD$_{17}$ change to observed changes in DASSA scores, shown here is a median split on the predicted HAMD$_{17}$ change values. These data demonstrate that the degree of pre-to-post change in DASSA symptoms due to 1 Hz rTMS treatment is greater in those patients with smaller expected HAMD$_{17}$ change scores using the EMBARC-trained sertraline rsEEG model.

Opposite Relationship Between the EMBARC rsEEG Phenotype and Treatment Outcome in a Fourth Independent Study with Combined Repetitive TMS and Psychotherapy Treatment In light of the strength of the EMBARC SELSER rsEEG phenotype indexing cortical responsivity in response to stimulation at several DLPFC locations, we next considered whether the strength of the rsEEG phenotype could predict outcome with repetitive TMS (rTMS) treatment in depression. We studied the relationship between the sertraline-predictive signature and treatment outcome with a separate depression treatment modality in a patient cohort on which pre-treatment rsEEG is available. Analyses were performed on a fourth previously-reported dataset of patients with depression who were treated with at least 10 sessions of simultaneous rTMS and psychotherapy[32,33]. Treatment involved rTMS applied with either a 10 Hz protocol over the left DLPFC (N=64) or a 1 Hz protocol over the right DLPFC (N=88; Example 3). Depression and anxiety symptoms were assessed with the Beck Depression Inventory (BDI) and the three subscales of the Depression, Anxiety and Stress Scale (DASS). We computed each patient's expression of the EMBARC-trained SELSER rsEEG model (expressed as predicted $HAMD_{17}$ change) using the same mean site removal procedure as above. We then tested whether the EMBARC-predicted $HAMD_{17}$ change significantly predicted rTMS-induced change on the BDI and each of the DASS subscales, separately by rTMS protocol, using linear mixed models and a Bonferroni-correction for eight comparisons (two frequencies, four outcome measures). One relationship survived, wherein smaller predicted $HAMD_{17}$ change based on the EMBARC-trained SELSER rsEEG model was associated with greater response to 1 Hz rTMS on the DASS anxiety scale (EMBARC predicted $HAMD_{17}$ change x Time interaction: F(1,128)=9.02, p=0.004; FIG. 7). This suggests that patients who fail to respond to sertraline may be more amenable to the 1 Hz right DLPFC rTMS, providing a potential evidence-based treatment selection approach for depression. This relationship was also specific to 1 Hz right DLPFC rTMS, as we found a treatment protocol x predicted $HAMD_{17}$ change x Time interaction when including both arms in a linear regression (F(1,126)= 4.54, p=0.035).

Discussion

Here we developed a rsEEG-optimized latent space computational model, called Sparse EEG Latent SpacE Regression (SELSER), with which we obtained robust prediction of antidepressant outcome, and moderation (i.e. differential prediction) between outcome with an antidepressant versus placebo in a large placebo-controlled study. The antidepressant-predictive signature identified using SELSER on alpha frequency range eyes open rsEEG data was superior to conventional machine learning models, or latent modeling methods such as ICA or PCA. This signature was furthermore superior to a model trained on clinical data alone and was able to predict outcome on rsEEG data acquired at a study site not included in the model training set and which used a different EEG amplifier and/or electrode montage. Both attributes of our SELSER model support its potential utility in the context of real-world clinical care and with regard to stratification of future depression studies based on the expected antidepressant-specific treatment outcome for that individual. Importantly, the sertraline-predictive SELSER model related to treatment responsiveness/resistance in a second depression sample, suggesting its broad applicability in understanding antidepressant response. We also found evidence of multi-modal convergent validity for our rsEEG antidepressant-response signature by virtue of the correlation between its strength of expression in a third depression data set and expression of a task-based fMRI signature we recently identified in the EMBARC study[22]. Of note, the strength of the rsEEG signature in that data set also correlated with prefrontal neural responsivity, as indexed by direct stimulation with single pulse TMS/EEG. Consistent with this finding, application of the EMBARC-defined SELSER rsEEG model to pretreatment EEG data in a fourth study revealed an opposite relationship between predicted improvement with sertraline and treatment outcome with 1 Hz right DLPFC rTMS given during concurrent psychotherapy. This opposite direction prediction is in-line with our prior work as well as that of others. Most notably, more intact default mode network connectivity in the iSPOT-D study predicted better treatment outcome with antidepressant treatment[34], while more disrupted default mode network connectivity predicted outcome with rTMS in a clinic-based cohort[35]. This finding also opens an exciting avenue for neural signature-driven treatment selection in depression. In addition to the antidepressant-predictive SELSER model, we also identified two somewhat less strong predictive models that were specific to prediction of outcome with placebo using alpha frequency range eyes open and eyes closed rsEEG data.

Figure 18:
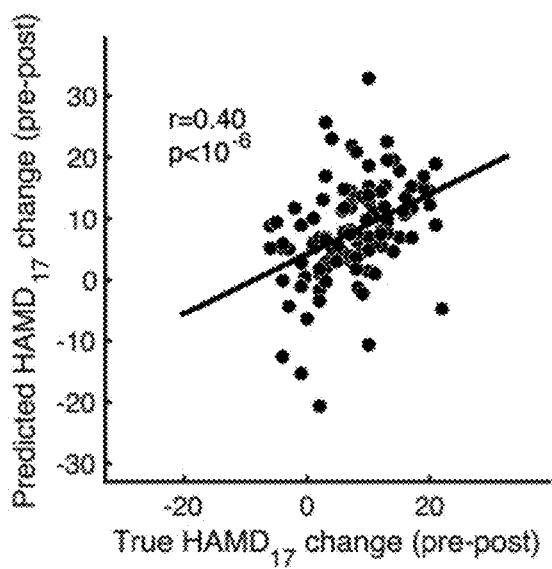

From a neural mechanism perspective, it is striking that the SELSER model revealed both positively and negatively-weighted posterior cortical eyes open rsEEG signals, but only heavily negatively-weighted prefrontal signals. This suggests that posterior signals may contain both components positively and negatively correlated with the treatment outcome, and that optimizing their balance may be what is critical to establishing a robust computational model. Further prediction analysis using electrodes exclusively from posterior regions corroborates this claim (FIG. 18). Our results are broadly in line with prior reports of better outcome being associated with greater posterior cortical alpha power[23]. However, a large-scale study that lacked a placebo control arm failed to replicate these findings[36]. Likewise, we found that a cross-validated relevance vector machine (RVM) trained on channel-level alpha power failed to predict outcome. Thus, the critical element in attaining individual level-robust outcome prediction may be the use of a latent space computational model (i.e. spatial filters optimized by leveraging the treatment outcome information) as done here.

The correlation in our third independent depressed sample of the prediction from the rsEEG model and prefrontal neural responsivity, as assessed through spTMS/EEG stimulation of these regions (but not primary motor or visual cortices), further emphasizes the key contribution of the prefrontal cortex to the treatment-predictive depression phenotype identified here. Considering suggestions that resting alpha power reflects inhibitory tone in a brain region[37,38], the negative weighting of prefrontal alpha in our SELSER model suggests that the prefrontal cortices of better treatment responders are more active or excitable than those of poor responders.

Perhaps somewhat surprising is that only the rsEEG in the eyes open condition, but not in the eyes closed condition, was predictive of the treatment outcome, given that the alpha rhythm is typically even more strongly present in the eyes closed condition. One explanation is that the increasing alpha rhythm (localized predominantly over the occipital cortex) during the eyes closed condition is indicative of cortical areas being deactivated[39], and thus may not provide information for predicting treatment outcome but rather add more background noise to the data, lowering the signal-to-noise ratio. This view was in line with the findings in neurophysiology studies on the motor cortex, where the sensorimotor mu rhythm (covering the same frequency band as alpha) is much weaker than the more broadly distributed alpha rhythm[40]. Therefore, decoding motor intentions requires strengthening differences in the mu rhythm while suppressing the alpha rhythm[41].

The present work does not directly inform the cognitive and emotional information processing relevance of the antidepressant-response rsEEG signature. However, it is notable that its strength of expression correlated in a separate depression sample (Third study) with the strength of expression of a task-based fMRI activation predictive signature also developed in EMBARC based on the brain's ability to regulate the impact of emotional conflict across trials[22]. Thus, individuals with stronger expression of the rsEEG signature may be better able to regulate emotional conflict, which may in part account for why they derive more benefit from an antidepressant over placebo.

Though promising and highly influential signals for antidepressant prediction with rsEEG have been reported for the past two decades[7-9,42], prior work has shown that these signals neither moderate between outcome with an antidepressant versus placebo, nor provide robust individual patient-level prediction. Our results are thus noteworthy in doing both. As such, our data provide neurobiological evidence that an antidepressant-responsive phenotype exists within the biological heterogeneity characteristic of the broader clinical diagnosis of depression. Thus, stratifying patients based on this phenotype can delineate which patients will receive substantial benefit from the antidepressant over placebo and which will not. These findings thereby not only advance a personalized approach to depression[1,5,43], but also demonstrate that antidepressants only appear to be modestly more effective than placebo because they are typically given to an unselected sample of depression patients.

The rsEEG signature we identified may be helpful in deciding whether a patient should continue further medication trials after an initial failure with an antidepressant medication, or switch to treatments with putatively different mechanisms of action (e.g. rTMS, electroconvulsive therapy (ECT), or psychotherapy). Consistent with this use, we found that our rsEEG signature mapped onto the clinical construct of antidepressant treatment resistance in an independent depressed cohort, supporting the generalizability of our findings. Depressed patients often undergo many medication trials before advancing to other treatments such as rTMS[44-4]. This results in potentially avoidable morbidity and economic cost if they are switched to another intervention earlier based on evidence of little expected benefit with an antidepressant using our rsEEG signature. It is therefore noteworthy that the large-scale studies of rTMS treatment for depression have specifically enrolled medication-resistant patients, and showed benefit of real over sham rTMS[46,47]. Our finding of an opposite relationship between predicted change with sertraline and treatment outcome with 1 Hz rTMS and concurrent psychotherapy directly support the potential for these findings to guide treatment selection in depression, pending further replication. Furthermore, as the sertraline-predictive rsEEG signature did not predict outcome with 10 Hz rTMS during concurrent psychotherapy, this suggests that it is the effect of the specific rTMS protocol that is being predicted rather than the effects of psychotherapy. Finally, the rsEEG signature may itself serve as a target for treatment development, aimed at making patients more medication-sensitive.

SELSER is a static latent space modeling approach that does not consider the resting EEG dynamics, despite that a separate model was optimized for each canonical frequency band. Dynamic latent space models have been recently developed to predict mood from multisite intracortical human brain signals[48]. Moreover, static dimensionality reduction and dynamic dimensionality reduction have been used in predicting motor and olfactory states[49,50]. Leveraging EEG dynamics information by incorporating frequency filter optimization into SELSER may further enhance its performance.

In summary, we developed a rsEEG-optimized latent space computation model that was capable of robustly predicting treatment outcome with the antidepressant sertraline and moderating between response to sertraline versus placebo at the individual patient level, and which may support treatment selection between medication and rTMS. Together, these findings ground in individual-level neurobiology a treatment-responsive phenotype obscured within the broader clinical diagnosis of depression and its associated biological heterogeneity, and lay a path towards machine learning-driven personalized approaches to treatment in depression.

REFERENCES FOR EXAMPLE 1

1. Drysdale, A. T. et al. Resting-state connectivity biomarkers define neurophysiological subtypes of depression. Nature medicine 23, 28 (2017).
2. Cipriani, A. et al. Comparative efficacy and acceptability of 21 antidepressant drugs for the acute treatment of adults with major depressive disorder: a systematic review and network meta-analysis. Lancet, doi:10.1016/S0140-6736(17)32802-7 (2018).
3. Fournier, J. C. et al. Antidepressant drug effects and depression severity: a patient-level meta-analysis. JAMA 303, 47-53, doi:10.1001/jama.2009.1943 (2010).
4. Khan, A. & Brown, W. A. Antidepressants versus placebo in major depression: an overview. World Psychiatry 14, 294-300, doi:10.1002/wps.20241 (2015).
5. Kirsch, I. The Emperor's New Drugs: Exploding the Antidepressant Myth. (Random House, 2009).

33

6. Kirsch, I. et al. Initial severity and antidepressant benefits: a meta-analysis of data submitted to the Food and Drug Administration. PLoS Med 5, e45, doi:10.1371/journal.pmed.0050045 (2008).

7. Wade, E. C. & Iosifescu, D. V. Using electroencephalography for treatment guidance in major depressive disorder. Biological Psychiatry: Cognitive Neuroscience and Neuroimaging 1, 411-422 (2016).

8. Widge, A. S. et al. Electroencephalographic Biomarkers for Treatment Response Prediction in Major Depressive Illness: A Meta-Analysis. American Journal of Psychiatry, appi. ajp. 2018.17121358 (2018).

9. Olbrich, S. & Arns, M. EEG biomarkers in major depressive disorder: discriminative power and prediction of treatment response. International Review of Psychiatry 25, 604-618 (2013).

10. Jaworska, N., de la Salle, S., Ibrahim, M.-H., Blier, P. & Knott, V. Leveraging machine learning approaches for predicting antidepressant treatment response using electroencephalography (EEG) and clinical data. Frontiers in psychiatry 9, 768 (2019).

11. Pizzagalli, D. A. et al. Pretreatment Rostral Anterior Cingulate Cortex Theta Activity in Relation to Symptom Improvement in Depression: A Randomized Clinical Trial. JAMA psychiatry 75, 547-554 (2018).

12. Korb, A. S., Hunter, A. M., Cook, I. A. & Leuchter, A. F. Rostral anterior cingulate cortex theta current density and response to antidepressants and placebo in major depression. Clinical Neurophysiology 120, 1313-1319 (2009).

13. Leuchter, A. F., Cook, I. A., Witte, E. A., Morgan, M. & Abrams, M. Changes in brain function of depressed subjects during treatment with placebo. American Journal of Psychiatry 159, 122-129 (2002).

14. Nunez, P. L. & Srinivasan, R. Electric fields of the brain: the neurophysics of EEG. (Oxford University Press, USA, 2006).

15. Müller, K.-R. et al. Machine learning for real-time single-trial EEG-analysis: from brain-computer interfacing to mental state monitoring. Journal of neuroscience methods 167, 82-90 (2008).

16. Wu, W., Nagarajan, S. & Chen, Z. Bayesian Machine Learning: EEG/MEG signal processing measurements. IEEE Signal Processing Magazine 33, 14-36 (2016).

17. Schirrmeister, R. T. et al. Deep learning with convolutional neural networks for EEG decoding and visualization. Human brain mapping 38, 5391-5420 (2017).

18. Haufe, S. et al. On the interpretation of weight vectors of linear models in multivariate neuroimaging. Neuroimage 87, 96-110 (2014).

19. Boyd, S. & Vandenberghe, L. Convex optimization. (Cambridge university press, 2004).

20. Bell, A. J. & Sejnowski, T. J. An information-maximization approach to blind separation and blind deconvolution. Neural computation 7, 1129-1159 (1995).

21. Trivedi, M. H. et al. Establishing moderators and biosignatures of antidepressant response in clinical care (EMBARC): Rationale and design. J Psychiatr Res 78, 11-23, doi:10.1016/j.jpsychires.2016.03.001 (2016).

22. Gregory A. Fonzo, A. E., Yu Zhang, Wei Wu, Crystal Cooper, Cherise Chin-Fatt, Manish K. Jha, Joseph Trombello, Thilo Deckersbach, Phil Adams, Melvin McInnis, Patrick J. McGrath, Myrna M. Weissman, Maurizio Fava, Madhukar H. Trivedi. Brain Regulation of Emotional Conflict Differentiates Response to Antidepressants Versus Placebo in Depression. Nature Human Behaviour (2019).

34

23. Bruder, G. E. et al. Electroencephalographic alpha measures predict therapeutic response to a selective serotonin reuptake inhibitor antidepressant: pre- and post-treatment findings. Biological psychiatry 63, 1171-1177 (2008).

24. Tipping, M. E. Sparse Bayesian learning and the relevance vector machine. Journal of machine learning research 1, 211-244 (2001).

25. Grin-Yatsenko, V. A., Baas, I., Ponomarev, V. A. & Kropotov, J. D. Independent component approach to the analysis of EEG recordings at early stages of depressive disorders. Clinical Neurophysiology 121, 281-289 (2010).

26. Pozzi, D., Golimstock, A., Petracchi, M., Garcia, H. & Starkstein, S. Quantified electroencephalographic changes in depressed patients with and without dementia. Biological psychiatry 38, 677-683 (1995).

27. Iosifescu, D. V. et al. Frontal EEG predictors of treatment outcome in major depressive disorder. European Neuropsychopharmacology 19, 772-777 (2009).

28. Arns, M., Drinkenburg, W. H., Fitzgerald, P. B. & Kenemans, J. L. Neurophysiological predictors of non-response to rTMS in depression. Brain stimulation 5, 569-576 (2012).

29. Tipping, M. E. & Bishop, C. M. Probabilistic principal component analysis. Journal of the Royal Statistical Society: Series B (Statistical Methodology) 61, 611-622 (1999).

30. Hill, A. T., Rogasch, N. C., Fitzgerald, P. B. & Hoy, K. E. TMS-EEG: A window into the neurophysiological effects of transcranial electrical stimulation in non-motor brain regions. Neuroscience & Biobehavioral Reviews 64, 175-184 (2016).

31. Chen, A. C. et al. Causal interactions between fronto-parietal central executive and default-mode networks in humans. Proceedings of the National Academy of Sciences 110, 19944-19949 (2013).

32. Donse, L., Padberg, F., Sack, A. T., Rush, A. J. & Arns, M. Simultaneous rTMS and psychotherapy in major depressive disorder: Clinical outcomes and predictors from a large naturalistic study. Brain stimulation 11, 337-345 (2018).

33. Krepel, N. et al. Non-replication of neurophysiological predictors of non-response to rTMS in depression and neurophysiological data-sharing proposal. Brain Stimulation: Basic, Translational, and Clinical Research in Neuromodulation 11, 639-641 (2018).

34. Williams, L. M., Debattista, C., Duchemin, A., Schatzberg, A. & Nemeroff, C. Childhood trauma predicts antidepressant response in adults with major depression: data from the randomized international study to predict optimized treatment for depression. Translational psychiatry 6, e799 (2016).

35. Liston, C. et al. Default mode network mechanisms of transcranial magnetic stimulation in depression. Biological psychiatry 76, 517-526 (2014).

36. Arns, M. et al. EEG alpha asymmetry as a gender-specific predictor of outcome to acute treatment with different antidepressant medications in the randomized iSPOT-D study. Clinical Neurophysiology 127, 509-519 (2016).

37. Klimesch, W., Sauseng, P. & Hanslmayr, S. EEG alpha oscillations: the inhibition-timing hypothesis. Brain research reviews 53, 63-88 (2007).

38. Jensen, O. & Mazaheri, A. Shaping functional architecture by oscillatory alpha activity: gating by inhibition. Frontiers in human neuroscience 4, 186 (2010).

39. Lehtonen, J. & Lehtinen, I. Alpha rhythm and uniform visual field in man. Electroencephalography and clinical neurophysiology 32, 139-147 (1972).

40. Hari, R. & Salmelin, R. Human cortical oscillations: a neuromagnetic view through the skull. Trends in neurosciences 20, 44-49 (1997).

41. Ramoser, H., Muller-Gerking, J. & Pfurtscheller, G. Optimal spatial filtering of single trial EEG during imagined hand movement. IEEE transactions on rehabilitation engineering 8, 441-446 (2000).

42. Leuchter, A. F. et al. Comparative effectiveness of biomarkers and clinical indicators for predicting outcomes of SSRI treatment in Major Depressive Disorder: results of the BRITE-MD study. Psychiatry Research 169, 124-131 (2009).

43. Kraemer, H. C. Messages for Clinicians: Moderators and Mediators of Treatment Outcome in Randomized Clinical Trials. Am J Psychiatry 173, 672-679, doi:10.1176/appi.ajp.2016.15101333 (2016).

44. Nguyen, K. H. & Gordon, L. G. Cost-Effectiveness of Repetitive Transcranial Magnetic Stimulation versus Antidepressant Therapy for Treatment-Resistant Depression. Value Health 18, 597-604, doi:10.1016/j.jval.2015.04.004 (2015).

45. Voigt, J., Carpenter, L. & Leuchter, A. Cost effectiveness analysis comparing repetitive transcranial magnetic stimulation to antidepressant medications after a first treatment failure for major depressive disorder in newly diagnosed patients—A lifetime analysis. PLoS One 12, e0186950, doi:10.1371/journal.pone.0186950 (2017).

46. O'Reardon, J. P. et al. Efficacy and safety of transcranial magnetic stimulation in the acute treatment of major depression: a multisite randomized controlled trial. Biological psychiatry 62, 1208-1216 (2007).

47. George, M. S. et al. Daily left prefrontal transcranial magnetic stimulation therapy for major depressive disorder: a sham-controlled randomized trial. Archives of general psychiatry 67, 507-516 (2010).

48. Sani, O. G. et al. Mood variations decoded from multisite intracranial human brain activity. Nature biotechnology 36, 954 (2018).

49. Churchland, M. M. et al. Neural population dynamics during reaching. Nature 487, 51 (2012).

50. Cunningham, J. P. & Byron, M. Y. Dimensionality reduction for large-scale neural recordings. Nature neuroscience 17, 1500 (2014).

Example 2: Supplemental Methods for Example 1

Participants and Treatment

Written informed consent was obtained from each participant under institutional review board-approved protocols at each of the four study sites: University of Texas Southwestern Medical Center (TX), Massachusetts General Hospital (MG), Columbia University (CU), and University of Michigan (UM). Data reported here are based on EMBARC participants who were randomly assigned to sertraline or placebo during stage 1 of the trial (N=309 total). Key eligibility for the study included the following: being 18-65 years old; having major depression as a primary diagnosis by the Structured Clinical Interview for DSM-IV Axis I Disorders (SCID)[1]; at least moderate depression severity with a score ≥14 on the Quick Inventory of Depressive Symptomatology-Self Report (QIDS-SR) at screening and randomization; a major depressive episode beginning before age 30; either a chronic recurrent episode (duration ≥2 years) or recurrent MDD (at least 2 lifetime episodes); no antidepressant failure during the current episode. Exclusion criteria included the following: current pregnancy, breastfeeding, no use of contraception; lifetime history of psychosis or bipolar disorder; substance dependence in the past six months or substance abuse in the past two months; unstable psychiatric or general medical conditions requiring hospitalization; study medication contraindication; clinically significant laboratory abnormalities; history of epilepsy or condition requiring an anticonvulsant; electroconvulsive therapy (ECT), vagal nerve stimulation (VNS), transcranial magnetic stimulation (TMS) or other somatic treatments in the current episode; medications (including but not limited to antipsychotics and mood stabilizers); current psychotherapy; significant suicide risk; or failure to respond to any antidepressant at adequate dose and duration in the current episode.

Clinical Trial

EMBARC used a double-blind design, wherein participants were randomized to an 8-week course of sertraline or placebo. Randomization was stratified by site, depression severity, and chronicity using a block randomization procedure. Sertraline dosing began at 50 mg using 50 mg capsules and was increased as tolerated if the patient did not respond until a maximum of 200 mg$^2$. A similar dosing approach was used for placebo capsules.

Clinical Outcome Measure

Our primary outcome was the Hamilton Depression Rating Scale (HAMD$_{17}$). For participants lacking an endpoint HAMD$_{17}$, multiple imputation by chained equations was conducted in R3 using the package mice[4]. The following observed variables were utilized in order to impute endpoint HAMD$_{17}$ values for missing data via Bayesian regression: baseline HAMD$_{17}$, week 1 HAMD$_{17}$, week 2 HAMD$_{17}$, week 3 HAMD$_{17}$, week 4 HAMD$_{17}$, week 6 HAMD$_{17}$, baseline Quick Inventory of Depressive Symptoms (QIDS) total score, baseline Mood and Symptom Questionnaire subscale scores for Anxious Arousal, Anhedonic Depression, and General Distress, Snaith-Hamilton Pleasure Scale (SHAPS) total score, age, years of education, gender, and Wechsler Abbreviated Scale of Intelligence (WASI) t-scores for Vocabulary and Matrix Reasoning.

Resting-State EEG Acquisition

Resting-state EEG (rsEEG) were recorded from each of the four study sites. The EEG amplifier settings are summarized in Table 2. At all study sites, amplifier calibrations were performed. Experimenters were certified by the Columbia EEG team after demonstrating accurate EEG cap placement and delivery of task instructions via video conference, and then submitting satisfactory EEG data from a pilot subject.

TABLE 2

| EEG amplifier settings across study sites for the EMBARC study. | | | | |
| --- | --- | --- | --- | --- |
|  | CU | TX | UM | MG |
| Amplifier | BioSemi | NeuroScan Synamp | NeuroScan Synamp | Geodesic Net |
| # channels | 72 | 62 | 60 | 129 |
| Sampling rate (Hz) | 256 | 250 | 250 | 250 |

TABLE 2-continued

| EEG amplifier settings across study sites for the EMBARC study. | | | | |
|---|---|---|---|---|
| | CU | TX | UM | MG |
| Online filter (Hz) | 0-251.3 | 0-100 | 0.5-100 | 0.01-100 |
| Reference electrode | PPO1, PPO2 | nose | nose | Cz |

Notes for Table 2
CU = Columbia University;
TX = University of Texas Southwestern Medical Center;
UM = University of Michigan;
MG = Massachusetts General Hospital.
For the MG site, EEG data were collected at McLean Hospital.

rsEEG were recorded during four 2-minute blocks (2 blocks for eyes-closed, and 2 blocks for eyes open) in a counterbalanced order. Participants were instructed to remain still and minimize blinks or eye movements, and to fixate on a centrally presented cross during the eyes-open condition.

Resting-State EEG Preprocessing

The recorded rsEEG data were cleaned offline with our in-house fully automated artifact rejection pipeline, thereby minimizing the biases in preprocessing possible with manual rejection of artifacts. The steps are briefly described as follows: 1) The EEG data were resampled to 250 Hz; 2) The 60 Hz AC line noise artifact was identified via the Thompson F-statistic and removed by a multi-taper regression technique[5]. 3) Non-physiological slow drifts in the EEG recordings were removed using a 0.01 Hz high-pass filter; 4) The spectrally filtered EEG data were then re-referenced to the common average; 5) Bad epochs were rejected by thresholding the magnitude of each epoch. Bad channels were rejected based on thresholding the spatial correlations among channels. Subjects with more than 20% bad channels were discarded. The rejected bad channels were then interpolated from the EEG of adjacent channels via the spherical spline interpolation[6]; 6) Remaining artifacts were removed using ICA[7]. ICs related to the scalp muscle artifact, ocular artifact, ECG artifact, were automatically rejected using a pattern classifier trained on expert-labeled ICs from another independent EEG data set; 7) EEG data were re-referenced to the common average. After artifact rejection, 54 EEG channels common to all four study sites were identified and extracted for each subject. Subjects whose total powers across all the channels were beyond three standard deviations of the mean total power were discarded. Consequently, of the 266 patients with pretreatment EEG recordings, 228 had usable EEG data for analyses. The 38 patients with unusable EEG recordings were mainly had too many bad EEG channels and exceedingly large total power across channels.

Second Depression Study Cohort (Validating rsEEG Antidepressant Predictive Signature)

Participants and Treatment

The second depression study was carried out at University of Texas Southwestern Medical Center (UTSW), which is one of the four study sites in EMBARC 8. Written informed consent was obtained under institutional review board-approved protocol at UTSW. Individuals were eligible for the study if they were aged 10 years or older, and had the ability to speak, read, and understand English. To be included, participants needed to have a lifetime or current diagnosis of a mood disorder (i.e., major depressive disorder, persistent depressive disorder, bipolar I/II/NOS, bipolar/mood disorder with psychotic features, depressive disorder other specified (i.e., subthreshold)) based upon a semi-structured diagnostic interview.

Exclusion criteria included the following: history of schizophrenia, schizoaffective disorders or chronic psychotic disorders based upon a semi-structured diagnostic interview; inability to provide a stable home address and contact information; having had any condition for which, in the opinion of the investigator or designee, study participation would not be in their best interest (including but not limited to significant cognitive impairment, unstable general medical condition, intoxication, active psychosis) or that could prevent, limit, or confound the protocol-specified assessments; or requirement for immediate hospitalization for psychiatric disorder or suicidal risk as assessed by a licensed study clinician.

Screening and Baseline Assessments

Whenever possible, screening and baseline assessments took place on the same day and began after informed consent was obtained. A potential participant's eligibility was determined following review of the inclusion/exclusion criteria and assessment with the Mini-International Neuropsychiatric Interview (MINI) diagnostic interview. In addition to a number of self-report symptom measures, which are outside the scope of the current analysis, patient completed the Antidepressant Treatment Response Questionnaire (ATRQ) at the initial visit, which is a self-rated scale for determining treatment resistance in MDD, within the current depressive episode.

Once eligibility requirements were met, baseline procedures were completed over two visits depending on the needs of the individual participant. In the event of a split visit, neuroimaging and EEG procedures might be performed on separate days. This study captured a range of information including socio-demographics, general clinical data, physical exam, blood and stool samples, behavioral testing, neuroimaging and EEG, though here we focus only on the EEG data given the scope of the present study.

Resting-State EEG Acquisition

EEG signals were acquired with two EEG amplifiers, each for a different portion of the participants. The first amplifier was the same 62-channel NeuroScan SynAmps amplifier (NeuroScan Inc., USA) used in EMBARC with identical acquisition parameters. The second amplifier was the Net Amps 300 amplifier with the high-density 256-channel HydroCel Geodesic Sensor Net (Electrical Geodesic Inc., USA). Cz was used as the reference electrode and the sampling rate was set at 1,000 Hz. Electrode impedances were kept below 50 kΩ. A total of 35 and 37 participants' EEG data were collected using the first and second amplifiers, respectively. Participants were seated on a comfortable reclining chair and were instructed to remain awake and let their mind naturally wander in the eyes closed paradigm and then fixate a given point in the eyes open paradigm, each paradigm for two 2-minute blocks.

Resting-State EEG Preprocessing and Analysis

The recorded rsEEG data were cleaned offline with the identical fully automated artifact rejection pipeline as used in EMBARC. After artifact rejection, 54 EEG channels common to all four study sites in EMBARC were identified and extracted for each subject. Subjects whose total powers across all the channels were beyond three standard deviations of the mean total power were discarded.

Third Depression Study Cohort (Correlation Between rsEEG Antidepressant Predictive Signature and fMRI Signature and with TMS/EEG Response to Probe Stimulation)

Participants

Written informed consent was obtained from each participant under institutional review board-approved protocol at Stanford University. Participants in the study underwent several assessments during a clinical intake interview to determine eligibility and classification for the study. The diagnosis of depression (and comorbid conditions) was assessed by a clinician using the SCID, as for EMBARC. Key eligibility for the study included the following: age 18-50 years old; no current psychotherapy; free of metal or ferrous implant; good English comprehension and non-impaired intellectual abilities to ensure understanding of task instructions; no history of neurological disorders, brain surgery, electroconvulsive or radiation treatment, brain hemorrhage or tumor, stroke, epilepsy, hypo- or hyperthyroidism; no daily use of PRN benzodiazepines or opiates (max: 3×/week), or daily thyroid medications, and no antidepressant, anticonvulsant or antipsychotic medications for >2 weeks (fluoxetine >6 weeks). Exclusion criteria included the following: left-handed; did not graduate from an English-speaking high school and English was not their first language; psychiatric medications (including but not limited to antipsychotics and mood stabilizers) and hormonal and/or cancer medications; current psychotherapy; current repetitive transcranial magnetic stimulation (rTMS) treatment or electroconvulsive therapy treatment; loss of consciousness greater than 30 minutes and/or a loss of memory greater than 24 hours; lifetime evidence of psychosis, mania, hypomania, or bipolar disorders and/or manic episodes on the SCID; diagnosis of substance dependence within the past 3 months (but not abuse). 24 subjects for whom resting EEG, single-pulse TMS/EEG, and task fMRI data were all acquired were considered in the subsequent analyses.

Resting EEG Acquisition

EEG recordings were acquired with a BrainAmp DC amplifier (sampling rate: 5 kHz; measurement range: ±16.384 mv; cut-off frequencies of the analog high-pass and Low-pass filters: 0 and 1 kHz) and the Easy EEG cap with 64 extra-flat, freely rotatable, sintered Ag—AgCl electrodes (Brain Products GmbH, Germany). The electrode montage followed an equidistant arrangement extending from below the cheekbone back to below the inion. Electrode impedances were kept below 5 kM. An electrode attached to the tip of the nose was used as the reference. Participants were seated on a comfortable reclining chair and were instructed to remain awake and let their mind wander in the eyes closed paradigm and then fixate a given point in the eyes open paradigm, each 3 minutes. Recordings were immediately assessed for quality using a custom MATLAB (R2014b, The Mathworks Inc., MA) script and rerun if necessary.

Resting-State EEG Preprocessing

The recorded rsEEG data were cleaned offline with the identical fully automated artifact rejection pipeline as used in EMBARC.

Emotional Conflict Task

This well-characterized paradigm assesses both emotional conflict and emotional conflict regulation[8-9]. Each trial involved presentation of an emotional face with either a fearful or happy expression, drawn from the set of Ekman & Friesen[11], with an overlaid emotion word ("FEAR" or "HAPPY"). Participants were instructed to identify the facial emotion with a key press, while trying to ignore the emotion word. The task consisted of 148 trials, with stimuli presented for 1000 milliseconds (ms) in a fast event-related design. Interstimulus intervals were 3000-5000 ms in a pseudo-randomized order counterbalanced for facial expression, gender, word, and response button. Stimuli were either congruent (e.g. fearful face with "FEAR") or incongruent (e.g. fearful face with "HAPPY"), and stimuli were furthermore balanced to achieve an equal fraction of current and prior trial congruency, while ensuring no direct stimulus repetitions. Prior to performance of the task during neuroimaging, all participants underwent a practice version to ensure task proficiency was reached (minimum 80% accuracy) and the task instructions were understood. The neuroimaging task lasted 13 minutes and 14 seconds.

Regulation in the emotional conflict task occurs via an implicit process when conflict trials are preceded by other conflict trials[9,10,12,13]. That is, while emotional conflict results in slowing of reaction times, this effect can be mitigated in incongruent trials that follow incongruent trials (iI trials), compared to incongruent trials that follow congruent trials (cI trials)[9,10]. This trial-to-trial adaptive regulation of emotional conflict reflects an active process by which the brain increases emotional control in response to prior trial conflict, which then benefits regulation of emotional conflict on the subsequent trial (captured by the iI-cI contrast). This regulation effect, captured through the same contrast, has also been extensively described for non-emotional conflict stimuli[14-16]. Critically, this contrast between post-incongruent incongruent and post-congruent incongruent trial compares brain responses to physically identical stimuli (i.e. incongruent trials) that differ only on the relative emotional conflict regulatory context in which they come due to prior trial congruency, and is furthermore independent of the incongruent versus congruent trial (I-C) conflict response contrast. Neuroimaging acquisition parameters are shown in Table 3.

TABLE 3

| Structural MRI and fMRI acquisition scanning parameters for the third MDD study | |
| --- | --- |
| Scanner | General Electric 3T 750 |
| Structural | Series = FSPGR BRAVO |
| | TR/TE = 8.57 ms/3.38 ms |
| | Flip Angle = 15° |
| | Thickness = 1 mm |
| | Resolution = 0.9375 × 0.9375 mm$^2$ |
| | Duration = 5 min |
| fMRI | Spiral in/out acquisition |
| | TR/TE = 2000/30 msec |
| | Flip Angle = 80° |
| | Res. = 3.4375 × 3.4375 mm$^2$ |
| | Thickness = 4.0 mm |
| | Matrix = 64 × 64 | fMRI preprocessing and first-level modeling

FSL tools were used to preprocess imaging data[17,18]. Functional images were first realigned to structural images using an affine registration matrix and boundary-based registration based upon tissue segmentation as implemented in FSL's FLIRT, which was concatenated with a non-linear normalization of each participant's T1 image to the Montreal Neurological Institute (MNI) 152-person 1 mm3 T1 template using FNIRT from FSL 5.0 to result in a single transformation step from individual native functional space to structurally-aligned and spatially-normalized template space. Functional images were realigned to the middle volume of the run. Nuisance signals corresponding to segmented white matter and CSF were regressed out of motion-corrected functional images. A 6 mm full-width half max (FWHM) isotropic smoothing kernel was then applied to preprocessed time series images to account for individual anatomical variability. In order to ensure the quality of imaging measures, we instituted cutoffs for absolute level of motion (root mean square of the absolute level of movement <4 mm across the mean of the squared maximum displacements in each of the 6 translational and rotational parameters estimated during realignment). In addition, in order to ensure brain activation measures reflect task-relevant metrics, we also instituted a minimum level of behavioral accuracy during completion of the emotional conflict task as an additional quality control metric (total accuracy ≥70% of trials correct). Functional runs displaying motion higher than our cutoff OR accuracy below the minimum cutoff were excluded from further analyses.

For individual-level analyses for each participant, regressors modeling trials of interest were convolved with the hemodynamic response function. First-level general linear models were estimated in SPM 8[19]. Regressors corresponded to zero-duration markers set at the onset of stimuli, which were explicitly categorized by congruency (Incongruent or Congruent) and prior trial type (Post-incongruent or Post-congruent) in order to model conflict response and regulation effects. This resulted in 4 different trial types in total, in addition to nuisance regressors for error trials and post-error trials (when applicable) and six motion parameters.

Single-Pulse TMS/EEG Acquisition

Following an anatomical MRI (T1-weghted, 3T) to determine MRI-guided single-pulse TMS (spTMS) targets, subjects received spTMS using a Cool-B B6 5 butterfly coil and a MagPro X100 TMS stimulator (MagVenture, Denmark). Stimulations were delivered to middle primary visual cortex (V1), bilateral primary motor cortices (M1), bilateral dorsolateral prefrontal cortices (pDLPFC), and bilateral anterior DLPFC (aDLPFC) in a randomized order for each subject. Among these stimulation sites, M1 was defined as the hand knob in the standard Montreal Neurological Institute (MNI) space (MNI coordinate: (−38, −18, 64) for left M1 and (40, −18, 64) for right M1). V1 was defined by its MNI anatomical target (MNI coordinate: (0, −100, 2)). For pDLPFC and aDLPFC, the stimulation sites were targeted based on the location of the frontoparietal (executive) control network and ventral attention (salience) network in separate resting-state fMRI data (MNI coordinate: (−32, 42, 34) for left aDLPFC, (30, 50, 26) for right aDLPFC, (−38, 22, 38) for left pDLPFC, and (46, 26, 38) for right pDLPFC). Following our previous work, these targets were established using a group ICA on a separate cohort of 38 participants, with the pDLPFC and aDLPFC targets representing peak voxels within the middle frontal clusters of these two networks[20,21]. Coordinates for the pDLPFC and aDLPFC stimulation targets were then transformed to individual subject native space using non-linear spatial normalization with FSL (website fsl.fmrib.ox.ac.uk/fsl/fslwiki) and used for TMS targeting. The resting motor threshold (rMT) was determined as the minimum stimulation intensity that produced visible finger movement of the right hand at least 50% of the times when the subject's left M1 is stimulated. TMS coil placement was guided by Visor2 LT 3D neuro-navigation system (ANT Neuro, Netherlands) based on co-registration of the functionally defined target to each participant's structural MRI (T1 weighted, slice distance 1 mm, slice thickness 1 mm, sagittal orientation, acquisition matrix 256×256) acquired with a 3T GE DISCOVERY MR750 scanner. The TMS coil was placed in a posterior to anterior direction, with an angle of 45 degrees to the nasion-inion axis. Each target site was stimulated with 60 pulses (biphasic TMS pulses, 280 ρs pulse width, 120% rMT, 1500 ms recharge delay), interleaved at a random interval of 3 s±300 ms. A thin foam pad was attached to the surface of the TMS coil to decrease electrode movement. The subjects were instructed to relax and to fixate at a cross located on the opposing wall while stimulations were administered by a research assistant.

The same TMS-compatible 64-channel BrainAmp DC amplifier as for rsEEG recordings was used to record spTMS/EEG data. Electrode impedances were kept below 5 kΩ. An electrode attached to the tip of the nose was used as the reference. DC correction was manually triggered at the end of the stimulations at each site to prevent the saturation of the amplifier due to the DC drift.

Single-Pulse TMS/EEG Preprocessing

The recorded spTMS/EEG data were cleaned offline with ARTIST, which is a fully automated artifact rejection algorithm for spTMS/EEG[22]: 1) The initial 10 ms data segment following TMS pulses were discarded to remove the large stimulation-induced electric artifact. 2) The EEG data were downsampled to 1 kHz. 3) Big decay artifacts were automatically removed using ICA based on thresholding. 4) The 60 Hz AC line noise artifact was removed by a notch filter. 5) Non-physiological slow drifts in the EEG recordings were removed using a 0.01 Hz high-pass filter, and high-frequency noise was removed by using a 100 Hz low-pass filter. 6) The spectrally filtered EEG data was then re-referenced to the common average and epoched with respect to the TMS pulse (−500~1500 ms). 7) Bad trials were rejected by thresholding the magnitude of each trial. Bad channels were rejected based on the spatial correlations among channels. The rejected bad channels were then interpolated from the EEG of adjacent channels. 8) Remaining artifacts were automatically removed using ICA. ICs related to the scalp muscle artifact, ocular artifact, ECG artifact, were rejected using a pattern classifier trained on expert-labeled ICs from other TMS/EEG data sets.

Fourth Depression Study Cohort (Prediction of Outcome with rTMS Treatment)

Participants

This study was a naturalistic open-label clinical study, and has been previously reported in greater detail elsewhere[23,24]. Briefly, patients were drawn from three outpatient mental health care clinics in the Netherlands (neuroCare Clinic Nijmegen, neuroCare Clinic The Hague, and Psychologen-praktijk Timmers Oosterhout) between May 2007 and November 2016. Inclusion criteria included: 1) a primary diagnosis of non-psychotic MDD or dysthymia, 2) Beck Depression Inventory, second edition, Dutch version (BDI-II-NL)≥14 at baseline, 3) treatment with at least 10 sessions of rTMS over the DLPFC or response within these 10 sessions. All participants signed an informed consent under an approved IRB protocol. Additional exclusion criteria included: previous ECT treatment, epilepsy, traumatic brain injury, current psychotic disorder, wearing a cardiac pacemaker or metal parts in the head, and current pregnancy.

Treatment

All patients were treated with either a high frequency (10 Hz) protocol over the left DLPFC or a low frequency (1 Hz) protocol over the right DLPFC, or both sequentially. The rTMS data included a long time-span and the rTMS protocol applied was never based on clinical symptomatology. In the beginning (2006-2012) the standard protocol applied was 10 Hz left DLPFC rTMS, and only in some cases 1 Hz right DLPFC rTMS was applied (when there were concerns for safety e.g. paroxysmal activity, seizure risk) due to 1 Hz rTMS being considered a safer protocol. On first inspection of those data[25], it was found that the clinical benefits for 10

Hz and 1 Hz were indistinguishable, after which time period the standard protocol became 1 Hz right DLPFC[23]. The analyses reported here focus only on patients that received only 10 Hz or 1 Hz rTMS as too few data sets were available on patients who received both treatments or switched treatments mid-way. There were 73 patients in the 10 Hz arm, of which 64 had high quality EEG data, while in the 1 Hz arm there were 104 patients, of which 88 had high quality EEG data. Selection of the treatment protocol was not done in a randomized manner, but rather in the context of clinical care, and thus each arm is analyzed separately. rTMS was performed using a Magstim Rapid2 (Magstim Company, Spring Gardens, UK) or a Deymed DuoMag XT-100 stimulator with a figure-of-8 coil, 70 mm diameter. For the 10 Hz protocol, rTMS was administered at 10 Hz over the left DLPFC, 110-120% of the resting motor threshold (MT), 30 trains of 5 s duration, inter-train interval (ITI) 30 s, 1500 pulses per session. The 1 Hz protocol consisted of rTMS at 1 Hz over the right DLPFC, 110-120% MT, 120 trains of 10 s duration, ITI 1 s, 1200 pulses per session. In case of both protocols, the LF protocol was administered first with a shorter duration of 1000 pulses per session and subsequently the HF protocol at full length. The DLPFC was localized using either the 5-cm rule or the Beam F3/F4 method[26]. Furthermore, rTMS treatment was complemented with cognitive behavioral psychotherapy by a trained psychologist[27]. Psychotherapy was performed concurrent with the rTMS treatment in 45-minute sessions (the rTMS lasting 20 minutes). Sessions took place with a minimum frequency of two to three times per week and a maximum frequency of two per day, as per the patient's availability.

As these data were drawn from naturalistic clinical care, the total number of sessions depended on clinical decisions, and thus varied across patients. Decisions to continue treatment were based on response to treatment, clinical evaluation of symptom severity, and the patient's own request. Decisions followed several rules: if a BDI decrease was observed of at least 20% from baseline 10 sessions, the treatment was continued, and re-evaluated every five sessions. If no response occurred by session 20-25, treatment was recommended to be terminated unless the patient requested to extend it. If BDI scores reached 12 or below for five sessions, which indicated remission, the patient was given the option of ending or tapering treatment, with an option to extend into maintenance sessions (one session every 6-8 weeks). However, if the threshold of BDI=12 was reached, but symptom improvement continued, treatment was continued until BDI scores ceased improving.

Clinical Outcome Measures

Clinical outcome was assessed on the BDI (which was the primary outcome measure for the decision rules above) as well as the Depression, Anxiety and Stress Scale (DASS)[28]. The DASS is a self-report questionnaire and consists of three subscales: depression (DASSD), anxiety (DASSA), and stress (DASSS). Each scale consists of 14 items with a 4-point severity score, with a maximum total score of 42 on each scale. The patient is asked to fill in the items based on experiences in the previous week.

Resting EEG Acquisition

EEG data were acquired from 26 channels according to the 10-20 electrode international system (Quickcap; NuAmps). Data were referenced to averaged mastoids with a ground at Fpz. The sampling rate of all channels was 500 Hz. A low pass filter with attenuation of 40 dB per decade above 100 Hz was employed prior to digitization. Subjects were asked to rest quietly with their eyes open and eyes closed for 3 minutes each.

Preprocessing of Resting-State EEG and Clinical Outcome Metrics

The recorded rsEEG data were cleaned offline with the identical fully automated artifact rejection pipeline as used in EMBARC. Missing data in the clinical metrics were imputed in the same manner as in the EMBARC data, separately by treatment arm.

Machine Learning Analysis

Sparse EEG Latent Space Regression

We developed a novel end-to-end machine learning algorithm for predicting the treatment outcome from the baseline resting EEG. This new algorithm, referred to as Sparse EEG Latent SpacE Regression (SELSER), optimizes a latent space model that maps the resting EEG data to the treatment outcome by minimizing the prediction error, subject to a constraint on the dimensionality of the latent signals. The band powers in each of the four canonical EEG frequency bands (theta: 4-7 Hz, alpha: 8-12 Hz, beta: 13-30 Hz, gamma: 31-50 Hz; Filtered using zero-phase FIR filters) were employed as the features. Due to the volume conduction, these band power features are best captured in a latent space rather than in the sensor space. For this purpose, SELSER optimizes a set of spatial filters to linearly transform the multi-channel EEG signals in the sensor space to low-dimensional latent signals. A linear regression model is then built to relate the band powers of the latent signals to the treatment outcome.

Figure 16A:
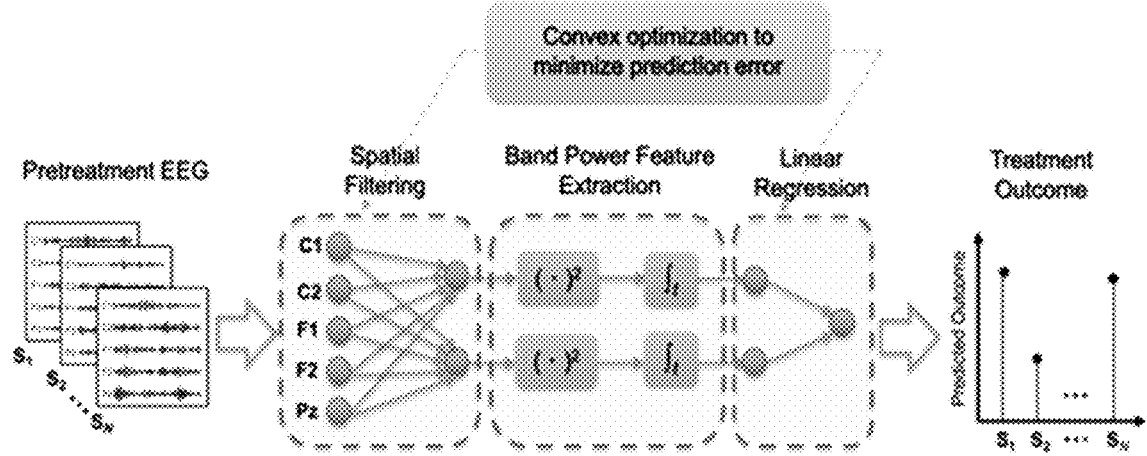
FIGS. 16A-16D. Comparison of different band-power based treatment prediction approaches.

More formally, SELSER models the treatment outcome $y_i$ for the i-th subject as follows (i=1, . . . , M):

$$\hat{y}_i = f\left(X_i; \{w_k\}_{k=1}^L, \{\beta_k\}_{k=1}^L, b\right) = \sum_{k=1}^L \beta_k w_k^T\left[X_iX_i^T/N\right]w_k + b \quad (1)$$

where $X_i \in \mathbb{R}^{C\times N}$ denotes the filtered EEG data for the i-th subject, C is the number of channels, and N is the number of sampled time points. $\hat{y}_i$ denotes the predicted treatment outcome for the i-th subject. $w_k \in \mathbb{R}^C$ is the k-th spatial filter (k=1, . . . , L), $\beta_k$ is the k-th weight coefficient of a linear regression model, and b is the intercept of the linear regression model. As can be seen in FIG. 16A, prediction is carried out in three phases: (1) The multi-channel EEG signals are transformed to L latent signals $\{s_k\}_{k=1}^L$ via L spatial filters $\{w_k\}_{k=1}^L$:$s_k=X_i^Tw_k$. (2) The band powers of the L latent signals $\{z_k\}_{k=1}^L$ are calculated: $z_k=s_k^Ts_k/N$. (3) A linear regression model $\{\beta_k, b\}_{k=1}^L$ is used to combine the band powers of the latent signals to predict the treatment outcome: $\hat{y}_i=\sum_{k=1}^L \beta_kz_k+b$. It is expected that each latent signal captures a certain portion of information predictive of the treatment outcome, quantitated by the band power of the rhythmic EEG activity.

Unlike conventional approaches where the unknown parameters in the spatial filters and regression model, namely $\{w_k, \beta_k, b\}_{k=1}^L$, were optimized separately under distinct objective functions which may or may not be directly associated with the treatment outcome, we proposed a computationally efficient algorithm (see next section) for optimizing all the model parameters by directly minimizing the mean-squared prediction error $\sum_{i=1}^N(\hat{y}_i-y_i)^2$ while preventing L from getting too large to guard against overfitting.

Parameter Optimization in SELSER

Let $C_i=X_iX_i^T/N$ denote the EEG spatial covariance matrix. The predicted treatment outcome can be represented alternatively as the following:

$$\hat{y}_i = \sum_{k=1}^{L} \beta_k w_k^T \left[ X_i X_i^T / N \right] w_k + b = \sum_{k=1}^{L} \beta_k w_k^T C_i w_k + b = Tr\left( W^T C_i \right) + b, \tag{2}$$

where $W = \sum_{k=1}^{L} \beta_k w_k w_k^T \in \mathbb{R}^{C \times C}$ is a symmetric matrix. $Tr(\cdot)$ stands for the trace operator, which takes the sum of the diagonal elements of a matrix. Suppose the spatial filters $\{w_k\}_{k=1}^{L}$ are orthogonal to each other, then $\{w_k\}_{k=1}^{L}$ and $\{\beta_k\}_{k=1}^{L}$ are the eigenvectors and eigenvalues of $W$, respectively. As a result, optimizing $\{w_k\}_{k=1}^{L}$ and $\{\beta_k\}_{k=1}^{L}$ amounts to optimizing $W$, after which $\{w_k\}_{k=1}^{L}$ and $\{\beta_k\}_{k=1}^{L}$ can be obtained by performing eigendecomposition of $W$.

However, the number of unknown parameters in $W$, $C(C+1)/2$, is typically much larger than the number of training samples, hence simply minimizing the prediction error is prone to model overfitting. To address this issue, in addition to minimizing the prediction error, we added the rank of $W$, which is equal to $L$, as a penalty term into the objective to limit the dimensionality of the latent signals, yielding the following optimization problem:

$$\min_{W,b} \sum_{i=1}^{M} (\hat{y}_i - y_i)^2 + \lambda \|W\|_0 \tag{3}$$

where $\|W\|$ denotes the rank of $W$. However, Problem (3) is NP-hard and the rank penalty is non-smooth. Alternatively, the following nuclear norm has been widely used as a convex surrogate of the rank of matrices in a wide range of applications in signal processing and machine learning[29-32]:

$$\|W\|_1 = \sum_{k=1}^{L} \sigma_k, \tag{4}$$

where $\{\sigma_k\}_{k=1}^{L}$ are the singular values of $W$. Consequently, replacing $\|W\|_0$ with $\|W\|_*$, yields $$\min_{W,b} \sum_{i=1}^{M} (\hat{y}_i - y_i)^2 + \lambda \|W\|_* \tag{5}$$

Problem (5) is a convex optimization problem[33] since the objective function is a convex function of $W$ and $b$. This allows us to use a range of contemporary optimization algorithms such as the interior point method[33] to find the global minimum solution. or the accelerated proximal gradient method (APGM)[34] to find the global minimum solution. To solve Problem (5), the APGM only requires the calculation of gradients and the singular value decomposition (SVD) in each iteration, hence is scalable to large data sets. Below we provide the derivation of the algorithm.

Let $h(W,b) = \sum_i (\hat{y}_i - y_i)^2$ and $g(W) = \lambda \|W\|_*$, we note that $h(W,b)$ is a differentiable function with respect to $W$ and $b$, whereas $g(W)$ is a non-smooth function of $W$. Instead of directly minimizing $h(W,b) + g(W)$, the proximal gradient method iteratively updates $W$ and $b$ with the following rule:

$$\{W(t+1), b(t+1)\} = \operatorname*{argmin}_{W,b} G_{\mu(t)}(\{W, b\}, \{W(t), b(t)\}), \tag{6}$$

where $G_{\mu(t)}(\{W, b\}, \{W(t), b(t)\}) = h(W(t), b(t)) +$

-continued $$Tr\Big( [\nabla_W h(W(t), b(t))]^T (W - W(t)) + \nabla_b h(W(t), b(t))(b - b(t)) +$$

$$1/2\mu(t)(\|W - W(t)\|)_F^2 + 1/2\mu(t)(b - b(t))^2 + g(W),$$

$$\nabla_W h(W(t), b(t)) = 2\sum_i \left( Tr\left( W^T(t) C_i \right) + b(t) - y_i \right) C_i,$$

$$\nabla_b h(W(t), b(t)) = 2\sum_i \left( Tr\left( W^T(t) C_i \right) + b(t) - y_i \right),$$

$\mu(t)$ is the step size at the t-th iteration that can be determined by the line search[35], and $W(t)$ and $b(t)$ are the values of $W$ and $b$ obtained at the t-th iteration.

By ignoring the terms independent of $W$ and $b$, we can further write (6) as $$\{W(t+1), b(t+1)\} = \tag{7}$$

$$\operatorname*{argmin}_{W,b} \frac{1}{2\lambda\mu(t)} \|W - U(t)\|_F^2 + \frac{1}{2\lambda\mu(t)} (b - s(t))^2 + \|W\|_*,$$

where $U(t) = W(t) - \mu(t)\nabla_W h(W(t), b(t))$ and $s(t) = b(t) - \mu(t)\nabla_b h(W(t), b(t))$. Since $W$ and $b$ are separable in Problem (6), we have $$b(t+1) = s(t), \tag{8}$$

$$W(t+1) = \operatorname*{argmin}_{W} \frac{1}{2\lambda\mu(t)} \|W - U(t)\|_F^2 + \|W\|_*. \tag{9}$$

Problem (8) can be solved by soft-thresholding the singular values of $U(t)$[36]. More specifically, if $U(t) = U\Sigma V^T$ is the SVD of $U(t)$, then $$W(t+1) = U\Sigma_{\lambda\mu(t)} V^T, \tag{10}$$

where $(\Sigma_{\lambda\mu(t)})_{ii} = \max\{\Sigma_{ii} - \lambda\mu(t), 0\}$.

Notably, the convergence of the above iterations can be accelerated by smoothing $W(t)$ and $b(t)$ prior to (6)[37]:

$$W(t) = W(t) + \frac{\alpha(t-1) - 1}{\alpha(t)} (W(t) - W(t-1)) \text{ and}$$

$$b(t) = b(t) + \frac{\alpha(t-1) - 1}{\alpha(t)} (b(t) - b(t-1)).$$

The detailed optimization procedure for the APGM for solving Problem (5) is summarized in Table 4. This algorithm achieves a convergence rate of $O(1/I^2)$, where I is the maximum number of iterations. To remove the inter-subject variability due to the overall power variation, for each subject $C_i$ is normalized by dividing its trace prior to the SELSER analysis: $C_i = C_i / Tr(C_i)$.

Relevance Vector Machine

To compare with SELSER, Relevance Vector Machine (RVM)[38] with the linear kernel was used to build sparse linear regression models for treatment prediction from non-SELSER optimized features. By leveraging a sparse prior to penalize overly complex models under the sparse Bayesian learning framework, RVM is able to automatically select relevant features for prediction via marginal likelihodd maximization. Hence, RVM obviates the need of additional validation data to determine the hyperparameters. In the past decades, RVM has demonstrated its strength in various fields including EEG classification for brain-computer interface[39] and bioinformatics analysis of gene expression data[40,41].

Treatment Prediction Using SELSER

We applied SELSER to each canonical EEG frequency band to predict the treatment outcome. In order to increase the sample size, each of the two blocks of EEG in each resting-state condition (eyes open or eyes closed) was treated as a separate sample for training the model. However, during the leave-subject-out cross-validation, the two blocks from each subject were always grouped together such that if one block was included in the training set, the other was included as well. The predicted outcome of each subject was the average of the predicted outcomes of the two EEG blocks from the subject.

Visualizing Spatial Maps of Latent Signals

Each latent signal has a spatial map that could be visualized on both the scalp and cortical surface to facilitate neurophysiological interpretation. The scalp spatial maps could be calculated as follows[42]:

$$A_s = \overline{C} \cdot V \cdot \overline{C}_z \qquad (11)$$

where $A_s \in \mathbb{R}^{C \times L}$ contains the scalp spatial maps of the latent signals as columns, $\overline{C} = \Sigma_{i=1}^{N} C_i \in \mathbb{R}^{C \times C}$ is the mean spatial covariance matrix of the EEG signals across subjects, $V = [w_1, \ldots, w_L] \in \mathbb{R}^{C \times L}$, and $\overline{C}_z = V^T \overline{C} V \in \mathbb{R}^{L \times L}$ is the mean covariance matrix of the latent signals across subjects.

In order to obtain the cortical spatial maps of the latent signals, a three-layer (scalp, skull, and cortical surface) boundary element head model was computed with the OpenMEEG plugin[43] based on FreeSurfer average brain template[44]. A total of M (M=15,002) fixed-orientation dipoles whose orientations were normal to the cortical surface were generated. The lead-field matrix $B \in \mathbb{R}^{M \times C}$ relating the dipole activities to the EEG was obtained as a result of the boundary element modeling. A linear inverse matrix $\in \mathbb{R}^{C \times M}$ that maps the EEG signals to the cortical sources was then computed via the sLORETA algorithm[45]. The cortical spatial maps could subsequently be calculated as follows:

$$A_c = H \cdot A_s \qquad (12)$$

where $A_c \in \mathbb{R}^{M \times L}$ contains the cortical spatial maps of the latent signals as columns.

The spatial maps used for visualization were obtained by training SELSER on the entire EMBARC sample.

Treatment Prediction Using the Channel-Level Alpha Band Power or Theta Cordance Features To contrast with prediction approaches based on channel-level measures, we trained the RVM using the channel-level alpha band power[46] (FIG. 16C) and theta cordance[47] features, respectively. Cordance is a quantitative EEG (QEEG) measure that has been implicated as a predictive biomarker for antidepressant treatment[25,46,48]. In particular, it was reported that lower prefrontal theta cordance during the placebo lead-in phase predicted better antidepressant (fluoxetine, which is an SSRI, and venlafaxine, which is an SNRI) treatment outcome[49]. Theta cordance was calculated for each participant via the following steps: 1) EEG power re-attribution: Absolute re-attributed theta power of each electrode was calculated as the average of the theta band (4-7 Hz) power of all bipolar neighboring electrode pairs that share that electrode, and absolute re-attributed total power of each electrode was calculated as the average of the total (1-50 Hz) power of all bipolar neighboring electrode pairs that share that electrode. Relative re-attributed power of each electrode was calculated as the absolute re-attributed theta power divided by the average of the absolute re-attributed total power. 2) Spatial normalization: The absolute and relative re-attributed theta power values were each normalized by their average across channels. 3) Combination of absolute and relative power: Theta cordance was calculated as the sum of the spatially normalized absolute and relative re-attributed theta power.

Treatment Prediction Using Band Power Features of the Latent Signals Extracted with Independent Component Analysis or Principal Component Analysis SELSER was also benchmarked against prediction approaches using band power features of the latent signals estimated by Independent component analysis (ICA)[50] and principal component analysis (PCA)[51], respectively. ICA and PCA are widely used unsupervised approaches for estimating latent signals from EEG signals[52,53], based on different statistical criteria—statistical independence is maximized among latent signals in ICA, while variance of the latent signals is maximized in PCA. Over the years, a multitude of ICA algorithms have been developed as statistical independence could be quantified in a variety of ways[54]. In this work, we used the information maximization (Infomax) algorithm[7] for performing ICA.

Figure 16B:
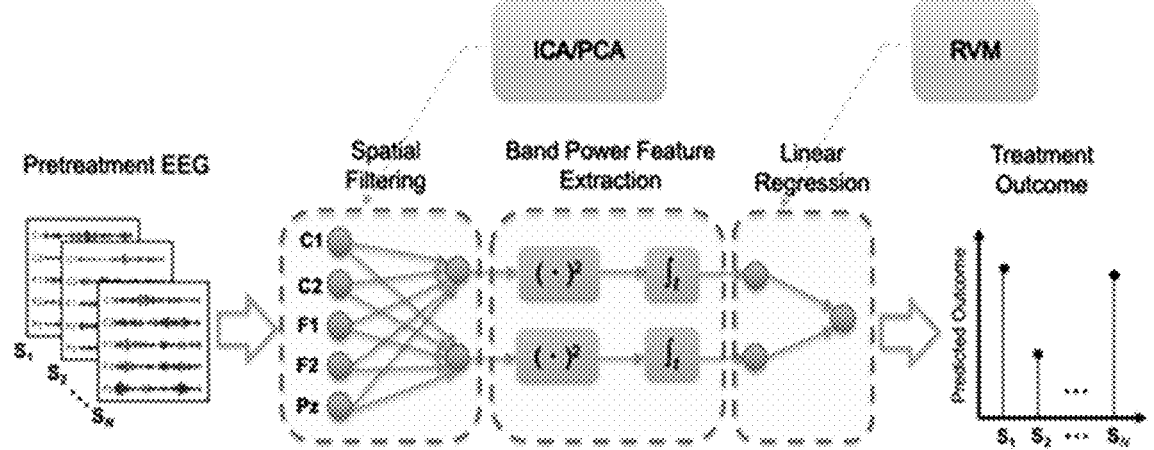
Figure 16C:
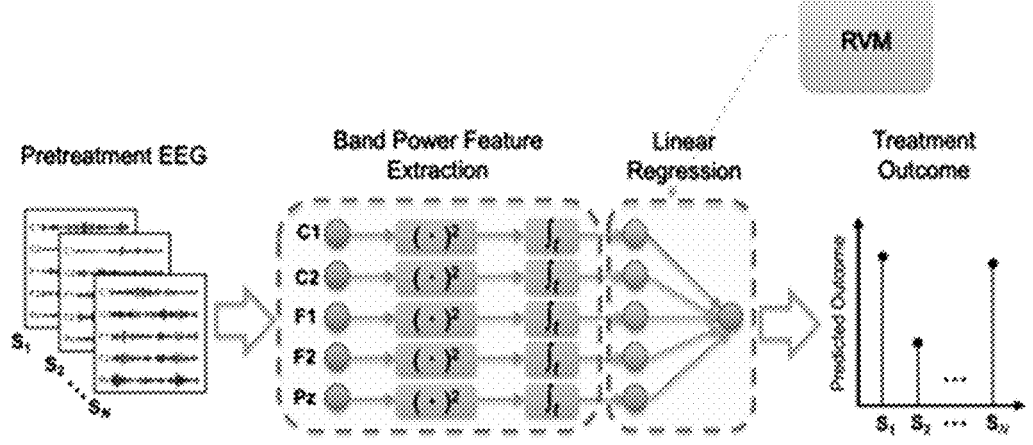

To align with the SELSER analyses, the prediction framework based on ICA/PCA followed the same workflow as in SELSER (FIG. 16B). Each subject's EEG signal was first normalized by dividing the square root of its total power across channels. The latent signals were then estimated by using ICA or PCA to temporally concatenated EEG signals across subjects. After that, the band powers of the full set of latent signals were computed as the features, followed by an RVM with the linear kernel that related the band power features to the HAMD$_{17}$ score changes.

Figure 16D:
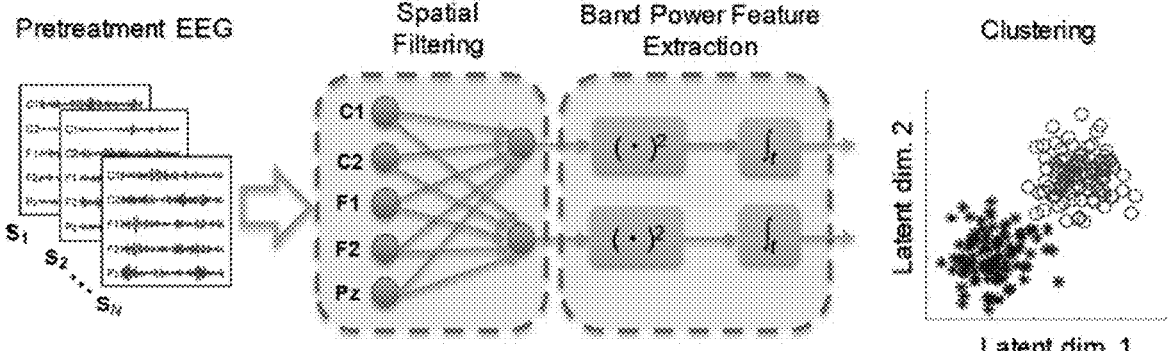

FIG. 16D depicts another example application of SELSER in which the latent signals generated by the application of the optimized spatial filters are clustered based on the band power of the latent signals. As noted, the band power of the latent signals generated by the application of the optimized spatial filters may be most predictive of treatment outcome. Instead of and/or in addition to being fed into a linear regression model, the band power of the latent signals associated with a plurality of subjects (e.g., an N quantity of subjects) may be clustered by applying a clustering algorithm such as, for example, k-means, Gaussian mixture, and/or the like. Each of the resulting clusters may correspond to a type and/or subtype of disease.

In some example embodiments, a patient may be diagnosed as having a type and/or a subtype of disease based at least on the latent signals derived from the EEG data of the patient. For example, latent signals for the patient may be derived by at least applying the optimized spatial filters to the patient's EEG data. A diagnosis for the patient may be determined based at least on a distance (e.g. Euclidean distance, Mahalonobis distance, and/or the like) between the band power of these latent signals and one or more of the clusters. For instance, the patient may be diagnosed as having a type of disease and/or a subtype of disease based at least on the band power of the patient's latent signals being closest to and/or within a threshold distance of a cluster corresponding to that type and/or subtype of disease.

Figure 19:
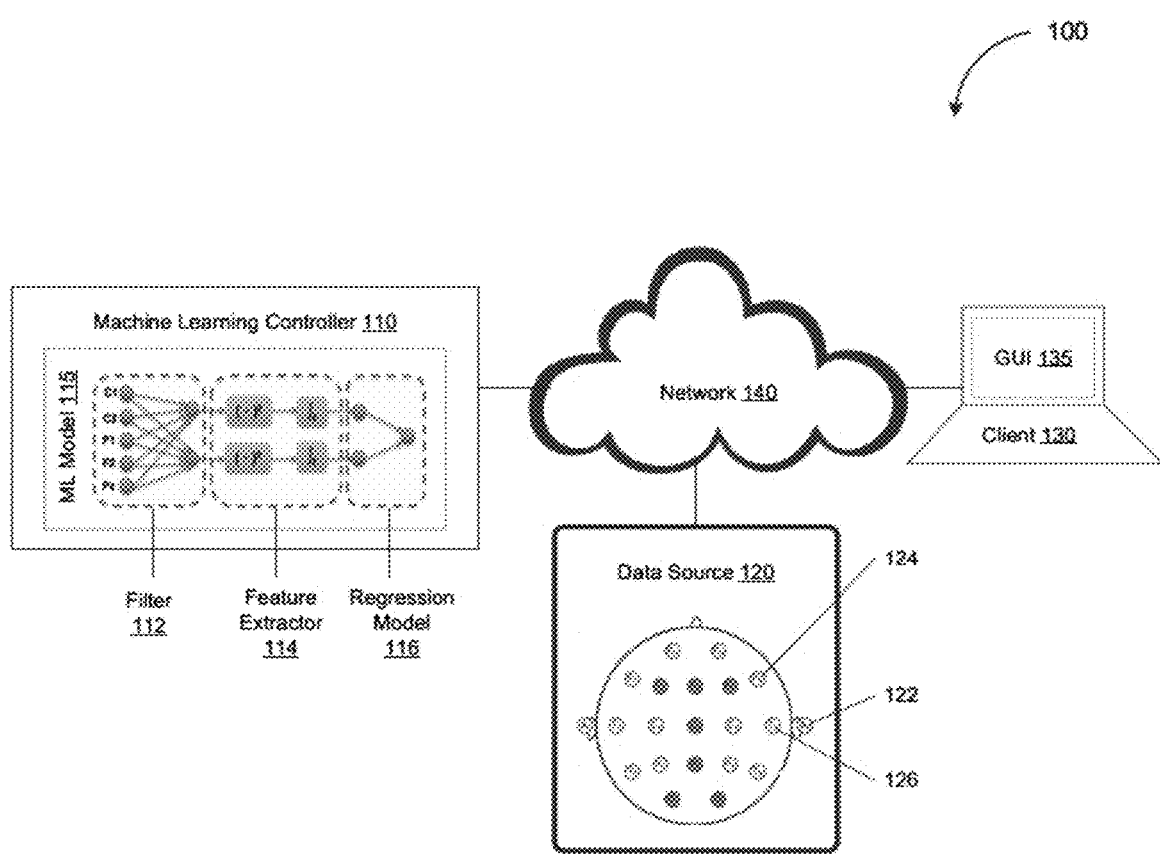
FIG. 19 depicts a system diagram illustrating an example of a machine learning based EEG data processing system, in accordance with some example embodiments.

FIG. 19 depicts a system diagram illustrating an example of a machine learning based data processing system 100, in accordance with some example embodiments. Referring to FIG. 19, the machine learning based data processing system 100 may include a machine learning controller 110, a data source 120, and a client 130. As shown in FIG. 1, the machine learning controller 110, the data source 120, and the client 130 may be communicatively coupled via a network 140. The network 140 may be a wired and/or wireless network including, for example, a local area network (LAN), a virtual local area network (WLAN), a wide area network (WAN), a public land mobile network (PLMN), the Internet, and/or the like.

In some example embodiments, the data source 120 may include a device having one or more sensors capable of collecting brain signals from one or more regions of the brain of a subject. These brain signals may be representative of electrical activities within the brain of the subject. In the example shown in FIG. 19, the data source 120 may include an EEG device having a plurality of electrodes including, for example, a first electrode 122, a second electrode 124, and a third electrode 126. However, it should be appreciated that the data source 120 may include any device capable of collecting brain signals including, for example, a transcranial magnetic stimulation (TMS) electroencephalography (EEG) device, a magnetoencephalography (MEG) device, a functional magnetic resonance imaging (fMRI) device, a functional near-infrared spectroscopy (fNIRS) device, and/or the like. That is, the machine learning controller 110 may receive, from the data source 120, a variety of data corresponding to brain signals including, for example, EEG data, TMS-EEG data, MEG data, fMRI data, fNIRS data, and/or the like. As such, instead of and/or in addition to brain signals representative of the electrical activities within the brain of the subject, the data source 120 may provide brain signals representative of other activities including, for example, magnetic fields, blood flow, hemoglobin (Hb) concentrations, and/or the like.

In the EEG device example, the plurality of electrodes may be configured to measure electrical activities within the brain of the subject. For example, the first electrode 122 may serve as a reference electrode while the second electrode 124 and/or the third electrode 126 may each serve as a recording electrode. As shown in FIG. 19, the plurality of electrodes, including the first electrode 122, the second electrode 124, and the third electrode 126, may be placed along the surface of the scalp of the subject and/or implanted beneath the scalp of the subject in order to measure the electrical activities within the brain of the subject. The EEG device may be configured to measure electrical activities (e.g., triggered by one or more transcranial magnetic stimulation (TMS) stimuli) including by outputting EEG data that includes one or more scalp maps and/or waveforms for each channel of the EEG device.

As used herein, a channel may refer to the recorded voltage differential between a reference electrode and a recording electrode. For instance, the EEG device may provide a first channel that records the voltage differential between the first electrode 122 and the second electrode 124 as well as a second channel that records the voltage differential between the first electrode and the third electrode 126. The voltage differential recorded at every channel of the EEG device at a particular point in time $t_i$ may be mapped to a corresponding scalp map showing a spatial distribution of the voltage differentials measured across the entire scalp of the subject at that particular time $t_i$. Meanwhile, the waveform associated with a particular channel (e.g., the first channel or the second channel) may reflect the temporal distribution of voltage differentials over that channel across a certain period of time.

In some example embodiments, the machine learning controller 110 may be configured to process one or more representations of data corresponding to the brain signals received from the data source 120. For example, the machine learning controller 110 may process a spatial covariance matrix that provides one representation of EEG data by at least summarizing a spatial distribution of the electrical activities detected across different channels of the EEG device. However, it should be appreciated that the machine learning controller 110 may process other representations of brain signals. For instance, the machine learning controller 110 may process one or more covariance matrices summarizing a frequency distribution and/or a power distribution the EEG data.

Referring again to FIG. 19, the machine learning controller 110 may include a machine learning model 115 including a filter 112, a feature extractor 114, and a regression model 116. The machine learning controller 110 may be configured to train the machine learning model 115 including, for example, by solving a convex optimizing problem to optimize the filter 112 to generate a reduced quantity of latent signals whose features minimize the prediction error of the regression model 116. For example, the filter 112 may be optimized to generate a quantity of latent signals that is lesser than the quantity of signals included in the data corresponding to the brain signals received from the data source 120 but whose features still minimize the prediction error of the regression model 116. Alternatively, the reduced quantity of latent signals may be a minimum quantity of latent signals whose features minimize the prediction error of the regression model 116.

The machine learning model 115 may be trained based on training data that includes one or more representations of brain signals collected from a plurality of subjects. The one or more representations of brain signals may include, for example, one or more covariance matrices summarizing a spatial distribution, a frequency distribution, and/or a power distribution of EEG data. The training data may further include a treatment outcome associated with each of the plurality of subjects. For example, the treatment outcome associated with each of the plurality of subjects may include the results of one or more symptom assessments, behavioral tests, psychological tests, and/or the like. As such, training the machine learning model 115 may include optimizing the filter 112 to generate a minimum quantity of latent signals whose features minimize a difference between the treatment outcome prediction output by the regression model 116 and the actual treatment outcomes of the subjects.

In some example embodiments, the regression model 116 may be trained to generate a treatment prediction outcome based on one or more features extracted by the feature extractor 114. Examples of the features extracted by the feature extractor 114 may include band power (e.g., power within a specific oscillatory band), power-envelope connectivity (e.g., correlation coefficients between the power envelopes of two regions of the brain), weighted phase-lag index (e.g., measuring a coherence between the EEG phases of two regions of the brain), imaginary coherence (e.g., an imaginary part of the spectral coherence between the EEG data of two regions of the brain), cordance (e.g., a combination of absolute power and relative power of different EEG frequencies), approximate entropy (e.g., a measure for quantifying the amount of regularity and unpredictability of fluctuations in the EEG data), Shannon entropy (e.g., a measure for quantifying statistical uncertainty in EEG data), cross-frequency coupling (e.g., a measure for quantifying interaction between oscillations at different frequency bands), and/or the like.

In some example embodiments, the one or more representations of brain signals from the data source 112 may be high-dimensional data whose quantity of features exceeds the quantity of available training data. For example, EEG data may be associated with a high spatial-temporal dimensionality due to the phenomenon of volume conduction. That is, the electrical activity that is recorded by an EEG device may be blurred, especially at the scalp level, because the activity that is recorded by each electrode may originate from a mixture of underlying brain sources. The high-dimensionality of the unprocessed EEG data may cause overfitting at the regression model 116. As such, the filter 112 may be configured to reduce the dimensionality of the EEG data including by merging two or more signals to generate a single latent signal. Two or more signals may be merged based at least on the two or more signals exhibiting an above threshold positive covariance, for example, by changing (e.g., increasing and/or decreasing in value) in tandem.

In some example embodiments, the machine learning controller 110 may train the machine learning model 115 to process one or more representations of EEG data including, for example, a spatial covariance matrix summarizing a spatial distribution of the EEG data. Accordingly, the machine learning model 115 may be trained by at least optimizing the filter 112 to generate a minimum quantity of latent signals whose feature may be used by the regression model 116 to generate a treatment outcome prediction having a minimum error. In instances where the machine learning model 115 processes EEG data represented by a spatial covariance matrix, the feature extractor 114 may be configured to extract a band power of each of the latent signals generated by the filter 112. However, as noted, the feature extractor 114 may be configured to extract other features of the latent signals generated by the filter 112 including, for example, power-envelope connectivity, weighted phase-lag index, imaginary coherence, cordance, approximate entropy, Shannon entropy, cross-frequency coupling, and/or the like.

As used herein, the treatment outcome prediction generated by the regression model 116 may include a measure of how much a patient responds to treatments to obtain a beneficial or desired result (e.g., clinical result) in a subject's condition. Examples of treatments include a variety of modalities including, for example, medications (e.g., antidepressants), psychotherapy, somatic therapy (e.g., electroconvulsive therapy (ECT), vagal nerve stimulation (VNS), transcranial magnetic stimulation (TMS)), and/or the like. The patient's response to the treatment may include alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. An error in the treatment outcome prediction may include a difference between the outcome predicted by the regression model 116 and an actual treatment outcome observed in a subject undergoing the treatment.

The trained machine learning model 115 may be trained and deployed for a variety of applications. For example, the machine learning model 115 may be trained on (and subsequently applied to) data including one or more representations of the brain signals of a patient to predict a treatment outcome for the patient. The data may include representations of a first plurality of brain signals measured at a first time $t_1$ prior to any treatment (e.g., medication, psychotherapy, somatic therapy) and/or a second plurality of brain signals measured at a second time $t_2$ subsequent to one or more treatments. Alternatively and/or additionally, the data may include a difference between brain signals measured at various times before, during, and/or after treatment. For instance, the data may include a difference between the first plurality of brain signals measured at the first time $t_1$ prior to any treatment (e.g., medication, psychotherapy, somatic therapy), the second plurality of brain signals measured at the second time $t_2$ subsequent to one or more treatments, and/or a third plurality of signals measured at a third time $t_3$ during the one or more treatments. In this case, the machine learning model 115 may be trained to detect correlations between changes in brain signals and changes in the patient's symptoms including, for example, changes induced by the administration of one or more treatments.

In some example embodiments, the trained machine learning model 115 may be configured to generate a treatment outcome prediction indicating a patient's response to one or more treatments. For example, the treatment outcome prediction from the trained machine learning model 115 may identify the patient as being responsive to one or more types of medication, psychotherapy, somatic therapy, and/or the like.

In some example embodiments, the trained machine learning model 115 may enable a differentiation between the relative benefits of different treatments including by generating a treatment outcome prediction indicating a patient's responses to multiple modalities treatments such as, for example, medication, psychotherapy, somatic therapy, and/or the like. Alternatively and/or additionally, the trained machine learning model 115 may further enable a differentiation between the relative benefits of different varieties of the same treatment including, for example, different types of medication, psychotherapies, somatic therapies, and/or the like. For example, the treatment outcome prediction from the trained machine learning model 115 may indicate the patient as exhibiting a first quantity of improvement when subject to a first modality of treatment (e.g., medication) and a second quantity of improvement when subject to a second modality of treatment (e.g., somatic therapy). The specific modalities and/or types of treatments that should be administered to the patient may be determined based at least on the relative benefits of the different treatments.

Alternatively and/or additionally, the trained machine learning model 115 may be configured to generate a treatment outcome prediction indicating a patient's response to a placebo and/or a sham treatment (e.g., sham rTMS). Whether the patient may benefit from a particular treatment (e.g., medication, psychotherapy, somatic therapy, and/or the like) may be determined based on a different between the patient's predicted response to a treatment relative to the patient's predicted response to the placebo. For example, the trained machine learning model 115 may determine that the patient exhibits a first quantity of improvement when subject to the treatment and a second quantity of improvement when subject to a corresponding placebo. The patient may be administered the treatment if a difference between the first quantity of improvement and the second quantity of improvement exceeds a threshold value.

Alternatively and/or additionally, the trained machine learning model 115 may also be configured to generate, based at least on data including one or more representations of the brain signals of the patient, a diagnosis for the patient. For example, as shown in FIG. 15D, a plurality of subjects may be clustered based on one or more features (e.g., band power) of the brain signals associated with each of the plurality of subjects. Further as shown in FIG. 15D, each cluster may correspond to a type and/or a subtype of disease. Accordingly, the filter 112 of the trained machine learning model 115 may be applied to data including one or more representations of the brain signals of the patient (e.g., a spatial covariance matrix representative of the patient's EEG data) to generate latent signals whose features (e.g., band power) are most predictive of treatment outcome. The patient may be diagnosed as having a type and/or subtype of disease based at least on a distance (e.g. Euclidean distance, Mahalonobis distance, and/or the like) between the features of these latent signals and one or more of clusters, each of which corresponding to a type and/or subtype of disease. The diagnosis for the patient (e.g., as having a type and/or subtype of disease) may also be displayed, for example, by the graphical user interface 135 at the client 130.

FIG. 20 depicts a flowchart illustrating an example of a process 200 for machine learning based EEG data processing, in accordance with some example embodiments. Referring to FIGS. 19-20, the process 200 may be performed, for example, by the machine learning controller 110.

The machine learning controller 110 may train a machine learning model including by optimizing a spatial filter to generate, based on training data including EEG data and a treatment outcome associated with a plurality of subjects, a minimum quantity of latent signals whose band power minimizes an error in a treatment outcome prediction generated by a regression model (202). In some example embodiments, the machine learning controller 110 may be configured to train the machine learning model 115 based on training data including EEG data for a plurality of subjects. For example, as shown in FIGS. 16A-16B, the machine learning model 115 may be trained based on EEG data for an N quantity of subjects including subjects S_1, S_2, . . . ,S_N. The machine learning model 115 may be trained by at least optimizing the filter 112 to generate a minimum quantity of latent signals whose band powers may be used by the regression model 116 to generate a treatment outcome prediction for the plurality of subjects with a minimum error. For instance, the machine learning controller 110 may train the machine learning model 115 by solving a convex optimization problem that includes a penalty term to limit the dimensionality of the latent signals. The global minimum solution to the convex optimization problem may therefore minimize the error in the prediction generated by the regression model 116 as well as minimize the quantity of latent signals generated by the filter 112. In some example embodiments, the trained machine learning model 115 may be deployed to a production environment. It should be appreciated that the trained machine learning model 115 may be deployed in any form. For example, the trained machine learning model 115 may be deployed as computer software including as a stand-alone program or as a module, component, subroutine, or other unit suitable for use in a computing environment. Alternatively and/or additionally, the trained machine learning model 115 may be deployed as hardware including, for example, application specific integrated circuits (ASICs), field-programmable gate arrays (FPGAs), and/or the like. Once deployed, the trained machine learning model 115 may be accessed in any manner including, for example, as part of a web service, a cloud-based service (e.g., a software-as-a-service (SaaS)), a mobile application, and/or the like.

The machine learning controller 110 may receive EEG data for a patient (204). For example, the machine learning controller 110 may receive, from the EEG device 120, EEG data for a patient.

The machine learning controller 110 may determine a diagnosis and/or a treatment outcome prediction for the patient by at least applying, to the EEG data for the patient, the trained machine learning model (206). In some example embodiments, the machine learning controller 110 may apply, to the EEG data received from the EEG device 120, the trained machine learning model 115 in order to generate a treatment outcome prediction for the patient based on the EEG data of the patient. The trained machine learning model 115 may include the filter 112, which has been optimized to generate, based on the EEG data associated with the patient, a minimum quantity of latent signals whose band signals may be extracted by the feature extractor 114 and used by the regression model 116 to generate a treatment prediction outcome with minimal error.

Alternatively and/or additionally, the machine learning controller 110 may be applied to the trained machine learning model 115 in order to determine a diagnosis for the patient as having a type and/or subtype of disease. For example, the filter 112 of the trained machine learning model 115 may be applied to the EEG data of the patient to generate latent signals whose band powers are most predictive of treatment outcome. The patient may be diagnosed as having a type and/or subtype of disease based at least on a distance (e.g. Euclidean distance, Mahalonobis distance, and/or the like) between the band power of these latent signals and one or more of clusters, each of which corresponding to a type and/or subtype of disease. The predicted treatment outcome and/or the diagnosis for the patient may be displayed, for example, by the graphical user interface 135 at the client 130.

FIG. 21 depicts a block diagram illustrating a computing system 500 consistent with implementations of the current subject matter. Referring to FIGS. 19 and 21, the computing system 500 can be used to implement the machine learning controller 110 and/or any components therein.

Figure 5:
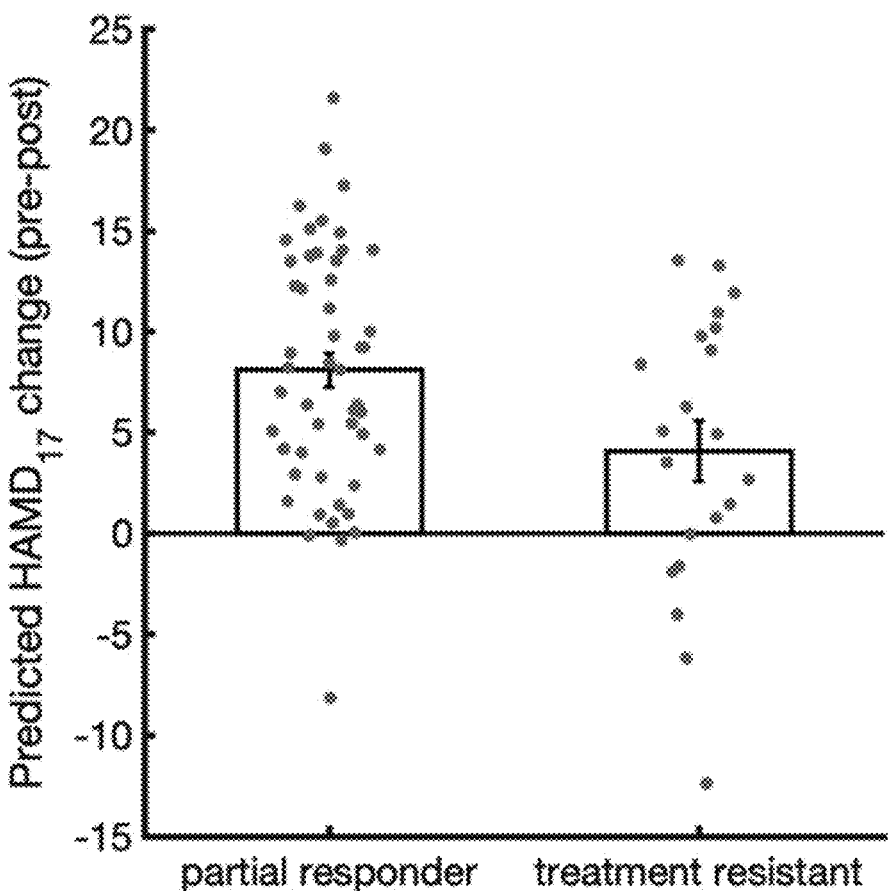
FIG. 5. Prediction of treatment outcome by the EMBARC-trained SELSER rsEEG model, applying to baseline eyes open rsEEG of the second depression study cohort. The plot shows the predicted HAMD$_{17}$ change for patients who are partial responder (N=51) or treatment resistant (N=21). These data demonstrate the predicted HAMD$_{17}$ change is significantly larger in patients whose are partial responders than in those who are treatment resistant (two-sample t-test p=0.016).

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the machine learning controller 110. In some example embodiments, the processor 510 can be a single-threaded processor. Alternately, the processor 510 can be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a solid state drive, a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Performance Evaluation Using Cross-Validation

Stratified 10-fold leave-subject-out cross-validation[55,56] (FIG. 9) was employed to assess the predictive performance of each prediction approach. More specifically, the data were randomly partitioned into 10 subsets, such that each subset containing an approximately equal number of subjects from each of the four study sites. A subset was left out as the test data, and the remaining 9 subsets were used as the training data. For SELSER, the regularization parameter $\lambda$ was determined using an inner 10-fold cross-validation on the training data. The process was then repeated 10 times, where each of the 10 subsets was used exactly once as the test data. As a result, each subject had a predicted $HAMD_{17}$ score change. To enhance the stability of the prediction, the data were randomized 10 times and the stratified 10-fold cross-validation was run on each randomized data. The median of the resulting 10 predicted $HAMD_{17}$ score changes of each subject was used as the final prediction. The prediction performance was then quantified by the Pearson's correlation coefficient and root mean square error (RMSE) between the cross-validated prediction of the $HAMD_{17}$ score change and the true $HAMD_{17}$ score change. The p-value for the one-tailed alternative hypothesis that the Pearson's correlation coefficient was greater than 0 was also reported.

Specificity of the prediction was tested by applying, at each fold of stratified 10×10 cross-validation, the prediction model to the data from the other treatment arm, which was summarized for each participant by taking the median of the 100 folds of cross-validation.

Significance Test

A non-parametric permutation test was used to assess the statistical significance of the treatment prediction results. The observed $HAMD_{17}$ score changes were randomly shuffled across subjects 1000 times. Each time the cross-validated prediction procedure was repeated, resulting in a distribution of the Pearson's correlation coefficient. The P value was then defined as the proportion of cross-validated correlation coefficients that were greater than the cross-validated correlation coefficient without permutation.

Application of Machine Learning Models to Independent MDD Data

Calculating rsEEG Predictions in the Second MDD Study

We applied the result of the alpha SELSER model trained on the sertraline arm of the EMBARC sample to data from the 2nd MDD study in which rsEEG data were collected from 72 patients with depression who were assessed in cross-sectionally at the baseline visit. Since 37 patients' EEG data were recorded with a new amplifier (i.e., the EGI Net Amps 300 amplifier) distinct from those used in EMBARC, the mean-removal site correction procedure was performed on both the EMBARC data to train the model, and the 37 patients' EEG data in the 2nd study, as in the leave-study-site-out analysis. The rsEEG were fed into Equation (1) to yield predictions with the SELSER model trained at each fold of cross-validation in EMBARC. The prediction was summarized for each participant by taking the median of the predictions from the 100 folds of cross-validation. This yielded a measure of the EMBARC SELSER model expression strength for each individual in the second MDD study, expressed as a predicted $HAMD_{17}$ change for each patient. Given the focus in the present study on testing the generalizability of the EMBARC sertraline-predictive signature in an independent data set, we compared the SELSER model-predicted $HAMD_{17}$ change scores between patients with a treatment-resistant profile on the ATRQ (failed two or more medications in the current episode) versus those who showed a partial response to antidepressant treatment within-episode.

Calculating rsEEG Predictions in the Third MDD Study

We applied the result of the alpha SELSER model trained on the sertraline arm of the EMBARC sample to data from the 3rd MDD study in which rsEEG data were collected from 24 patients with depression who were assessed in a cross-sectional manner (i.e. without treatment). Since the EEG data were recorded with yet another amplifier distinct from those used in EMBARC, the mean-removal site correction procedure was performed, as in the leave-study-site-out analysis. Due to the difference of electrode montages between this study and EMBARC, the SELSER model trained on EMBARC cannot be directly applied to this study. To address this issue, we source localized the rsEEG from the study based on the linear inverse matrix obtained similarly as in EMBARC, and then mapped the source activity to the EMBARC electrodes via the lead-field matrix from EMBARC. Next, the mapped rsEEG at EMBARC electrodes were fed into Equation (1) to yield predictions with the SELSER model trained at each fold of cross-validation in EMBARC. The prediction was summarized for each participant by taking the median of the predictions from the 100 folds of cross-validation.

Calculating Task fMRI Predictions in the Third MDD Study

We also applied a previously-described RVM model trained on emotional conflict task fMRI data from EMBARC to data from the 3rd MDD study[21]. Development of the model on EMBARC data is described in brief below. Extractions were conducted on cortical regions of interest (ROIs), defined based on a recently-published cortical parcellation derived from applying a combination of local gradient analysis and global signal similarity on an independent resting-state fMRI cohort[57]. Since functional parcellations typically rely on resting-state connectivity patterns, which may or may not adequately describe activity patterns in the emotional conflict task, we pooled ROIs from the 200, 400, and 600 region parcellations in order to limit parcellation-related specificity. ROIs were mapped to seven previously identified functional networks based on the spatial overlap between each ROI and each network[57]. In addition to these cortical ROIs, subcortical ROIs included striatal[58] and cerebellar[59] parcellations based on the same seven functional networks, amygdala ROIs[60], anterior and posterior hippocampal ROIs[61] and the thalamus[62]. We then regressed imaging site out of these data using multiple linear regression within the training set at each run of the RVM model, and the residualized brain signals were then used for predicting the $HAMD_{17}$ score change with the RVM model trained at each fold of cross-validation in EMBARC. The prediction was summarized for each participant by taking the median of the predictions from the 100 folds of cross-validation. fMRI data from our third MDD study were preprocessed in the same manner, and the EMBARC-derived weight vector was applied to the extracted ROI data to determine each participant's strength of expression of the EMBARC fMRI RVM model.

Correlating spTMS/EEG with rsEEG Predictions in Third MDD Study

To quantify in the 3rd MDD study the correlation between the spTMS/EEG responses and the EMBARC-defined rsEEG phenotype, we employed SELSER to learn predictive models from the spTMS/EEG data to the rsEEG predictions, and calculated the leave-one-out cross-validated Pearson's correlation coefficients between the predicted rsEEG predictions and true rsEEG predictions. The SELSER analysis was performed separately for the seven stimulation sites (bilateral pDLPFC, bilateral aDLPFC, bilateral M1, and V1), the same set of frequency bands as used in the rsEEG prediction analysis (theta, alpha, beta, and gamma), and for three time windows relative to the TMS pulse (0-200 ms, 200-400 ms, 400-600 ms). For each SELSER analysis, the spTMS/EEG data were concatenated across trials. Significance was evaluated after correcting for the false discovery rate ($p<0.05$) across all SELSER models (i.e. encompassing stimulation sites x frequency bins x time windows).

Testing the Relationship Between rsEEG Predictions and Treatment Outcome in Fourth MDD Study We computed each patient's expression of the EMBARC-trained SELSER rsEEG model (expressed as predicted $HAMD_{17}$ change) using the same mean site removal procedure as above. We then conducted linear mixed models (SPSS version 25, IBM Corporation) between the SELSER rsEEG-generated predicted $HAMD_{17}$ change and outcome on the BDI as well as each of the DASS subscales, separately by rTMS protocol. Terms were time, predicted $HAMD_{17}$ change and predicted $HAMD_{17}$ change x time, using a random intercept and fixed slope. A Bonferroni correction for eight comparisons (two simulation frequencies, four outcome measures) was then conducted on the predicted $HAMD_{17}$ change x time results.

TABLE 4

Pseudocode of Accelerated proximal gradient method (APGM) for solving Problem (5).

Algorithm: Accelerated Proximal Gradient Method for SELSER

Input: Bandpass filtered EEG data $\{X_i\}_{i=1}^{M}$ from training subjects and their corresponding treatment outcome $\{y_i\}_{i=1}^{M}$. Regularization parameter $\lambda$.

Output: Spatial filters $\{w_k\}_{k=1}^{L}$, regression weights $\{\beta_k\}_{k=1}^{L}$ and intercept b.

Initialization: $W(0) = W(1) = 0$, $b(0) = b(1) = 0$, $\alpha(0) = \alpha(1) = 1$, $\mu(0) = 1$, $t = 0$.

1: For i = 1 to M

2: $\left| C_i = \dfrac{X_i X_i^T}{N} \right.$

3: End

4: While not converged do

5: | $t = t + 1$.

6: | $\mu(t) = \mu(t - 1)$.

7: $\left| W(t) = W(t) + \dfrac{\alpha(t-1)-1}{\alpha(t)}(W(t) - W(t-1)) \right.$ 8: $\left| b(t) = b(t) + \dfrac{\alpha(t-1)-1}{\alpha(t)}(b(t) - b(t-1)) \right.$ 9: | $\nabla_W h(W(t), b(t)) = 2 \sum_{i=1}^{M}(Tr(W^T(t)C_i) + b(t) - y_i)C_i$.

10: | $\nabla_b h(W(t), b(t)) = 2 \sum_{i=1}^{M}(Tr(W^T(t)C_i) + b(t) - y_i)$.

11: | While 1 do

12: | | $U(t) = W(t) - \mu(t)\nabla_W h(W(t), b(t))$.

13: $\quad$ $b(t+1) = b(t) - \mu(t)\nabla_b h(W(t), b(t))$.

14: $\quad$ Singular value decomposition: $U(t) = U\Sigma V^T$.

15: $\quad$ $W(t+1) = UE_{\lambda\mu(t)}V^T$, with $(\Sigma_{\lambda\mu(t)})_{ii} = \max\{\Sigma_{ii} - \lambda\mu(t), 0\}$.

16: $\quad$ $h(W(t+1), b(t+1)) = \sum_{i=1}^{M}(Tr(W^T(t+1)C_i) + b(t+1) - y_i)^2$.

17: $\quad$ $Q_{\mu(t)}(\{W(t+1), b(t+1)\}, \{W(t), b(t)\}) = h(W(t), b(t)) +$
$\quad\quad Tr([\nabla_W h(W(t), b(t))]^T (W(t+1) - W(t)) + \nabla_b h(W(t), b(t))(b(t+1) -$
$\quad\quad b(t)) + 1/2\mu(t)(\|W(t+1) - W(t)\|_F^2 + (b(t+1) - b(t))^2$.

TABLE 4-continued

Pseudocode of Accelerated proximal gradient method (APGM) for solving Problem (5).

18:     If h(W(t +1), b(t + 1)) ≤ Q$_{\mu(t)}$ ({W(t + 1), b(t + 1)}, {W(t), b(t)})
19:         break
20:     End
21:     μ(t) = 0.5 · μ(t).
22:     End 23:     $\alpha(t + 1) = \dfrac{1 + \sqrt{1 + 4\alpha^2(t)}}{2}$.

24: End
25: Eigendecomposition: W(t) = $\Sigma_{k=1}^{L}$ β$_k$w$_K$w$_k^T$, b = b(t).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random query memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

REFERENCES FOR EXAMPLE 2

1. First, M., Spitzer, R., Gibbon, M. & William, J. Structured Clinical Interview fpr DSM-IV-TR Axis 1 disorders, Research Version, Patient Edition (SCID-I/P) New York, NY: New York State Psychiatric Institute, Biometric research; 2002. 73 Maxwell, M. Bethesda, MD (1992).
2. Trivedi, M. H., et al. Establishing moderators and biosignatures of antidepressant response in clinical care (EMBARC): Rationale and design. J Psychiatr Res 78, 11-23 (2016).
3. Team, R. C. R: A language and environment for statistical computing. (R Foundation for Statistical Computing, Vienna, Austria, 2015).
4. van Buuren, S. & Groothuis-Oudshoorn, K. mice: Multivariate Imputation by Chained Equations in R. 2011 45, 67 (2011).
5. Mullen, T. NITRC: CleanLine: Tool/Resource Info. (2012).
6. Perrin, F., Pernier, J., Bertrand, O. & Echallier, J. Spherical splines for scalp potential and current density mapping. Electroencephalography and clinical neurophysiology 72, 184-187 (1989).
7. Bell, A. J. & Sejnowski, T. J. An information-maximization approach to blind separation and blind deconvolution. Neural computation 7, 1129-1159 (1995).
8. Trivedi, M. H., et al. Comprehensive phenotyping of depression disease trajectory and risk: Rationale and design of DFW 5000. Submitted.
9. Egner, T., Etkin, A., Gale, S. & Hirsch, J. Dissociable neural systems resolve conflict from emotional versus nonemotional distracters. Cereb Cortex 18, 1475-1484 (2008).
10. Etkin, A., Egner, T., Peraza, D. M., Kandel, E. R. & Hirsch, J. Resolving emotional conflict: a role for the rostral anterior cingulate cortex in modulating activity in the amygdala. Neuron 51, 871-882 (2006).
11. Ekman, P. & Friesen, W. V. Pictures of Facial Affect, (Consulting Psychologists, Palo Alto, CA, 1976).
12. Etkin, A., Buchel, C. & Gross, J. J. The neural bases of emotion regulation. Nat Rev Neurosci 16, 693-700 (2015).
13. Gyurak, A., Gross, J. J. & Etkin, A. Explicit and implicit emotion regulation: a dual-process framework. Cogn Emot 25, 400-412 (2011).
14. Gratton, G., Coles, M. G. & Donchin, E. Optimizing the use of information: strategic control of activation of responses. J Exp Psychol Gen 121, 480-506 (1992).
15. Kerns, J. G., et al. Anterior cingulate conflict monitoring and adjustments in control. Science 303, 1023-1026 (2004).
16. Egner, T. & Hirsch, J. Cognitive control mechanisms resolve conflict through cortical amplification of task-relevant information. Nat Neurosci 8, 1784-1790 (2005).
17. Jenkinson, M., Beckmann, C. F., Behrens, T. E., Woolrich, M. W. & Smith, S. M. FSL. Neuroimage 62, 782-790 (2012).
18. Smith, S. M., et al. Advances in functional and structural MR image analysis and implementation as FSL. Neuroimage 23 Suppl 1, S208-219 (2004).
19. Friston, K. J., et al. Statistical parametric maps in functional imaging: a general linear approach. Hum Brain Mapp 2, 189-210 (1995).
20. Chen, A. C., et al. Causal interactions between fronto-parietal central executive and default-mode networks in humans. Proceedings of the National Academy of Sciences 110, 19944-19949 (2013).

21. Gregory A. Fonzo, A. E., Yu Zhang, Wei Wu, Crystal Cooper, Cherise Chin-Fatt, Manish K. Jha, Joseph Trombello, Thilo Deckersbach, Phil Adams, Melvin McInnis, Patrick J. McGrath, Myrna M. Weissman, Maurizio Fava, Madhukar H. Trivedi. Brain Regulation of Emotional Conflict Differentiates Response to Antidepressants Versus Placebo in Depression. Nature Human Behaviour (2019).
22. Wu, W., et al. ARTIST: A fully automated artifact rejection algorithm for single-pulse TMS-EEG data. Human brain mapping 39, 1607-1625 (2018).
23. Donse, L., Padberg, F., Sack, A. T., Rush, A. J. & Arns, M. Simultaneous rTMS and psychotherapy in major depressive disorder: Clinical outcomes and predictors from a large naturalistic study. Brain stimulation 11, 337-345 (2018).
24. Krepel, N., et al. Non-replication of neurophysiological predictors of non-response to rTMS in depression and neurophysiological data-sharing proposal. Brain Stimulation: Basic, Translational, and Clinical Research in Neuromodulation 11, 639-641 (2018).
25. Arns, M., Drinkenburg, W. H., Fitzgerald, P. B. & Kenemans, J. L. Neurophysiological predictors of non-response to rTMS in depression. Brain stimulation 5, 569-576 (2012).
26. Mir-Moghtadaei, A., et al. Concordance between BeamF3 and MRI-neuronavigated target sites for repetitive transcranial magnetic stimulation of the left dorsolateral prefrontal cortex. Brain stimulation 8, 965-973 (2015).
27. Beck, A. T. The current state of cognitive therapy: a 40-year retrospective. Archives of General Psychiatry 62, 953-959 (2005).
28. Lovibond, P. F. & Lovibond, S. H. The structure of negative emotional states: Comparison of the Depression Anxiety Stress Scales (DASS) with the Beck Depression and Anxiety Inventories. Behaviour research and therapy 33, 335-343 (1995).
29. Srebro, N. & Jaakkola, T. Weighted low-rank approximations. in Proceedings of the 20th International Conference on Machine Learning (ICML-03) 720-727 (2003).
30. Candès, E. J., Li, X., Ma, Y. & Wright, J. Robust principal component analysis? Journal of the ACM (JACM) 58, 11 (2011).
31. Wright, J., Ganesh, A., Rao, S., Peng, Y. & Ma, Y. Robust principal component analysis: Exact recovery of corrupted low-rank matrices via convex optimization, in Advances in neural information processing systems 2080-2088 (2009).
32. Tomioka, R. & Müller, K.-R. A regularized discriminative framework for EEG analysis with application to brain-computer interface. NeuroImage 49, 415-432 (2010).
33. Boyd, S. & Vandenberghe, L. Convex optimization, (Cambridge university press, 2004).
34. Parikh, N. & Boyd, S. Proximal algorithms. Foundations and Trends® in Optimization 1, 127-239 (2014).
35. Liu, J., Ji, S. & Ye, J. Multi-task feature learning via efficient 1 2, 1-norm minimization, in Proceedings of the twenty-fifth conference on uncertainty in artificial intelligence 339-348 (AUAI Press, 2009).
36. Cai, J.-F., Candès, E. J. & Shen, Z. A singular value thresholding algorithm for matrix completion. SIAM Journal on optimization 20, 1956-1982 (2010).
37. Nesterov, Y. E. A method for solving the convex programming problem with convergence rate O $(1/k^2)$. in Dokl. akad. nauk Sssr, Vol. 269 543-547 (1983).

38. Tipping, M. E. Sparse Bayesian learning and the relevance vector machine. Journal of machine learning research 1, 211-244 (2001).

39. Zhang, Y., et al. Sparse Bayesian classification of EEG for brain-computer interface. IEEE Transactions on Neural Networks and Learning Systems 27, 2256-2267 (2016).

40. Cawley, G. C. & Talbot, N. L. Gene selection in cancer classification using sparse logistic regression with Bayesian regularization. Bioinformatics 22, 2348-2355 (2006).

41. Li, Y., Campbell, C. & Tipping, M. Bayesian automatic relevance determination algorithms for classifying gene expression data. Bioinformatics 18, 1332-1339 (2002).

42. Haufe, S., et al. On the interpretation of weight vectors of linear models in multivariate neuroimaging. Neuroimage 87, 96-110 (2014).

43. Gramfort, A., Papadopoulo, T., Olivi, E. & Clerc, M. OpenMEEG: opensource software for quasistatic bioelectromagnetics. Biomedical engineering online 9, 45 (2010).

44. Fischl, B. FreeSurfer. Neuroimage 62, 774-781 (2012).

45. Pascual-Marqui, R. D. Standardized low-resolution brain electromagnetic tomography (sLORETA): technical details. Methods Find Exp Clin Pharmacol 24, 5-12 (2002).

46. Bruder, G. E., et al. Electroencephalographic alpha measures predict therapeutic response to a selective serotonin reuptake inhibitor antidepressant: pre-and post-treatment findings. Biological psychiatry 63, 1171-1177 (2008).

47. Olbrich, S. & Arns, M. EEG biomarkers in major depressive disorder: discriminative power and prediction of treatment response. International Review of Psychiatry 25, 604-618 (2013).

48. Leuchter, A. F., Cook, I. A., Witte, E. A., Morgan, M. & Abrams, M. Changes in brain function of depressed subjects during treatment with placebo. American Journal of Psychiatry 159, 122-129 (2002).

49. Hunter, A. M., Leuchter, A. F., Morgan, M. L. & Cook, I. A. Changes in brain function (quantitative EEG cordance) during placebo lead-in and treatment outcomes in clinical trials for major depression. American Journal of Psychiatry 163, 1426-1432 (2006).

50. Comon, P. Independent component analysis, a new concept? Signal processing 36, 287-314 (1994).

51. Jolliffe, I. Principal component analysis. in International encyclopedia of statistical science 1094-1096 (Springer, 2011).

52. Makeig, S., Bell, A. J., Jung, T.-P. & Sejnowski, T. J. Independent component analysis of electroencephalographic data. in Advances in neural information processing systems 145-151 (1996).

53. Ghosh-Dastidar, S., Adeli, H. & Dadmehr, N. Principal component analysis-enhanced cosine radial basis function neural network for robust epilepsy and seizure detection. IEEE Transactions on Biomedical Engineering 55, 512-518 (2008).

54. Cichocki, A. & Amari, S.-i. Adaptive blind signal and image processing: learning algorithms and applications, (John Wiley & Sons, 2002).

55. Witten, I. H., Frank, E., Hall, M. A. & Pal, C. J. Data Mining: Practical machine learning tools and techniques, (Morgan Kaufmann, 2016).

56. Kohavi, R. A study of cross-validation and bootstrap for accuracy estimation and model selection. in Ijcai, Vol. 14 1137-1145 (Montreal, Canada, 1995).

57. Schaefer, A., et al. Local-Global Parcellation of the Human Cerebral Cortex from Intrinsic Functional Connectivity MRI. Cereb Cortex, 1-20 (2017).

58. Choi, E. Y., Yeo, B. T. & Buckner, R. L. The organization of the human striatum estimated by intrinsic functional connectivity. J Neurophysiol 108, 2242-2263 (2012).

59. Buckner, R. L., Krienen, F. M., Castellanos, A., Diaz, J. C. & Yeo, B. T. The organization of the human cerebellum estimated by intrinsic functional connectivity. J Neurophysiol 106, 2322-2345 (2011).

60. Patenaude, B., Smith, S. M., Kennedy, D. N. & Jenkinson, M. A Bayesian model of shape and appearance for subcortical brain segmentation. Neuroimage 56, 907-922 (2011).

61. Chen, A. C. & Etkin, A. Hippocampal network connectivity and activation differentiates post-traumatic stress disorder from generalized anxiety disorder. Neuropsychopharmacology 38, 1889-1898 (2013).

62. Behrens, T. E., et al. Non-invasive mapping of connections between human thalamus and cortex using diffusion imaging. Nat Neurosci 6, 750-757 (2003).

Embodiments

Embodiment 1. A system, including: at least one data processor; and at least one memory storing instructions which, when executed by the at least one data processor, result in operations including: determining a treatment outcome prediction for a patient by at least applying, to a representation of a first data corresponding to one or more brain signals of the patient, a machine learning model, the machine learning model including a filter configured to generate, based at least on the representation of the first data, a first plurality of latent signals, the machine learning model further including a regression model configured to generate, based at least on a feature of each of the first plurality of latent signals, the treatment outcome prediction, the machine learning model having been trained by at least optimizing the filter to generate a reduced quantity of latent signals whose feature minimizes an error in the treatment outcome prediction generated by the regression model; and providing an indication corresponding to the treatment outcome prediction.

Embodiment 2. The system of embodiment 1, wherein the first data includes an electroencephalogram (EEG) data, a transcranial magnetic stimulation electroencephalogram (TMS-EEG) data, a magnetoencephalography (MEG) data, a functional magnetic resonance imaging (fMRI) data, and/or a functional near-infrared spectroscopy (fNJRS) data.

Embodiment 3. The system of any of embodiment 1-2, wherein the representation of the first data includes a covariance matrix summarizing a spatial distribution, a frequency distribution, and/or a power distribution of the brain signals.

Embodiment 4. The system of any of embodiments 1-3, wherein the reduced quantity of latent signals includes a minimum quantity of latent signals.

Embodiment 5. The system of any of embodiments 1-4, wherein the feature includes a band power, a power-envelope connectivity, a weighted phase-lag index, an imaginary coherence, a cordance, an approximate entropy, a Shannon entropy, and/or a cross-frequency coupling.

Embodiment 6. The system of any of embodiments 1-5, wherein the filter is configured to reduce a dimensionality of the first data of the patient including by merging, into a single latent signal, two or more signals in the first data, and wherein the two or more signals are merged based at least on a covariance between the two or more signals.

Embodiment 7. The system of any of embodiments 1-6, wherein the machine learning model further includes a feature extractor configured to extract the feature of each of the first plurality of latent signals.

Embodiment 8. The system of any of embodiments 1-7, further including: training, based at least on training data, the machine learning model, the training data including a second data corresponding to one or more brain signals of a plurality of subjects, and the training data further including a treatment outcome associated with each of the plurality of subjects.

Embodiment 9. The system of embodiment 8, further including: clustering the second data, the second data being clustered based at least on the feature of each of a second plurality of latent signals generated by the filter based on the second data, and the clustering generating one or more clusters that each correspond to a type of a psychiatric disease.

Embodiment 10. The system of embodiment 9, further including: determining, based at least on the feature of each of the first plurality of latent signals associated with the patient, a diagnosis for the patient indicating the patient as having one or more types of the psychiatric disease, the diagnosis being determined by at least determining a distance between the feature of each of the first plurality of latent signals associated with the patient and the one or more clusters.

Embodiment 11. The system of any of embodiments 9-10, wherein the psychiatric disease includes depression, mania, bipolar disorder, anxiety, obsessive-compulsive disorder, schizophrenia, an eating disorder, stroke, dementia, Alzheimer's disease, Parkinson's disease, or attention deficit disorder.

Embodiment 12. The system of any of embodiments 1-11, wherein the regression model includes a linear regression model.

Embodiment 13. The system of any of embodiments 1-12, wherein the one or more brain signals include resting state brain signals.

Embodiment 14. The system of any of embodiments 1-13, wherein the one or more brain signals include brain signals during and/or after performance of a task.

Embodiment 15. The system of any of embodiments 1-14, wherein the one or more brain signals include brain signals responsive to a direct brain stimulation.

Embodiment 16. The system of any of embodiments 1-15, wherein the treatment outcome prediction includes a first response to a first treatment and a second response to a second treatment.

Embodiment 17. The system of embodiment 16, wherein the first treatment includes a first treatment modality and the second treatment includes a second treatment modality, and wherein the first treatment modality and the second treatment modality each include a different one of medication, psychotherapy, and somatic therapy.

Embodiment 18. The system of embodiment 16, wherein the first treatment and the second treatment each include a different variety of a same treatment modality.

Embodiment 19. The system of embodiment 18, wherein the first treatment and the second treatment each include a different one of a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, and an over-the-counter antidepressant.

Embodiment 20. The system of embodiment 18, wherein the first treatment and the second treatment each include a different one of electroconvulsive therapy (ECT), vagal nerve stimulation (VNS), and transcranial magnetic stimulation (TMS).

Embodiment 21. The system of any of embodiments 16-20, wherein the treatment outcome prediction further includes, based at least on a difference between the first response and the second response, a selection of the first treatment and/or the second treatment.

Embodiment 22. The system of any of embodiments 1-21, wherein the treatment outcome prediction includes a third response to a treatment and a fourth response to a placebo, and wherein the treatment outcome prediction further identifies, based at least on a difference between the third response and the fourth response, the patient as being responsive or non-responsive to the treatment.

Embodiment 23. The system of embodiment 22, wherein the third response and the fourth response include one or more symptoms, behavioral tests, and psychological tests.

Embodiment 24. The system of any of embodiments 1-23, wherein the first data includes a first change in the one or more brain signals between at a first time prior to a treatment and a second time subsequent to the treatment, wherein the machine learning model is trained to correlate the first change in the one or more brain signals and a second change in one or more symptoms exhibited by the patient in response to the treatment, and wherein the treatment outcome prediction includes the second change in the one or more symptoms exhibited by the patient.

Embodiment 25. A system, including: at least one data processor; and at least one memory storing instructions which, when executed by the at least one data processor, result in operations including: training, based at least on training data, a machine learning model, the training data including a first data corresponding to one or more brain signals of a subject, the training data further including a treatment outcome associated with the subject, the machine learning model including a filter configured to generate, based at least on the first data, a first plurality of latent signals, the machine learning model further including a regression model configured to generate, based at least on a feature of each of the first plurality of latent signals, a first treatment outcome prediction for the subject, the training of the machine learning model including optimizing the filter to generate a reduced quantity of latent signals whose feature minimizes an error in the first treatment outcome prediction generated by the regression model, the error including a difference between the treatment outcome of the subject and the first treatment outcome prediction generated by the regression model; and deploying the trained machine learning model.

Embodiment 26. The system of embodiment 25, wherein the first data includes an electroencephalogram (EEG) data, a transcranial magnetic stimulation electroencephalogram (TMS-EEG) data, a magnetoencephalography (MEG) data, a functional magnetic resonance imaging (fMRI) data, and/or a functional near-infrared spectroscopy (fNIRS) data.

Embodiment 27. The system of any of embodiments 25-26, wherein the training data includes a representation of the first data, and wherein the representation of the first data includes a covariance matrix summarizing a spatial distribution, a frequency distribution, and/or a power distribution of the brain signals.

Embodiment 28. The system of any of embodiments 25-27, wherein the trained machine learning model is deployed to at least determine, based at least on a representation of a second data corresponding to one or more brain signals of a subject, a second treatment outcome prediction for the patient.

Embodiment 29. The system of embodiment 28, wherein the second treatment outcome prediction includes a first response to a first treatment and a second response to a second treatment, and wherein the second treatment outcome prediction further includes, based at least on a difference between the first response and the second response, a selection of the first treatment and/or the second treatment.

Embodiment 30. The system of embodiment 29, wherein the first treatment includes a first treatment modality and the second treatment includes a second treatment modality, and wherein the first treatment modality and the second treatment modality each include a different one of medication, psychotherapy, and somatic therapy.

Embodiment 31. The system of embodiment 29, wherein the first treatment and the second treatment each include a different variety of a same treatment modality.

Embodiment 32. The system of any of embodiments 28-31, wherein the second treatment outcome prediction includes a third response to a treatment and a fourth response to a placebo, and wherein the second treatment outcome prediction further identifies, based at least on a difference between the third response and the fourth response, the patient as being responsive or non-responsive to the treatment.

Embodiment 33. The system of any of embodiments 25-32, wherein the one or more brain signals include resting state brain signals.

Embodiment 34. The system of any of embodiments 25-33, wherein the one or more brain signals include brain signals during and/or after performance of a task.

Embodiment 35. The system of any of embodiments 25-34, wherein the one or more brain signals include brain signals responsive to a direct brain stimulation.

Embodiment 36. A computer-implemented method, including: determining a treatment outcome prediction for a patient by at least applying, to a representation of a first data corresponding to one or more brain signals of the patient, a machine learning model, the machine learning model including a filter configured to generate, based at least on the representation of the first data, a first plurality of latent signals, the machine learning model further including a regression model configured to generate, based at least on a feature of each of the first plurality of latent signals, the treatment outcome prediction, the machine learning model having been trained by at least optimizing the filter to generate a reduced quantity of latent signals whose feature minimizes an error in the treatment outcome prediction generated by the regression model; and providing an indication corresponding to the treatment outcome prediction.

Embodiment 37. The method of embodiment 36, wherein the first data includes an electroencephalogram (EEG) data, a transcranial magnetic stimulation electroencephalogram (TMS-EEG) data, a magnetoencephalography (MEG) data, a functional magnetic resonance imaging (fMRI) data, and/or a functional near-infrared spectroscopy (fNIRS) data.

Embodiment 38. The method of any of embodiment 36-37, wherein the representation of the first data includes a covariance matrix summarizing a spatial distribution, a frequency distribution, and/or a power distribution of the brain signals.

Embodiment 39. The method of any of embodiments 36-38, wherein the reduced quantity of latent signals includes a minimum quantity of latent signals.

Embodiment 40. The method of any of embodiments 36-39, wherein the feature includes a band power, a power-envelope connectivity, a weighted phase-lag index, an imaginary coherence, a cordance, an approximate entropy, a Shannon entropy, and/or a cross-frequency coupling.

Embodiment 41. The method of any of embodiments 36-40, wherein the filter is configured to reduce a dimensionality of the first data of the patient including by merging, into a single latent signal, two or more signals in the first data, and wherein the two or more signals are merged based at least on a covariance between the two or more signals.

Embodiment 42. The method of any of embodiments 36-41, wherein the machine learning model further includes a feature extractor configured to extract the feature of each of the first plurality of latent signals.

Embodiment 43. The method of any of embodiments 36-42, further including: training, based at least on training data, the machine learning model, the training data including a second data corresponding to one or more brain signals of a plurality of subjects, and the training data further including a treatment outcome associated with each of the plurality of subjects.

Embodiment 44. The method of embodiment 43, further including: clustering the second data, the second data being clustered based at least on the feature of each of a second plurality of latent signals generated by the filter based on the second data, and the clustering generating one or more clusters that each correspond to a type of a psychiatric disease.

Embodiment 45. The method of embodiment 44, further including: determining, based at least on the feature of each of the first plurality of latent signals associated with the patient, a diagnosis for the patient indicating the patient as having one or more types of the psychiatric disease, the diagnosis being determined by at least determining a distance between the feature of each of the first plurality of latent signals associated with the patient and the one or more clusters.

Embodiment 46. The method of any of embodiments 44-45, wherein the psychiatric disease includes depression, mania, bipolar disorder, anxiety, obsessive-compulsive disorder, schizophrenia, an eating disorder, stroke, dementia, Alzheimer's disease, Parkinson's disease, or attention deficit disorder.

Embodiment 47. The method of any of embodiments 36-46, wherein the regression model includes a linear regression model.

Embodiment 48. The method of any of embodiments 36-47, wherein the one or more brain signals include resting state brain signals.

Embodiment 49. The method of any of embodiments 36-48, wherein the one or more brain signals include brain signals during and/or after performance of a task.

Embodiment 50. The method of any of embodiments 36-49, wherein the one or more brain signals include brain signals responsive to a direct brain stimulation.

Embodiment 51. The method of any of embodiments 36-50, wherein the treatment outcome prediction includes a first response to a first treatment and a second response to a second treatment.

Embodiment 52. The method of embodiment 51, wherein the first treatment includes a first treatment modality and the second treatment includes a second treatment modality, and wherein the first treatment modality and the second treatment modality each include a different one of medication, psychotherapy, and somatic therapy.

Embodiment 53. The method of embodiment 51, wherein the first treatment and the second treatment each include a different variety of a same treatment modality.

Embodiment 54. The method of embodiment 53, wherein the first treatment and the second treatment each include a different one of a selective serotonin reuptake inhibitor (SSRI), a serotonin and norepinephrine reuptake inhibitor (SNRI), a serotonin modulator and stimulator (SMS), a serotonin antagonist and reuptake inhibitor (SARI), a norepinephrine reuptake inhibitor (NRI), a norepinephrine-dopamine reuptake inhibitor (NDRI), a monoamine oxidase inhibitor (MAOI), a tetracyclic antidepressant (TeCA), an atypical antipsychotic, a tricyclic antidepressant (TCA), an alternative antidepressant, and an over-the-counter antidepressant.

Embodiment 55. The method of embodiment 53, wherein the first treatment and the second treatment each include a different one of electroconvulsive therapy (ECT), vagal nerve stimulation (VNS), and transcranial magnetic stimulation (TMS).

Embodiment 56. The method of any of embodiments 51-55, wherein the treatment outcome prediction further includes, based at least on a difference between the first response and the second response, a selection of the first treatment and/or the second treatment.

Embodiment 57. The method of any of embodiments 36-56, wherein the treatment outcome prediction includes a third response to a treatment and a fourth response to a placebo, and wherein the treatment outcome prediction further identifies, based at least on a difference between the third response and the fourth response, the patient as being responsive or non-responsive to the treatment.

Embodiment 58. The method of embodiment 57, wherein the third response and the fourth response include one or more symptoms, behavioral tests, and psychological tests.

Embodiment 59. The method of any of embodiments 36-58, wherein the first data includes a first change in the one or more brain signals between at a first time prior to a treatment and a second time subsequent to the treatment, wherein the machine learning model is trained to correlate the first change in the one or more brain signals and a second change in one or more symptoms exhibited by the patient in response to the treatment, and wherein the treatment outcome prediction includes the second change in the one or more symptoms exhibited by the patient Embodiment 60. A computer-implemented method, including: training, based at least on training data, a machine learning model, the training data including a first data corresponding to one or more brain signals of a subject, the training data further including a treatment outcome associated with the subject, the machine learning model including a filter configured to generate, based at least on the first data, a first plurality of latent signals, the machine learning model further including a regression model configured to generate, based at least on a feature of each of the first plurality of latent signals, a first treatment outcome prediction for the subject, the training of the machine learning model including optimizing the filter to generate a reduced quantity of latent signals whose feature minimizes an error in the first treatment outcome prediction generated by the regression model, the error comprising a difference between the treatment outcome of the subject and the first treatment outcome prediction generated by the regression model; and deploying the trained machine learning model.

Embodiment 61. The method of embodiment 60, wherein the first data includes an electroencephalogram (EEG) data, a transcranial magnetic stimulation electroencephalogram (TMS-EEG) data, a magnetoencephalography (MEG) data, a functional magnetic resonance imaging (fMRI) data, and/or a functional near-infrared spectroscopy (fNIRS) data.

Embodiment 62. The method of any of embodiments 60-61, wherein the training data includes a representation of the first data, and wherein the representation of the first data includes a covariance matrix summarizing a spatial distribution, a frequency distribution, and/or a power distribution of the brain signals.

Embodiment 63. The method of any of embodiments 60-62, wherein the trained machine learning model is deployed to at least determine, based at least on a representation of a second data corresponding to one or more brain signals of a subject, a second treatment outcome prediction for the patient.

Embodiment 64. The method of embodiment 63, wherein the second treatment outcome prediction includes a first response to a first treatment and a second response to a second treatment, and wherein the second treatment outcome prediction further includes, based at least on a difference between the first response and the second response, a selection of the first treatment and/or the second treatment.

Embodiment 65. The method of embodiment 64, wherein the first treatment includes a first treatment modality and the second treatment includes a second treatment modality, and wherein the first treatment modality and the second treatment modality each include a different one of medication, psychotherapy, and somatic therapy.

Embodiment 66. The method of embodiment 64, wherein the first treatment and the second treatment each include a different variety of a same treatment modality.

Embodiment 67. The method of any of embodiments 63-66, wherein the second treatment outcome prediction includes a third response to a treatment and a fourth response to a placebo, and wherein the second treatment outcome prediction further identifies, based at least on a difference between the third response and the fourth response, the patient as being responsive or non-responsive to the treatment.

Embodiment 68. The method of any of embodiments 60-67, wherein the one or more brain signals include resting state brain signals.

Embodiment 69. The method of any of embodiments 60-68, wherein the one or more brain signals include brain signals during and/or after performance of a task.

Embodiment 70. The method of any of embodiments 60-69, wherein the one or more brain signals include brain signals responsive to a direct brain stimulation.

Embodiment 71. A non-transitory computer readable medium storing instructions, which when executed by at least one data processor, result in operations including: determining a treatment outcome prediction for a patient by at least applying, to a representation of a first data corresponding to one or more brain signals of the patient, a machine learning model, the machine learning model including a filter configured to generate, based at least on the representation of the first data, a first plurality of latent signals, the machine learning model further including a regression model configured to generate, based at least on a feature of each of the first plurality of latent signals, the treatment outcome prediction, the machine learning model having been trained by at least optimizing the filter to generate a reduced quantity of latent signals whose feature minimizes an error in the treatment outcome prediction generated by the regression model; and providing an indication corresponding to the treatment outcome prediction.

Embodiment 72. A non-transitory computer readable medium storing instructions, which when executed by at least one data processor, result in operations including: training, based at least on training data, a machine learning model, the training data including a first data corresponding to one or more brain signals of a subject, the training data further including a treatment outcome associated with the subject, the machine learning model including a filter configured to generate, based at least on the first data, a first plurality of latent signals, the machine learning model further including a regression model configured to generate, based at least on a feature of each of the first plurality of latent signals, a first treatment outcome prediction for the subject, the training of the machine learning model including optimizing the filter to generate a reduced quantity of latent signals whose feature minimizes an error in the first treatment outcome prediction generated by the regression model, the error comprising a difference between the treatment outcome of the subject and the first treatment outcome prediction generated by the regression model; and deploying the trained machine learning model.

What is claimed is:

1. A non-transitory computer readable medium comprising computer readable code executable by one or more processors to:

apply a machine learning model to a representation of first data corresponding to one or more brain signals of a patient having a first psychiatric disease to generate a treatment outcome prediction for the patient in response to a placebo treatment, wherein the machine learning model is configured to:

transform the first data corresponding to one or more brain signals to generate a first plurality of latent signals, wherein applying the machine learning model further comprises applying the machine learning model to the first plurality of latent signals, and wherein the machine learning model comprises a result of performing an optimization of a latent space model that maps resting EEG data to treatment outcome by minimizing pre error, subject to constraint on a dimensionality of latent signals generated from the first data; and generate the treatment outcome prediction, based, at least in part, on: a feature of each of the first plurality of latent signals; and training data including second data corresponding to one or more representations of brain signals of a plurality of subjects having the first psychiatric disease and an outcome metric associated with each of the plurality of subjects after receiving a placebo treatment.

2. The non-transitory computer readable medium of claim 1, wherein the representation of the first data and the representation of the second data each comprise one or more of a covariance matrix summarizing a spatial distribution, a frequency distribution, or a power distribution of the brain signals.

3. The non-transitory computer readable medium of claim 1, wherein the first data comprises one or more of an electroencephalogram (EEG) data, a transcranial magnetic stimulation electroencephalogram (TMS-EEG) data, a magnetoencephalography (MEG) data, a functional magnetic resonance imaging (fMRI) data, and a functional near-infrared spectroscopy (fNIRS) data.

4. The non-transitory computer readable medium of claim 1, wherein the first psychiatric disease comprises depression, mania, bipolar disorder, anxiety, obsessive-compulsive disorder, schizophrenia, an eating disorder, stroke, dementia, Alzheimer's disease, Parkinson's disease, or attention deficit disorder.

5. The non-transitory computer readable medium of claim 1, wherein at least one of the first data and the second data include electroencephalogram (EEG) data.

6. The non-transitory computer readable medium of claim 5, wherein the EEG data is in an alpha 8-12 Hz frequency band.

7. A method comprising:

applying a machine learning model to a representation of first data corresponding to one or more brain signals of a patient having a first psychiatric disease to generate a treatment outcome prediction for the patient in response to a placebo treatment, wherein the machine learning model is configured to:

transform the first data corresponding to one or more brain signals to generate a first plurality of latent signals, wherein applying the machine learning model further comprises applying the machine learning model to the first plurality of latent signals, and wherein the machine learning model comprises a result of performing an optimization of a latent space model that maps resting EEG data to treatment outcome by minimizing prediction error, subject to a constraint on a dimensionality of latent signals generated from the first data; and generate the treatment outcome prediction, based, at least in part, on: a feature of each of the first plurality of latent signals; and training data including second data corresponding to one or more representations of brain signals of a plurality of subjects having the first psychiatric disease and an outcome metric associated with each of the plurality of subjects after receiving a placebo treatment.

8. The method of claim 7, wherein the representation of the first data and the representation of the second data each comprise one or more of a covariance matrix summarizing a spatial distribution, a frequency distribution, or a power distribution of the brain signals.

9. The method of claim 7, wherein the first data comprises one or more of an electroencephalogram (EEG) data, a transcranial magnetic stimulation electroencephalogram TMS-EEG) data, a magnetoencephalography (MEG) data, a functional magnetic resonance imaging (fMRI) data, and a functional near-infrared spectroscopy (fNIRS) data.

10. The method of claim 7, wherein the first psychiatric disease comprises depression, mania, bipolar disorder, anxiety, obsessive-compulsive disorder, schizophrenia, an eating disorder, stroke, dementia, Alzheimer's disease, Parkinson's disease, or attention deficit disorder.

11. The method of claim 7, wherein at least one of the first data and the second data include electroencephalogram (EEG) data.

12. The method of claim 11, wherein the EEG data is in an alpha 8-12 Hz frequency band.

13. A system comprising:

one or more processors; and one or more computer readable media comprising computer readable code executable by the one or more processors to:

apply a machine learning model to first data corresponding to one or more brain signals of a patient suffering from a psychiatric disease to generate a treatment outcome prediction for the patient in response to a placebo treatment, wherein the machine learning model is configured to:

transform the first data corresponding to one or more brain signals to generate a first plurality of latent signals, wherein applying the machine learning model further comprises applying the machine learning model to the first plurality of latent signals, and wherein the machine learning model comprises a result of forming an optimization of a latent space model that maps resting EEG data to treatment outcome by minimizing prediction error, subject to a constraint on a dimensionality of latent signals generated from the first data; and generate the treatment outcome prediction, based, a least in part, on: a feature of each of the first plurality of latent signals; and training data including a second data corresponding to one or more additional brain signals of a plurality of subjects and an outcome metric associated with each of the plurality of subjects after receiving a placebo treatment.

14. The system of claim 13, wherein a representation of the first data and a representation of the second data each comprise one or more of a covariance matrix summarizing a spatial distribution, a frequency distribution, or a power distribution of the brain signals.

\* \* \* \* \*